US011725204B2

(12) United States Patent
Barbieri et al.

(10) Patent No.: US 11,725,204 B2
(45) Date of Patent: Aug. 15, 2023

(54) MULTIPLEX GENOME ENGINEERING IN EUKARYOTES

(71) Applicant: Yale University, New Haven, CT (US)

(72) Inventors: Edward Barbieri, Lindenhurst, NY (US); Farren Isaacs, Stamford, CT (US)

(73) Assignee: YALE UNIVERSITY, New Haven, CT (US)

( * ) Notice: Subject to any disclaimer, the term of this patent is extended or adjusted under 35 U.S.C. 154(b) by 1089 days.

(21) Appl. No.: 16/097,091

(22) PCT Filed: Apr. 27, 2017

(86) PCT No.: PCT/US2017/029922
§ 371 (c)(1),
(2) Date: Oct. 26, 2018

(87) PCT Pub. No.: WO2017/189894
PCT Pub. Date: Nov. 2, 2017

(65) Prior Publication Data
US 2021/0222155 A1    Jul. 22, 2021

Related U.S. Application Data

(60) Provisional application No. 62/328,507, filed on Apr. 27, 2016.

(51) Int. Cl.
| | |
|---|---|
| *C12N 15/10* | (2006.01) |
| *G01N 33/50* | (2006.01) |
| *C40B 30/06* | (2006.01) |
| *C40B 40/02* | (2006.01) |

(52) U.S. Cl.
CPC ..... *C12N 15/1058* (2013.01); *C12N 15/1079* (2013.01); *C12N 15/1082* (2013.01); *C12N 15/1086* (2013.01); *C40B 30/06* (2013.01); *C40B 40/02* (2013.01); *G01N 33/5014* (2013.01); *C12N 15/102* (2013.01); *C12Q 2525/185* (2013.01); *C12Q 2543/10* (2013.01)

(58) Field of Classification Search
None
See application file for complete search history.

(56) References Cited

U.S. PATENT DOCUMENTS

| | | | |
|---|---|---|---|
| 6,139,833 A | 10/2000 | Burgess | |
| 2009/0054350 A1 | 2/2009 | Tayot | |
| 2015/0307876 A1* | 10/2015 | Hendrickson | C12N 15/113 435/375 |

FOREIGN PATENT DOCUMENTS

| | | |
|---|---|---|
| WO | 2004090146 | 10/2004 |
| WO | 2015017866 | 2/2015 |

OTHER PUBLICATIONS

Rodriguez et al. Transformation with Oligonucleotides Creating Clustered Changes in the Yeast Genome, (2012), PLoS One 7(8): e42905. doi:10.1371/journal.pone.0042905 (Year: 2012).*
Bindra et al., "Down-Regulation of Rad51 and Decreased Homologous Recombination in Hypoxic Cancer Cells" 24(19) Molecular and Cellular Biology 8504-8518 (Year: 2004).*
Alvino, et al., "Replication in hydroxyurea: it's a matter of time", Mol Cell Biol, 27:6396-406 (2007).
Amiram, et al., "Evolution of translation machinery in recoded bacteria enables multi-site incorporation of nonstandard amino acids", Nat Biotechnol., 33:1272-9 (2015).
Boyle, et al., "Recombineering to homogeneity: extension of multiplex recombineering to large-scale genome editing", Biotechnology Journal, 8(5):515-522 (2013).
Brachman, et al., "DNA replication and transcription direct a DNA strand bias in the process of targeted gene repair in mammalian cells", J Cell Sci, 117:3867-74 (2004).
Brachmann, et al., Designer Deletion Strains derived from *Saccharomyces cerevisiae* S288C: a Useful set of Strains and Plasmids for PCR-Mediated Gene Disruption and Other Applications, Yeast, 14(2):115-132 (1998).
Carr, et al., "Enhanced multiplex genome engineering through co-operative oligonucleotide co-selection", Nucleic Acids Res., 40(17):e132, 12 pages (2012).
Chen, et al., "Generation and analysis of a barcode-tagged insertion mutant library in the fission yeast Schizosaccharomyces pombe", BMC Genomics, Biomed Central LTD., 13(1):161 (2012).
Costantino, et al., "Enhanced levels of Red-mediated recombinants in mismatch repair mutants", PNAS, 100(26):15748-53 (2003).
Detloff, et al., Repair of Specific Base Pair Mismatches Formed during Meiotic Recombination in the Yeast *Saccharomyces cereviviae*, Mol. Cell. Biol., 11:737-745 (1991).
Dicarlo, et al., "Yeast oligo-mediated genome engineering (Yoge)", ACS Synth. Biol., 2:741-9 (2013).
Engstrom, et al., "Manipulation of cell cycle progression can counteract the apparent loss of correction frequency following oligonucleotide-directed gene repair", BMC Mol Biol, 8:9 (2007).
Fukagawa, et al., "The Chicken HPRT gene: a counter selectable marker for the DT40 cell line", Nucelic Acids Research, 27(9):1966-1969 (2000).

(Continued)

*Primary Examiner* — Nancy J Leith
(74) *Attorney, Agent, or Firm* — Pabst Patent Group LLP

(57) ABSTRACT

Compositions and methods for gene editing are provided. The methods employ an oligo-based annealing mechanism that is rooted in the process of DNA replication rather than homologous recombination (HR). Oligo incorporation efficiencies are comparable and often exceed those of CRISPR/cas9 editing without the need for double strand breaks (DSBs). By relying on the multiplex annealing of oligos rather than DSBs the process is highly scalable across a genomic region of interest and can generate many scarless modifications of a chromosome simultaneously. Combinatorial genomic diversity can be generated across a population of cells in a single transformation event; genomic landscapes can be traversed through successive iterations of the process, and genome-wide changes can be massively parallelized and amplified through systematic strain mating.

33 Claims, 12 Drawing Sheets
Specification includes a Sequence Listing.

(56) References Cited

OTHER PUBLICATIONS

Gallagher, et al., "Rapid editing and evolution of bacterial genomes using libraries of synthetic DNA", Nature Protocols, 9(10):2301-2316 (2014).
Gregg, et al., "Rational optimization of toIC as a powerful dual selectable marker for genome engineering", Nucleic Acids Res, 42(7):4779-90 (2014).
Huen, et al., "The involvement of replication in single stranded oligonucleotide-mediated gene repair", Nucleic Acids Research, 34(21):6183-6194 (2006).
International Search Report for the corresponding PCT application PCT/US2017/029922 dated Jul. 18, 2017.
Kow, et al., "Oligonucleotide transformation of yeast reveals mismatch repair complexes to be differentially active on DNA replication strands", PNAS, 104:11352-7 (2007).
Lajoie, et al., "Genomically recoded organisms expand biological functions", Science, 342:357-60 (2013).
Lang, et al., "Mutation rates, spectra, and genome-wide distribution of spontaneous mutations in mismatch repair deficient yeast", G3 (Bethesda), 3:1453-65 (2013).
Lee, et al., "Rad52/Rad59-dependent Recombination as a Means to Rectify Faulty Okazaki Fragment Processing", J Biol Chem, 289:15064-79 (2014).
Li, et al., "Identification of factors influencing strand bias in oligonucleotide-mediated recombination in *Escherichia coli*", Nucleic Acids Research, 31:6674-87 (2003).
Li, et al., "Usage of an intronic promoter for stable gene expression in *Saccharomyces cerevisiae*", Lett Appl Microbiol. 40(5):347-52 (2005).
Liu, et al., "Genetic re-engineering of *Saccharomyces cerevisiae* RAD51 leads to a significant increase in the frequency of gene repair in vivo", Nucleic Acids Research, 32:2093-2101 (2004).
Lubliner, et al., "Sequence features of yeast and human core promoters that are predictive of maximal promoter activity", Nucleic Acids Research, 41:5569-81 (2013).
Markham, et al., "UNAFold: Software for Nucleic Acid Folding and Hybridization", Methods Mol. Biol., 453:3-31 (2008).
Moerschell, et al., "The specificities of yeast methionine aminopeptidase and acetylation of amino-terminal methionine in vivo. Processing of altered iso-1-cytochromes c created by oligonucleotide transformation", J Biol Chem, 265:19638-43 (1990).
Moerschell, et al., "Transformation of yeast with synthetic oligonucleotides", PNAS, 85:524-8 (1988).
Parek-Olmedo, et al., "The effect of Hydroxyurea and Trichostatin A on targeted nucleotide exchange in yeast and mammalian cells", Annals of the New York Academy of Sciences, 1002:43-55 (2003).
Raghuraman, et al., "Replication dynamics of the yeast genome", Science, 294:115-21 (2001).
Raveh-Sadka, et al., "Manipulating nucleosome disfavoring sequences allows fine-tune regulation of gene expression in yeast", Nat Genet, 44:743-50 (2012).
Reyrat, et al., "Counterselectable Markers: Untapped Tools for Bacterial Genetics and Pathogenesis", Infect. Immun., 66(9):4011-4017 (1998).
Rodriguez, et al., "Transformation with oligonucleotides creating clustered changes in the yeast genome", PloS One, 7:042905 (2012).
San Filippo, et al., "Mechanism of eukaryotic homologous recombination", Annu. Rev. Biochem., 77:229-57 (2008).
Storici, et al., "Delitto perfetto targeted mutagenesis in yeast with oligonucleotides", Genet Eng (NY), 25:189-207 (2003).
Sung, "Function of yeast Rad52 protein as a mediator between replication protein A and the Rad51 recombinase", J Biol Chem, 272: 28194-7 (1997).
Wang, et al., "Programming cells by multiplex genome engineering and accelerated evolution", Nature, 460:894-8 (2009).
Winzeler, et al., "Functional Characterization of the S. cerevisiae Genome by Gene Deletion and Parallel Analysis", Science, 285(5429):901-906 (1999).
Wyrick, et al., "Genome-wide distribution of ORC and MCM proteins in S. cerevisiae: high-resolution mapping of replication origins", Science, 294:2357-60 (2001).
Yamamoto, et al., "Parameters affecting the frequencies of transformation and co-transformation with synthetic oligonucleotides in yeast", Yeast, 8:935-48 (1992a).
Yamamoto, et al., "Strand-specificity in the transformation of yeast with synthetic oligonucleotides", Genetics, 131:811-9 (1992b).

* cited by examiner

| | WT | Oligo | Mutant | Type | Site |
|---|---|---|---|---|---|
| | ATTTTCC | NNNNNNN | CGCATGT | Deg. MM | Promoter |
| | CATTCAATC | RWTTRWWTR | CTTTCATTT | Partial Deg. MM | Promoter |
| | TCAAGGAAGTAATTATCTACTTTTAC | WCAAGGAAKTAATTAWCWACWTTTWAC | ACAAGGAAATAATTA AC AAC ATTTAAC | Partial Deg. MM | Promoter |
| | TTCTAGTTAT TGGTCAT | TTCTAG----GGTCAT | TTCTAGGGTCAT | Deletion | Terminator |
| | CGA | AGA | AGA | MM | ORF |
| | AGG | CGG | CGG | MM | ORF |

FIG. 4D

SEQUENCE LISTING

```
<160> NUMBER OF SEQ ID NOS: 169

<210> SEQ ID NO 1
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 1
ggtaagcaca gaaagcaccc cggtggtaga ggtatggccg gtggtaaaca tcaccacaga      60
attaacatgg ataaatacca tccaggttat                                      90

<210> SEQ ID NO 2
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 2
ataacctgga tggtatttat ccatgttaat tctgtggtga tgtttaccac cggccatacc      60
tctaccaccg gggtgctttc tgtgcttacc                                      90

<210> SEQ ID NO 3
<211> LENGTH: 90
```

```
<212> TYPE: DNA
<213> ORGANISM: Artificial Sequence
<220> FEATURE:
<223> OTHER INFORMATION: synthetic polynucleotide

<400> SEQUENCE: 3
cgtggatgat gtggtctcta caggatctga cattattatt gttgaaagag gactatttgc    60
aaagggaagg gatgctaagg tagagggtga                                     90

<210> SEQ ID NO 4
<211> LENGTH: 89
<212> TYPE: DNA
<213> ORGANISM: Artificial Sequence
<220> FEATURE:
<223> OTHER INFORMATION: synthetic polynucleotide

<400> SEQUENCE: 4
tcaccctcta ccttagcatc ccttcccttt gcaaatagtc ctctttaaca ataataatgt    60
cagatcctgt agagaccaca tcatccacg                                      89

<210> SEQ ID NO 5
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 5
ggcagcaaac aggctcaaca ttaagacggt aatactagat gcttaaaatt ctcctgccaa    60
acaaataagc aactccaatg accacgttaa                                     90

<210> SEQ ID NO 6
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 6
ttaacgtggt cattggagtt gcttatttgt ttggcaggag aattttaagc atctagtatt    60
accgtcttaa tgttgagcct gtttgctgcc                                     90

<210> SEQ ID NO 7
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 7
ggtcccctag cgatagagca ctcgatcttc ccagaaaaag aggcagaagc agtagcagaa    60
caggccacac aatcgcaagt gattaacgtc                                     90

<210> SEQ ID NO 8
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 8
aatcatacgt cccaattgtc cccctcctaa tataccaact gttcaagaat ccatacttga    60
```

```
ttgttttgtc cgattttctt gttttcttg                                     90

<210> SEQ ID NO 9
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 9
ttacttgaag attctttagt gtaggaacat caacatgctc aatctaaatc gttagcacat   60 cacattttc agctagtttt tcgatatcaa                                    90

<210> SEQ ID NO 10
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 10
ctataccatt tttgattaaa tgctcttttt gaatatattt gtcttatatc aatctgattg   60
tttctggaga agggtaaatt tttaatttgg                                   90

<210> SEQ ID NO 11
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 11
atgccaaagt cctcgacttc aagacgaatg gaaaacccaa atctcatcca acattcaata   60
gggacgtctc actggcttgt tccacaggaa                                   90

<210> SEQ ID NO 12
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 12 attttcggc gtacaaagga cgatccttca gtacttccaa agcttacgga atcatttcct   60
tattctttac aacgaagtta cctcttccat                                   90

<210> SEQ ID NO 13
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 13
acataagtca caaatattgt ccttgtggat agtctctaca attggctaag aaaacactaa   60
accgttaaca gatctcacaa tcatgactgc                                   90

<210> SEQ ID NO 14
<211> LENGTH: 90
<212> TYPE: DNA
<213> ORGANISM: Artificial Sequence
<220> FEATURE:
<223> OTHER INFORMATION: synthetic polynucleotide
```

```
<400> SEQUENCE: 14
ccacaccaaa taccacaa ccgggaaaag atttgattgc attttatgcc aacaacttcg      60
ccttaagttg aacggagtcc ggaactctag                                      90

<210> SEQ ID NO 15
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 15
gagcttcaaa ttgagaagtg acgcaagcat caatggtata atgtcaagag ttgtgaggcc    60
ttggggcaat ttcgttaata agcaattccc                                      90

<210> SEQ ID NO 16
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 16
ccaatgctct ttcgcaagtt tctagctctt tatcttttgt atgttagtct ccaagaacat    60
ttagcataat ggcgttcgtt gtaatggtgg                                      90

<210> SEQ ID NO 17
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 17
cacattccgc catactggag gcaataatat ttatgtgacc tacttatctg ttaggtctag    60
actcttttcc atataagtac actgaggaac                                      90

<210> SEQ ID NO 18
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 18
tcaaattgat cctccaaata acagttcacg aaatgcaagt gaattcttga cctcggtatt    60
gcatagccca gtttctgtta atatgaaaaa                                      90

<210> SEQ ID NO 19
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 19
atttgatgtt tcatatttgt aaatagatag caaagtcgcc tcattgaatt cggagatgtt    60
acactcttta gggttaattt taaacattaa                                      90

<210> SEQ ID NO 20
```

```
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 20
ataattagcg tcaatcaata aaatatttgt aaaataggaa gcgaattccc gcagatgcca      60
gaataggtgg tgtataaggc aagaaaactt                                      90

<210> SEQ ID NO 21
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 21
ctgctgttta tctctttatc acttcagaaa actgacaaag aagaattctc cgaagaaagt      60
gaaaacgacg gaaacaagga gttgactata                                      90

<210> SEQ ID NO 22
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 22
catacgtccc aattgtcccc ctncctaata tacncaactg ttctnagaat ccatancttg      60
attgttnttg tccgatttc ttgtttttct                                       90

<210> SEQ ID NO 23
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
```

<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 23
cttgaagatt ctttagtgta ggnaacatca acantgctca atctncaatc gttagncaca    60
tcacatnttt tcagctagtt tttcgatatc                                      90

<210> SEQ ID NO 24
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 24 taccatttt gattaaatgc tcnttttga atantatttg tcttngtatc aatctngatt    60
gtttctngga gaagggtaaa tttttaattt                                      90

<210> SEQ ID NO 25
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)

```
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 25
ccaaagtcct cgacttcaag acngaatgga aaancccaaa tctcnttcca acattncaat    60
agggacngtc tcactggctt gttccacagg                                    90

<210> SEQ ID NO 26
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 26
tttcggcgta caaaggacga tcncttcagt actntccaaa gcttnccgga atcatnttcc    60
ttattcnttt acaacgaagt tacctcttcc                                    90

<210> SEQ ID NO 27
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
```

<220> FEATURE:
<221> NAME/KEY: misc_feature
<222> LOCATION: (67)..(67)
<223> OTHER INFORMATION: n is a, c, g, or t

<400> SEQUENCE: 27
taagtcacaa atattgtcct tgntggatag tctnctacaa ttggngtaag aaaacnacta    60
aaccgtntaa cagatctcac aatcatgact                                    90

<210> SEQ ID NO 28
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 28
caccaaatat accacaaccg ggnaaaagat ttgnattgca ttttnctgcc aacaancttc    60
gccttanagt tgaacggagt ccggaactct                                    90

<210> SEQ ID NO 29
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 29
cttcaaattg agaagtgacg canagcatca atgngtataa tgtcncagag ttgtgnaggc    60
cttgggngca atttcgttaa taagcaattc                                     90

<210> SEQ ID NO 30
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 30
atgctctttc gcaagtttct agnctcttta tctntttgta tgttntgtct ccaagnaaca    60
tttagcnata atggcgttcg ttgtaatggt                                     90

<210> SEQ ID NO 31
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 31
attccgccat actggaggca atnaatattt atgntgacct acttnttctg ttaggntcta    60
gactctnttt ccatataagt acactgagga                                     90

<210> SEQ ID NO 32
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(49)
<223> OTHER INFORMATION: n is a, c, g, or t

<400> SEQUENCE: 32
aaacctgtga gccgtcgcta ggaccttgtt gtgtgacgaa annnnnnnnt gcaatcaata    60
ggaagacagg aagtcgagcg tgtctgggtt                                    90

<210> SEQ ID NO 33
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 33
atgtaaatgt aagtttcacg aggttctact aaactaaacc acnnnnnngg ttagaagaaa    60
agagtgtgtg agaacaggct gttgttgtca                                    90

<210> SEQ ID NO 34
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 34
gctctggaga tcacagtggg catcatagca tgtggtacta aannnnnncc cgccattcca    60
gaaccttcga ttgcttgtta caaaacctgt                                    90

<210> SEQ ID NO 35
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(48)
<223> OTHER INFORMATION: n is a, c, g, or t

<400> SEQUENCE: 35
gaccaattta tgcaagttta tatatatgta aatgtaagtt tnnnnnnntt ctactaaact    60
aaaccacccc cttggttaga agaaaagagt                                    90

<210> SEQ ID NO 36
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (39)..(53)
<223> OTHER INFORMATION: n is a, c, g, or t

<400> SEQUENCE: 36
gtgggcatca tagcatgtgg tactaaaccc tttcccgcnn nnnnnnnnnn nnngattgct    60
tgttacaaaa cctgtgagcc gtcgctagga                                    90

<210> SEQ ID NO 37
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 37
gctcgaagaa ttggagagaa aaaagatgc ttttagaaaa tannnnnnat ttcccggaac     60
aatcaattat ttccatcaca atctttgaaa                                    90

<210> SEQ ID NO 38
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 38
gccaatgtac tatttatatt aaatggtgaa tgaagcaacg cannnnnnca aagaggttgg    60
agacatattc acccttacag caaacctttt                                    90

<210> SEQ ID NO 39
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C

```
<220> FEATURE:
<221> NAME/KEY: misc_feature
<222> LOCATION: (42)..(48)
<223> OTHER INFORMATION: n is a, c, g, or t

<400> SEQUENCE: 39
atattaaatg gtgaatgaag caacgcagta cctcaaagag gnnnnnnnca tattcaccct      60
tacagcaaac cttttttttc ctttactgga                                      90

<210> SEQ ID NO 40
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(48)
<223> OTHER INFORMATION: n is a, c, g, or t

<400> SEQUENCE: 40
ggattcaaaa ccacaagtac attcttcaac ggaaaagagt cnnnnnnncg gaaaagggac      60
ctcccgaaga cattagtctc ataattaagg                                      90

<210> SEQ ID NO 41
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (38)..(52)
<223> OTHER INFORMATION: n is a, c, g, or t

<400> SEQUENCE: 41
accttttttt tcagcttttt ccaaatcaga gagagcannn nnnnnnnnnn nntgtaagaa      60
aatgagatag atacatgcgt gggtcaattg                                      90

<210> SEQ ID NO 42
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 42
aaactaaaaa aaagactaac tataaaagta gaatttaaga agnnnnnnaa atagatttac      60
agaattacaa tcaatacctc ccgtctttat                                      90

<210> SEQ ID NO 43
<211> LENGTH: 90
<212> TYPE: DNA
<213> ORGANISM: Artificial Sequence
```

```
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 43
tgtttgttta tgtgtgttta ttcgaaacta agttcttggt gtnnnnnnac taaaaaaaag      60
actaactata aaagtagaat ttaagaagtt                                       90

<210> SEQ ID NO 44
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 44
ttacaatcaa tacctaccgt ctttatatac ttattagtca agnnnnnnaa taatttcagg      60
gaactggttt caacctttt tttcagcttt                                        90

<210> SEQ ID NO 45
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (43)..(48)
<223> OTHER INFORMATION: n is a, c, g, or t

<400> SEQUENCE: 45
catcactcca ttgaggttgt gcccgttttt tgcctgtttg tgnnnnnntt ctctgtagtt      60
gcgctaagag aatggaccta tgaactgatg                                       90

<210> SEQ ID NO 46
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (37)..(53)
<223> OTHER INFORMATION: n is a, c, g, or t

<400> SEQUENCE: 46 gtagggaat aatttcaggg aactggtttc aaccttnnnn nnnnnnnnn nnnaaatcag        60 agagagcaga aggtaataga aggtgtaaga                                       90
```

```
<210> SEQ ID NO 47
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (41)..(50)
<223> OTHER INFORMATION: n is a, c, g, or t

<400> SEQUENCE: 47
gagcaaacca gcattaacta aagatgataa aaataaaatt nnnnnnnnnn ccttaattgg      60
atatacaaaa atacactgga ggcacaaatc                                      90

<210> SEQ ID NO 48
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(48)
<223> OTHER INFORMATION: n is a, c, g, or t

<400> SEQUENCE: 48
agagaagagg agaaccgcac agaaagcagc agaaacagag cnnnnnnnca ttaactaaag      60
atgataaaaa taaaattagg taagaaacct                                      90

<210> SEQ ID NO 49
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(50)
<223> OTHER INFORMATION: n is a, c, g, or t

<400> SEQUENCE: 49
accaaatatg tatttcttgc attgaccaat ttatgcaagt tnnnnnnnnn gtaaatgtaa      60
gtttcacgag gttctactaa actaaaccac                                      90

<210> SEQ ID NO 50
<211> LENGTH: 89
<212> TYPE: DNA
<213> ORGANISM: Artificial Sequence
<220> FEATURE:
<223> OTHER INFORMATION: synthetic polynucleotide

<400> SEQUENCE: 50
accaaatatg tatttcttgc attgaccaat ttatgcaagt tywtwtatag taaatgtaag      60
tttcacgagg ttctactaaa ctaaaccac                                       89

<210> SEQ ID NO 51
```

```
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(49)
<223> OTHER INFORMATION: n is a, c, g, or t

<400> SEQUENCE: 51
agcgagaata attgacgttt gaaagagggc tgccaatgta cnnnnnnnnt taaatggtga      60
atgaagcaac gcagtacctc aaagaggttg                                      90

<210> SEQ ID NO 52
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 52
agcgagaata attgacgttt gaaagagggc tgccaatgta cywtwtatat taaatggtga      60
atgaagcaac gcagtacctc aaagaggttg                                      90

<210> SEQ ID NO 53
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (42)..(49)
<223> OTHER INFORMATION: n is a, c, g, or t

<400> SEQUENCE: 53
taagaaatag atttacagaa ttacaatcaa tacctaccgt cnnnnnnnnc ttattagtca      60
agtaggggaa taatttcagg gaactggttt                                      90

<210> SEQ ID NO 54
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 54
taagaaatag atttacagaa ttacaatcaa tacctaccgt cywtwtatac ttattagtca      60
agtaggggaa taatttcagg gaactggttt                                      90

<210> SEQ ID NO 55
<211> LENGTH: 90
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
```

<221> NAME/KEY: misc_feature
<222> LOCATION: (40)..(49)
<223> OTHER INFORMATION: n is a, c, g, or t

<400> SEQUENCE: 55
caagcaaact gagatgatct tcgacgtaaa aactcgctcn nnnnnnnnc gccatataag    60 cccatcggcg atgggggaca acacgaagaa                                    90

<210> SEQ ID NO 56
<211> LENGTH: 88
<212> TYPE: DNA
<213> ORGANISM: Artificial Sequence
<220> FEATURE:
<223> OTHER INFORMATION: synthetic polynucleotide

<400> SEQUENCE: 56
caagcaaact gagatgatct tcgacgtaaa aactcgctcy wtwtatacgc catataagcc    60
catcggcgat ggggacaac acgaagaa                                       88

<210> SEQ ID NO 57
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 57
gttgtaaaaa gtagataatt acttccttga wrawmwraa aaaararaaa aaraaarmaw    60
ctaagaactt gaaaaactac gaattagaaa                                    90

<210> SEQ ID NO 58
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 58 tttatttat ttagcagagg gtatagttat rmaawarmaa wwawwrwwam wrawwraawr    60
cctttataat ttcggtccga acaaagttag                                    90

<210> SEQ ID NO 59
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 59
atgtgtgttt attcgaaact aagttcttgg wrwwwwaaaa mwaaaaaaaa ramwaamwaw    60
aaaagtagaa tttaagaagt ttaagaaata                                    90

<210> SEQ ID NO 60
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 60
atataaacgt agttttgtat gtttctttga wwwraamwww waarwawama raraaaaaaa    60
ccgatcaaag aaaactaaag tataatgagg                                    90

<210> SEQ ID NO 61
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 61
tcttgttctt ttcccatttg ttttatattt kttktwwwww ktwkwtwwtt wyttyyttkw      60
tgatctgtaa aaaagagaaa aagaaagcat                                      90

<210> SEQ ID NO 62
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 62
attgctgtga ggatgttcgc gtaatccatt tttwttttwt ttwkywkwkk ktwtwkttwt      60
gcaatagcaa ttattgttac tgattgaatg                                      90

<210> SEQ ID NO 63
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 63
atatgcgaga gccgtcattt ttgtttgttt wtktktkttt wttykwwwyt wwkttyttkk      60
tgttttaaaa ctaaaaaaaa gactaactat                                      90

<210> SEQ ID NO 64
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 64
gttttcacca attggtccat ttattaattg wtwtwwwykt wkttttktwt ktttyttkw       60 tttgaacttt taagtataca gagaaaaaaa                                      90

<210> SEQ ID NO 65
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 65
tttcacgagg ttctactaaa ctaaaccacc ccctttttt tttttttttt tttttggtta      60
gaagaaaaga gtgtgtgaga acaggctgtt                                      90

<210> SEQ ID NO 66
<211> LENGTH: 90
<212> TYPE: DNA
<213> ORGANISM: Artificial Sequence
<220> FEATURE:
<223> OTHER INFORMATION: synthetic polynucleotide

```
<400> SEQUENCE: 66
aatgaagcaa cgcagtacct caaagaggtt ggagattttt tttttttttt tttttcatat    60
tcacccttac agcaaacctt tttttccctt                                     90

<210> SEQ ID NO 67
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 67
tttccaaatc agagagagca gaaggtaata gaaggttttt tttttttttt tttttgtaa    60 gaaaatgaga tagatacatg cgtgggtcaa                                    90

<210> SEQ ID NO 68
<211> LENGTH: 89
<212> TYPE: DNA
<213> ORGANISM: Artificial Sequence
<220> FEATURE:
<223> OTHER INFORMATION: synthetic polynucleotide

<400> SEQUENCE: 68
aactaaagat gataaaaata aaattaggta agaaattttt tttttttttt tttttcctta    60
attggatata caaaaataca ctggaggca                                     89

<210> SEQ ID NO 69
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 69
agtaaactcg agtggaattg ctgtgaggat gttcgcgtaa tccactttta ttttatttag    60
cagagggtat agttatcctt tataatttcg                                    90

<210> SEQ ID NO 70
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 70
tctgcggaat cccgtaaatt agatgggcca caggcgaccc acgccggagg accgatgaat    60
cctccacatc gtccattaat aagctagcgg                                    90

<210> SEQ ID NO 71
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 71
tcttgacatc caaccaatag ttgaaagcct cgatgagttg tgatctaatt tcttttccag    60
ggttctttcc taggtagtga tacggttcaa                                    90

<210> SEQ ID NO 72
<211> LENGTH: 90
```

```
<212> TYPE: DNA
<213> ORGANISM: Artificial Sequence
<220> FEATURE:
<223> OTHER INFORMATION: synthetic polynucleotide

<400> SEQUENCE: 72
agttgtgatc gaatttcttt tccagggttc tttcctaggt agtgactacg gttcaaggag    60
cacgatatca tcctgaggag taaactcgag                                     90

<210> SEQ ID NO 73
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 73
ccacgatgat agctgtgggt ttatcctgat cttgttcttt tcccacttgt tttatatttg    60
ttgtaaaaag tagataatta cttccttgat                                     90

<210> SEQ ID NO 74
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 74
tttgacccat gtacatcact gcaaacgaga agactcttcg taatcggtcg gtcttgaaat    60
atcgacaaac tcttgtccag atagactcga                                     90

<210> SEQ ID NO 75
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 75
gcaagagcag caaactgggc ccctgatcga atcgataacc atctctctcg attaaagagc    60
atcgacctcc ggagtagtcg ttcttctcga                                     90

<210> SEQ ID NO 76
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 76
tccggagtag tcgttcttct cgaacaccgt gacctggaaa ccttcattta gcaagacgag    60
cggcagtggc gattccaccg ataccacatc                                     90

<210> SEQ ID NO 77
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 77
ggagagtata gatcagatgg atctggtaat atgcgagagc cgtcactttt gtttgtttat    60
```
gtgtgtttat tcgaaactaa gttcttggtg                                         90

<210> SEQ ID NO 78
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 78
cggacgatct agtcttggga agcgcgagag atgggagaag gtgccgagtt gccaagacgt        60
agaccaagcc ggtgattacg gtttgaatga                                         90

<210> SEQ ID NO 79
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 79
gatacaccgt cgggatcatg attgctgcaa tagttgactt tgctctgcca cttttccaat        60
cgaaagcata ttcgcctgat aatgctgcca                                         90

<210> SEQ ID NO 80
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 80
gctgatggat atgtccatgc gccatttctg atgatccatg agtcctcatg gtgtggttgc        60
actaaacgca ataaatacga ggatcgatat                                         90

<210> SEQ ID NO 81
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 81
tccgctgatg gatatgtcca tgcgccattt ctgatgatcc atgagcccca tggtgtggtt        60
gcactaaacg caataaatac gaggatcgat                                         90

<210> SEQ ID NO 82
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 82
agtaaaagac ttcttggtga cttcagtttt caccaattgg tccacttatt aattgatata        60
aacgtagttt tgtatgtttc tttgatttga                                         90

<210> SEQ ID NO 83
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 83
cagatgctaa tacaggagct tctgccaaaa ttgaaagagc cttccgacgt accgcaaccg    60
ctctcgtagt atcacctaat tttttctcca                                    90

<210> SEQ ID NO 84
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 84
aattcttcta aaggacgtat tttcttatcc aagctttcaa tatctctgga atcatcttcc    60
tcactagatg atgaaggtcc tgatgagctc                                    90

<210> SEQ ID NO 85
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 85
acgtattttc ttatccaagc tttcaatatc gcgggaatca tcttcactca ctagatgatg    60
aaggtcctga tgagctcgat tgcgcagatg                                    90

<210> SEQ ID NO 86
<211> LENGTH: 88
<212> TYPE: DNA
<213> ORGANISM: Artificial Sequence
<220> FEATURE:
<223> OTHER INFORMATION: synthetic polynucleotide

<400> SEQUENCE: 86
atataaatta taaactactc attcgtatat gaaaatacgt gtaataattg aatagtcgca    60
taccctgaat caaaaatcaa attttcct                                      88

<210> SEQ ID NO 87
<211> LENGTH: 87
<212> TYPE: DNA
<213> ORGANISM: Artificial Sequence
<220> FEATURE:
<223> OTHER INFORMATION: synthetic polynucleotide

<400> SEQUENCE: 87
tagagcaaaa gttgggaaaa tagaaaatag aaaacagaaa agaataagag cgaaattta    60 tctcattacg aaattttct catttaa                                        87

<210> SEQ ID NO 88
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 88
aaatatagaa attattttct ttattttac cattttaaac atgaccctag aagatacata    60
aaagaacaaa tgaactttat acatattctc                                    90

<210> SEQ ID NO 89

<211> LENGTH: 89
<212> TYPE: DNA
<213> ORGANISM: Artificial Sequence
<220> FEATURE:
<223> OTHER INFORMATION: synthetic polynucleotide

<400> SEQUENCE: 89
acttcgaaat ctatgacgat tatattatac actaaaatat agaaatttac cattttaaac     60
atgaccaata actagaagat acataaaag                                       89

<210> SEQ ID NO 90
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 90
aatgtaagtt tcacgaggtt ctactaaact aaaccaccgg aggagagtct tccgtggtta     60
gaagaaaaga gtgtgtgaga acaggctgtt                                      90

<210> SEQ ID NO 91
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 91
ggagatcaca gtgggcatca tagcatgtgg tactaaacgg aggagagtct tccgtcccgc     60
cattccagaa ccttcgattg cttgttacaa                                      90

<210> SEQ ID NO 92
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 92
ggggcatcat agcatgtggt actaaaccct ttcccgccgg aggagagtct tccgtgattg     60
cttgttacaa aacctgtgag ccgtcgctag                                      90

<210> SEQ ID NO 93
<211> LENGTH: 89
<212> TYPE: DNA
<213> ORGANISM: Artificial Sequence
<220> FEATURE:
<223> OTHER INFORMATION: synthetic polynucleotide

<400> SEQUENCE: 93
aagaattgga gagaaaaaaa gatgctttta gaaaatacgg aggagagtct tccgtatttc     60
ccggaacaat caattatttc catcacaat                                       89

<210> SEQ ID NO 94
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 94 gtactatttta tattaaatgg tgaatgaagc aacgcacgga ggagagtctt ccgtcaaaga     60
ggttggagac atattcaccc ttacagcaaa                                       90

<210> SEQ ID NO 95
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 95
aaatggtgaa tgaagcaacg cagtacctca aagaggcgga ggagagtctt ccgtcatatt      60 caccottaca gcaaaccttt tttttccttt                                       90

<210> SEQ ID NO 96
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 96
tcaataccta ccgtctttat atacttatta gtcaagcgga ggagagtctt ccgtaataat      60
ttcagggaac tggtttcaac ctttttttc                                        90

<210> SEQ ID NO 97
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 97
ctccattgag gttgtgcccg ttttttgcct gtttgtgcgg aggagagtct tccgtttctc      60
tgtagttgcg ctaagagaat ggacctatga                                       90

<210> SEQ ID NO 98
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 98 gtagggaat aatttcaggg aactggtttc aaccttcgga ggagagtctt ccgtaaatca       60
gagagagcag aaggtaatag aaggtgtaag                                       90

<210> SEQ ID NO 99
<211> LENGTH: 90
<212> TYPE: DNA
<213> ORGANISM: Artificial Sequence
<220> FEATURE:
<223> OTHER INFORMATION: synthetic polynucleotide

<400> SEQUENCE: 99
aaaccagcat taactaaaga tgataaaaat aaaattcgga ggagagtctt ccgtccttaa      60
ttggatatac aaaaatacac tggaggcaca                                       90

<210> SEQ ID NO 100
<211> LENGTH: 90
<212> TYPE: DNA
<213> ORGANISM: Artificial Sequence
<220> FEATURE:

<223> OTHER INFORMATION: synthetic polynucleotide

<400> SEQUENCE: 100
agaggagaac cgcacagaaa gcagcagaaa cagagccgga ggagagtctt ccgtcattaa    60
ctaaagatga taaaaataaa attaggtaag                                    90

<210> SEQ ID NO 101
<211> LENGTH: 15
<212> TYPE: DNA
<213> ORGANISM: Artificial Sequence
<220> FEATURE:
<223> OTHER INFORMATION: synthetic polynucleotide

<400> SEQUENCE: 101
gaaggttctg gaatg                                                    15

<210> SEQ ID NO 102
<211> LENGTH: 15
<212> TYPE: DNA
<213> ORGANISM: Artificial Sequence
<220> FEATURE:
<223> OTHER INFORMATION: synthetic polynucleotide

<400> SEQUENCE: 102
ccttctatta ccttc                                                    15

<210> SEQ ID NO 103
<211> LENGTH: 17
<212> TYPE: DNA
<213> ORGANISM: Artificial Sequence
<220> FEATURE:
<223> OTHER INFORMATION: synthetic polynucleotide

<400> SEQUENCE: 103
ggaaaaagct gaaaaaa                                                  17

<210> SEQ ID NO 104
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 104
tttcttacct                                                          10

<210> SEQ ID NO 105
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 105
tatatatata                                                          10

<210> SEQ ID NO 106
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 106
atgctttctt tttctctttt ttacagatca                                    30

<210> SEQ ID NO 107
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 107
cattcaatca gtaacaataa ttgctattgc                                      30

<210> SEQ ID NO 108
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 108
atagttagtc tttttttag ttttaaaaca                                       30

<210> SEQ ID NO 109
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 109
ctctgtatac ttaaaagttc aaa                                             23

<210> SEQ ID NO 110
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 110
tcaaggaagt aattatctac tttttacaac a                                    31

<210> SEQ ID NO 111
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 111
taactatacc ctctgctaaa taaaat                                          26

<210> SEQ ID NO 112
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 112
ccaagaactt agtttcgaat aaacacacat a                                    31

<210> SEQ ID NO 113
<211> LENGTH: 30
<212> TYPE: DNA
<213> ORGANISM: Artificial Sequence
<220> FEATURE:

<223> OTHER INFORMATION: synthetic polynucleotide

<400> SEQUENCE: 113
tcaaagaaac atacaaaact acgtttatat                                          30

<210> SEQ ID NO 114
<211> LENGTH: 11
<212> TYPE: DNA
<213> ORGANISM: Artificial Sequence
<220> FEATURE:
<223> OTHER INFORMATION: synthetic polynucleotide

<400> SEQUENCE: 114
tagttattgg t                                                              11

<210> SEQ ID NO 115
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 115
aaaaataaag aaaataattt                                                     20

<210> SEQ ID NO 116
<211> LENGTH: 16
<212> TYPE: DNA
<213> ORGANISM: Artificial Sequence
<220> FEATURE:
<223> OTHER INFORMATION: synthetic polynucleotide

<400> SEQUENCE: 116
gaaggttctg gaatgg                                                         16

<210> SEQ ID NO 117
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 117
ggaaaaagct gaaaaaaaag g                                                   21

<210> SEQ ID NO 118
<211> LENGTH: 12
<212> TYPE: DNA
<213> ORGANISM: Artificial Sequence
<220> FEATURE:
<223> OTHER INFORMATION: synthetic polynucleotide

<400> SEQUENCE: 118
tttcttacct aa                                                             12

<210> SEQ ID NO 119
<211> LENGTH: 15
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (1)..(15)

```
<223> OTHER INFORMATION: n is a, c, g, or t

<400> SEQUENCE: 119
nnnnnnnnnn nnnnn                                              15

<210> SEQ ID NO 120
<211> LENGTH: 17
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (1)..(17)
<223> OTHER INFORMATION: n is a, c, g, or t

<400> SEQUENCE: 120
nnnnnnnnnn nnnnnnn                                            17

<210> SEQ ID NO 121
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<223> OTHER INFORMATION: 'N' = A,T,G, or C
<220> FEATURE:
<221> NAME/KEY: misc_feature
<222> LOCATION: (1)..(10)
<223> OTHER INFORMATION: n is a, c, g, or t

<400> SEQUENCE: 121 nnnnnnnnnn                                                    10

<210> SEQ ID NO 122
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 122
wtkytttytt tttytytttt ttwywkwtyw                              30

<210> SEQ ID NO 123
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 123
ywttywwtyw ktwwywwtww ttkytwttky                              30

<210> SEQ ID NO 124
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 124
wtwkttwkty ttttttttwk ttttwwwwyw                              30
```

```
<210> SEQ ID NO 125
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 125
ytytktwtwy ttwwwwktty www                                            23

<210> SEQ ID NO 126
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 126
wmaarraarw aawwawmwam wwwwwamaam                                     30

<210> SEQ ID NO 127
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 127
waamwawamm mwmwrmwaaa waaaaw                                         26

<210> SEQ ID NO 128
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 128
mmaaraamww arwwwmraaw aaamamamaw                                     30

<210> SEQ ID NO 129
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 129
wmaaaraaam awamaaaamw amrwwwawaw                                     30

<210> SEQ ID NO 130
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 130
caaaaaaaaa aaaaaaaaa aaaggg                                          26

<210> SEQ ID NO 131
<211> LENGTH: 27
<212> TYPE: DNA
<213> ORGANISM: Artificial Sequence
<220> FEATURE:
```

```
<223> OTHER INFORMATION: synthetic polynucleotide

<400> SEQUENCE: 131
tatgaaaaaa aaaaaaaaaa aaaatct                                          27

<210> SEQ ID NO 132
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 132
acaaaaaaaa aaaaaaaaaa aaacct                                           26

<210> SEQ ID NO 133
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 133
aggaaaaaaa aaaaaaaaaa aaattt                                           26

<210> SEQ ID NO 134
<211> LENGTH: 11
<212> TYPE: DNA
<213> ORGANISM: Artificial Sequence
<220> FEATURE:
<223> OTHER INFORMATION: synthetic polynucleotide

<400> SEQUENCE: 134
caattattac a                                                           11

<210> SEQ ID NO 135
<211> LENGTH: 11
<212> TYPE: DNA
<213> ORGANISM: Artificial Sequence
<220> FEATURE:
<223> OTHER INFORMATION: synthetic polynucleotide

<400> SEQUENCE: 135
ctcttattct t                                                           11

<210> SEQ ID NO 136
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 136
acggaagact ctcctccgg                                                   19

<210> SEQ ID NO 137
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 137
gacggaagac tctcctccgt                                                  20
```

-continued

```
<210> SEQ ID NO 138
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 138
tcacggaaga ctctcctccg g                                              21

<210> SEQ ID NO 139
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 139
gacggaagac tctcctccg                                                 19

<210> SEQ ID NO 140
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 140
attacggaag actctcctcc gctt                                           24

<210> SEQ ID NO 141
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 141
aaacggaaga ctctcctccg c                                              21

<210> SEQ ID NO 142
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 142
ttacggaaga ctctcctccg aa                                             22

<210> SEQ ID NO 143
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 143
aggacggaag actctcct                                                  18

<210> SEQ ID NO 144
<211> LENGTH: 21
<212> TYPE: DNA
<213> ORGANISM: Artificial Sequence
<220> FEATURE:
<223> OTHER INFORMATION: synthetic polynucleotide
```

```
<400> SEQUENCE: 144
gacggaagac tctcctccgg c                                              21

<210> SEQ ID NO 145
<211> LENGTH: 90
<212> TYPE: DNA
<213> ORGANISM: Artificial Sequence
<220> FEATURE:
<223> OTHER INFORMATION: synthetic polynucleotdie
<220> FEATURE:
<221> NAME/KEY: misc_feature
<222> LOCATION: (44)..(44)
<223> OTHER INFORMATION: n is a, c, g, or t

<400> SEQUENCE: 145
aaacctgtga gccgtcgcta ggaccttgtt gtgtgacgaa attngwagct gcaatcaata    60
ggaagacagg aagtcgagcg tgtctgggtt                                     90

<210> SEQ ID NO 146
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 146
atgtaaatgt aagtttcacg aggttctact aaactaaacc acccyyttgg ttagaagaaa    60
agagtgtgtg agaacaggct gttgttgtca                                     90

<210> SEQ ID NO 147
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 147
gctctggaga tcacagtggg catcatagca tgtggtacta aaccyyttcc cgccattcca    60
gaaccttcga ttgcttgtta caaaacctgt                                     90

<210> SEQ ID NO 148
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 148
gaccaattta tgcaagttta tatatatgta aatgtaagtt tcwcgwggtt ctactaaact    60
aaaccacccc cttggttaga agaaaagagt                                     90

<210> SEQ ID NO 149
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 149
gtgggcatca tagcatgtgg tactaaaccc tttcccgcca yyccagrrcc ttcgattgct    60
tgttacaaaa cctgtgagcc gtcgctagga                                     90
```

```
<210> SEQ ID NO 150
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 150
gctcgaagaa ttggagagaa aaaaagatgc ttttagaaaa targacmcat ttcccggaac      60
aatcaattat ttccatcaca atctttgaaa                                      90

<210> SEQ ID NO 151
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 151
gccaatgtac tatttatatt aaatggtgaa tgaagcaacg cagkaccyca aagaggttgg      60
agacatattc acccttacag caaaccttt                                       90

<210> SEQ ID NO 152
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 152
atattaaatg gtgaatgaag caacgcagta cctcaaagag gttyyrgaca tattcaccct      60
tacagcaaac cttttttttc ctttactgga                                      90

<210> SEQ ID NO 153
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 153
ggattcaaaa ccacaagtac attcttcaac ggaaaagagt cggawaatcg gaaaagggac      60
ctcccgaaga cattagtctc ataattaagg                                      90

<210> SEQ ID NO 154
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 154 acctttttt tcagcttttt ccaaatcaga gagagcagaa ggtrrtagaa ggtgtaagaa       60
aatgagatag atacatgcgt gggtcaattg                                      90

<210> SEQ ID NO 155
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 155
```
aaactaaaaa aaagactaac tataaaagta gaatttaaga agwwwwwgaa atagatttac    60
agaattacaa tcaataccta ccgtctttat                                    90

<210> SEQ ID NO 156
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 156
tgtttgttta tgtgtgttta ttcgaaacta agttcttggt gtwwwwwac taaaaaaaag    60 actaactata aaagtagaat ttaagaagtt                                    90

<210> SEQ ID NO 157
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 157
ttacaatcaa tacctaccgt ctttatatac ttattagtca agtarrrraa taatttcagg    60
gaactggttt caaccttttt tttcagcttt                                    90

<210> SEQ ID NO 158
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 158
catcactcca ttgaggttgt gcccgttttt tgcctgtttg tgyyyytgtt ctctgtagtt    60
gcgctaagag aatggaccta tgaactgatg                                    90

<210> SEQ ID NO 159
<211> LENGTH: 91
<212> TYPE: DNA
<213> ORGANISM: Artificial Sequence
<220> FEATURE:
<223> OTHER INFORMATION: synthetic polynucleotdie

<400> SEQUENCE: 159 gtagggaat aatttcaggg aactggtttc aaccttwwww wwcagcwwww wtccaaatca     60
gagagagcag aaggtaatag aaggtgtaag a                                  91

<210> SEQ ID NO 160
<211> LENGTH: 90
<212> TYPE: DNA
<213> ORGANISM: Artificial Sequence
<220> FEATURE:
<223> OTHER INFORMATION: synthetic polynucleotdie

<400> SEQUENCE: 160
gagcaaacca gcattaacta aagatgataa aaataaaatt aggtwwgwww ccttaattgg    60
atatacaaaa atacactgga ggcacaaatc                                    90

<210> SEQ ID NO 161
<211> LENGTH: 90
<212> TYPE: DNA
<213> ORGANISM: Artificial Sequence

```
<220> FEATURE:
<223> OTHER INFORMATION: synthetic polynucleotdie

<400> SEQUENCE: 161
agagaagagg agaaccgcac agaaagcagc agaaacagag caaayyrrca ttaactaaag    60
atgataaaaa taaaattagg taagaaacct                                    90

<210> SEQ ID NO 162
<211> LENGTH: 15
<212> TYPE: DNA
<213> ORGANISM: Artificial Sequence
<220> FEATURE:
<223> OTHER INFORMATION: synthetic polynucleotdie

<400> SEQUENCE: 162
ccttctayya ccttc                                                    15

<210> SEQ ID NO 163
<211> LENGTH: 18
<212> TYPE: DNA
<213> ORGANISM: Artificial Sequence
<220> FEATURE:
<223> OTHER INFORMATION: synthetic polynucleotdie

<400> SEQUENCE: 163
ggawwwwwgc tgwwwwww                                                 18

<210> SEQ ID NO 164
<211> LENGTH: 10
<212> TYPE: DNA
<213> ORGANISM: Artificial Sequence
<220> FEATURE:
<223> OTHER INFORMATION: synthetic polynucleotdie

<400> SEQUENCE: 164 wwwcwwacct                                                          10

<210> SEQ ID NO 165
<211> LENGTH: 12
<212> TYPE: DNA
<213> ORGANISM: Artificial Sequence
<220> FEATURE:
<223> OTHER INFORMATION: synthetic polynucleotdie

<400> SEQUENCE: 165
caattattta ca                                                       12

<210> SEQ ID NO 166
<211> LENGTH: 27
<212> TYPE: DNA
<213> ORGANISM: Artificial Sequence
<220> FEATURE:
<223> OTHER INFORMATION: synthetic polynucleotdie

<400> SEQUENCE: 166
wcaaggaakt aattawcwac wtttwac                                       27

<210> SEQ ID NO 167
<211> LENGTH: 27
<212> TYPE: DNA
<213> ORGANISM: Artificial Sequence
<220> FEATURE:
<223> OTHER INFORMATION: synthetic polynucleotdie

<400> SEQUENCE: 167
```

```
acaaggaaat aattaacaac atttaac                                                    27

<210> SEQ ID NO 168
<211> LENGTH: 17
<212> TYPE: DNA
<213> ORGANISM: Artificial Sequence
<220> FEATURE:
<223> OTHER INFORMATION: synthetic polynucleotdie

<400> SEQUENCE: 168
ttctagttat tggtcat                                                               17

<210> SEQ ID NO 169
<211> LENGTH: 12
<212> TYPE: DNA
<213> ORGANISM: Artificial Sequence
<220> FEATURE:
<223> OTHER INFORMATION: synthetic polynucleotdie

<400> SEQUENCE: 169
ttctagggtc at                                                                    12
```

MULTIPLEX GENOME ENGINEERING IN EUKARYOTES

CROSS-REFERENCE TO RELATED APPLICATIONS

This application is a National Phase application under 35 U.S.C. 371 of PCT/US2017/029922 filed Apr. 27, 2017 entitled "MULTIPLEX GENOME ENGINEERING IN EUKARYOTES," which claims the benefit of and priority to U.S. Ser. No. 62/328,507 filed Apr. 27, 2016 which are incorporated herein by reference in their entirety.

STATEMENT REGARDING FEDERALLY SPONSORED RESEARCH

This invention was made with government support under 1122492 awarded by National Science Foundation and N66001-12-C-4020 awarded by Defense Advanced Research Projects Agency. The government has certain rights in the invention.

REFERENCE TO SEQUENCE LISTING

The Sequence Listing submitted as a text file named "YU_6997_PCT_ST25.txt," created on Apr. 27, 2017, and having a size of 50,495 bytes is hereby incorporated by reference pursuant to 37 C.F.R. § 1.52(e)(5).

FIELD OF THE INVENTION

This application is generally in the field of gene modification, and more specifically methods of modifying a genome without breaking the backbone of the target DNA.

BACKGROUND OF THE INVENTION

Most eukaryotic genome editing technologies—zinc finger nucleases (ZFNs), transcription activator-like effector nucleases (TALENs), and CRISPR-associated endonuclease Cas9 (CRISPR-Cas9)—generate DNA double-strand breaks (DSBs) at targeted loci to introduce genomic modifications (Doudna and Charpentier, 2014; Gaj et al., 2013). Although ZFNs and TALENs recognize specific DNA sequences through protein-DNA interactions and use the FokI nuclease domain to introduce DSBs at genomic loci, construction of functional ZFNs and TALENs with desired DNA specificity remains laborious, costly, and primarily limited to modifications at a single genetic locus. CRISPR-Cas9 has been broadly adopted for multiplexed targeting of genomic modifications because the CRISPR nuclease Cas9 uses a short guide RNA (gRNA) to recognize the target DNA via Watson-Crick base-pairing and has been shown to function in many organisms (Cong, L., et al., Science, 339:819-823 (2013); Jinek, et al., Elife 2, e00471 (2013); Mali, et al., Science, 339:823-826 (2013)). In this regard, CRISPR-Cas9 is highly suited for gene disruption applications by non-homologous end joining (NHEJ) (Yang, et al., Science, 350:1101-1104 (2015)), and gene editing at one or more sites with homology directed repair (HDR) (Doudna, et al., Science, 346:1258096 (2014)).

For applications that require multisite editing or precise base-pair level genome modifications by HDR, the DSB mechanism is limiting for three key reasons. First, cleaving the genome is cytotoxic, and cell lethality is magnified when DSBs are introduced across multiple target sites (Jakociunas, et al., Metab Eng, 28:213-222 (2015)). Second, in eukaryotes most single base-pair HDR changes introduced by DSB repair are subject to additional unwanted insertions or deletions (indels) resulting from NHEJ (Inui, et al., Sci Rep, 4:5396 (2014)). These additional mutations result from high tolerance of the targeted nuclease (i.e., Cas9:gRNA) to mismatches in the DSB target which can lead to additional cleavage even after HDR editing has occurred (Fu, et al., Nature Biotechnology, 31:822-826 (2013)). For single base-pair HDR, the inclusion of blocking mutations in the donor DNA is typically required to mask the genomic target site from further cutting by the Cas9:Gma (Horwitz, et al., Cell Syst, 1:88-96 (2015); Paquet, et al., Nature, 533:125-129 (2016)). For many types of genetic elements (e.g., promoters, ncRNAs), the exact DNA sequence dictates function such that additional blocking mutations are often prohibitive.

Despite the highly improved stringencies of engineered Cas9 variants, mismatches are still tolerated for many non-standard target sites with repetitive regions (Tsai, et al., Nat Rev Genet, 17:300-312 (2016)). Third, the inefficiency of generating targeted single base-pair edits with DSBs limits the ability to simultaneously modify many loci in a single cell or across a population to produce combinatorial genetic diversity for exploration of vast genomic landscapes. Efficient DNA base editing without a DSB has been reported using Cas9-guided deamination, but this technique is limited to specific C→T or G→A mutations in an imprecise window of several base-pairs (Komor, et al., Nature (2016)). Thus, creating precise edits at single base-pair resolution in a single-step at any genomic sequence remains a defining challenge for eukaryotic genome engineering technologies.

For the application of creating targeted genomic diversity with high DNA sequence resolution, ablation of the target-site sequence is often not feasible without perturbing surrounding sequence context. Therefore developing high efficiency genome mutagenic methods that do not rely on breaking the DNA backbone could serve as a powerful alternative to generate multi-site modifications of the genome. Such a tool would be useful for modification of genetic elements where precise sequence context is important such as promoters, open reading frames with strong codon biases, terminator elements, splice sites, enhancers, and other types of global regulatory elements. Furthermore, precise editing of eukaryotic genomes across many positions at once is a challenge that if solved would allow for exploration of genomic sequence space at time-scales feasible for laboratory studies.

Prior work in Escherichia coli demonstrated that targeted chromosomal modifications could be introduced without DSBs using synthetic ssDNA oligodeoxynucleotides (ssODNs) complementary to the lagging strand of the replicating chromosome at high efficiencies (>10%) (Costantino, et al., Proceedings of the National Academy of Sciences of the United States of America, 100:15748-15753 (2003); Li, et al., Nucleic Acids Research, 31:6674-6687 (2003)). With the advent of multiplex automated genome engineering (MAGE), this approach was enhanced to generate multi-site gene modifications with base-pair precision at increased efficiencies (>30%) and used for pathway diversification (Wang, et al., Nature, 460:894-898 (2009)), whole genomic recoding (Lajoie, et al., Science, 342:357-360 (2013)), and molecular evolution of proteins (Amiram, et al., Nature Biotechnology, 33:1272-1279 (2015)). Although homologous recombination (HR) of ssODNs was developed ~30 years ago in S. cerevisiae (Moerschell, et al., Methods in Enzymology, 194:362-369 (1991); Moerschell, et al., J Biol Chem, 265:19638-19643 (1990); Moerschell, et al., Proceedings of the National Academy of Sciences of the United States of America, 85:524-528 (1988); Yamamoto, et al., Yeast, 8:935-948 (1992a); Yamamoto, et al., Genetics, 131: 811-819 (1992b)), low gene targeting efficiencies (~0.0001-0.001%) limited the scope of applications to single locus modifications requiring counter-selectable markers (Storici, et al., Genet Eng (NY), 25:189-207 (2003)). The mechanism of ssODN incorporation in eukaryotic cells is less precisely defined than in *E. coli* and likely involves several parameters, which include direction of DNA replication (Rodriguez, et al., *PloS One*, 7:e42905 (2012); Yamamoto, et al., Genetics, 131:811-819 (1992b)), cell-cycle phase (Engstrom, et al., *BMC Mol Biol*, 8:9 (2007)), transcription (Brachman, et al., *J Cell Sci*, 117:3867-3874 (2004)), DNA mismatch repair (MMR) (Kow, et al., *Proceedings of the National Academy of Sciences of the United States of America*, 104:11352-11357 (2007)), and HR (Liu, et al., *Nucleic Acids Research*, 32:2093-2101 (2004)). Efforts to develop an analogous MAGE technology in *S. cerevisiae* have focused on overexpression of HR factors Rad51 and Rad54 in MMR deficient strains and resulted in moderately enhanced allelic replacement frequencies (ARF) (~0.1-2%) (DiCarlo, et al., *ACS Synth Biol*, 2:741-749 (2013); Liu, et al., *Nucleic Acids Research*, 32:2093-2101 (2004)). Thus, no clear method has been established in eukaryotes for precise, multisite genome modification with ssODNs that approaches efficiencies attained in *E. coli* (>30%).

Thus, it is an object of the invention to provide compositions and methods for genome modification without breaking the backbone of the target DNA.

It is a further object of the invention to provide compositions and methods of genome modification suitable for large-scale genomic modifications.

It is also an object of the invention provide compositions and methods for genome modification that are suitable for use in eukaryotes.

SUMMARY OF THE INVENTION

Compositions and methods for gene editing are provided. The methods employ an oligo-based annealing mechanism that is rooted in the process of DNA replication rather than homologous recombination (HR). Oligo incorporation efficiencies are comparable and often exceed those of CRISPR/cas9 editing without the need for double strand breaks (DSBs). By relying on the multiplex annealing of oligos rather than DSBs the process is highly scalable across a genomic region of interest and can generate many scar-less modifications of a chromosome simultaneously. Combinatorial genomic diversity can be generated across a population of cells in a single transformation event; genomic landscapes can be traversed through successive iterations of the process, and genome-wide changes can be massively parallelized and amplified through systematic strain mating.

The Examples below exemplify the strategy by highly multiplexed combinatorial genome engineering of the model eukaryote and industrial chassis organism *S. cerevisiae*. After showing that the method can incorporate single oligos at high efficiencies, an unprecedented ability to incorporate multiple oligos at once was demonstrated, and a cycling protocol to iteratively introduce oligonucleotides for generating genetic diversity at genetic regions of interest was developed. Many sites can be targeted simultaneously on a chromosome. In the experiments described below, cells with up 42 designed mutations in a single chromosome after only 3 cycles. Many of the specific types of mutations designed and observed were extremely high resolution mutations (single base-pair changes) that could not have been made using the CRISPR/cas9 system without the introduction of additional sequences to destroy the target sites. Thus, the method provides highly precise editing at many sites without introducing unwanted additional scar sequences.

The methods induce genome modification by annealing oligos at the replication fork in which synthetic single stranded DNA (ssDNA) oligonucleotides are incorporated into the genome, by a method/process developed for achieving 100-fold higher efficiencies than the current state of the art of oligonucleotide-based genome editing technologies in eukaryotes, and can be carried out without DSBs. Mutation efficacy can be increased by reducing RAD51 expression to drive the mechanism away from strand invasion/homologous recombination, deletion/impairment of DNA repair proteins such as MSH2, or a combination thereof For example, a method for preparing a library of mutant eukaryotic cells can include (i) transfecting or transforming a population of host cells with (a) an oligonucleotide that can introduce one or more mutations into a selectable marker when incorporated into a cell's genome by replication fork annealing and (b) one or more oligonucleotides that can introduce one or more mutations into a target region when incorporated into a cell's genome by replication fork annealing; and (ii) selecting mutant cells that have a mutation in the selectable marker.

The target region and the selectable marker can be separated by, for example, 4, 3, 2, 1, or 0 origins of replication. The target region can range from, for example, 1 base pair to 1 million, 2 million, 5 million, 10 million, 100 million, or more base pairs in either direction from the origin of replication closest to the selectable marker.

The selectable marker can be a counter-selectable marker (e.g., URA3) and mutant cells can be selected by culturing the transfected cells in presences of a compound that kills cells expressing the un-mutated selectable marker (e.g., 5FOA). The one or more oligonucleotides of step (b) can introduce mutations into a gene regulatory region, an open reading frame, an intron, or a combination thereof. Any of the mutations can be insertions, deletions, substitutions, or a combination thereof. Any of the oligonucleotides can be about 30 to about 120 nucleotides in length. The oligonucleotides of (b) can a pool of oligonucleotides each having 1 or more mutations.

The method can include a step (iii) of selecting mutant cells that have a mutation in the target region. The selection of mutant cells with a mutation in the target region can include phenotypic or genotypic screening.

The host cells can be any eukaryotic cells, for example, yeast cells, fungal cells, mammalian cells, or plant cells. The host cells can be deleted or otherwise treated or altered to reduce expression of RAD51 or a homolog thereof, alone or in combination with RAD52. The host cells can be deleted or otherwise treated or altered to reduce expression of one or more DNA mismatch repair enzymes. The DNA mismatch repair enzyme can be selected from the group consisting of MSH2, MSH6, MLH1, PMS1, homologs thereof, and combinations thereof. In some embodiments, expression of RAD59 or another ssDNA protein or recombinase (e.g., Beta recombinase), or a homolog thereof is increased in the host cells.

Host cells can also include a selectable marker adjacent to an origin of replication.

The method can include treating host cells prior to and/or during step (i) to reduce replication fork speed. For example, the cells can be treated with hydroxyurea.

In some embodiments, steps (i) and (ii) are repeated for two or more cycles using the same or different oligonucleotides for steps (a) and (b). The target region can include a biosynthetic pathway having two or more genes and oligonucleotides of step (b) can target two or more of the genes in the biosynthetic pathway.

Libraries of mutant cells prepared according to any the disclosed methods, and well as single mutant cells and clonal colonies thereof, are also provided.

| WT Target Sequence Top Strand | Mutation Sequence Top Strand |
| --- | --- |
| GCTTCCAA | NNNNNNNN |
| ATG | GTG |
| ATATATATA | NNNNNNNNN |
| TATA | WAWR |
| TATAAATA | NNNNNNNN |
| ATGCTTTCTTTTTCTCTTTTTT ACAGATCA (SEQ ID NO: 106) | WTKYTTTYTTTTTYTYTTTTTWY WKWTYW (SEQ ID NO: 122) |
| TCAAGGAAGTAATTATCTACT TTTTACAACA (SEQ ID NO: 110) | WMAARRAARWAAWWAWMWAM WWWWWAMAAM (SEQ ID NO: 126) |
| CAAGGG | CAAAAAAAAAAAAAAAAAAAAA AGGG (SEQ ID NO: 130) |
| CGA | AGA |
| AGG | CGG |
| TAT | TAGT |
| GGGACTCA | GGGGCTCA |
| CAAACA | CAATTATTACA (SEQ ID NO: 134) |
| CAATTATTTACA (SEQ ID NO: 165) | CAAACA |

Figure 4A:
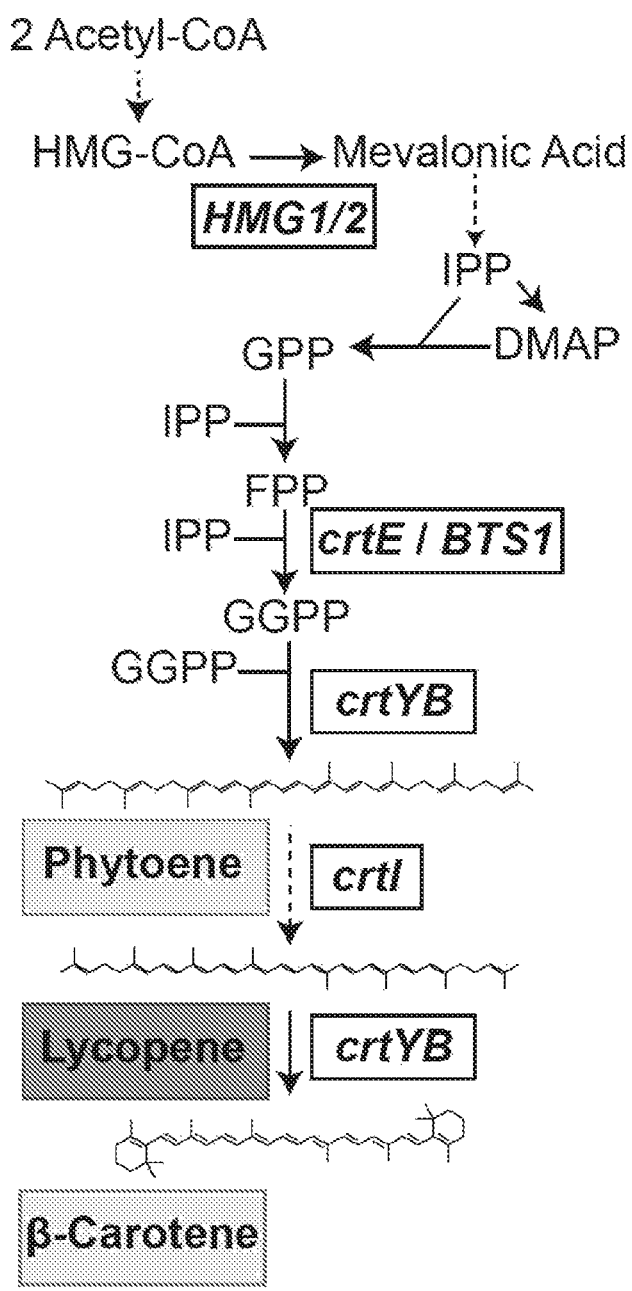
FIG. 4A is an illustration of the β-carotene biosynthetic pathway constitutively expressed in yeast.
Figure 4B:
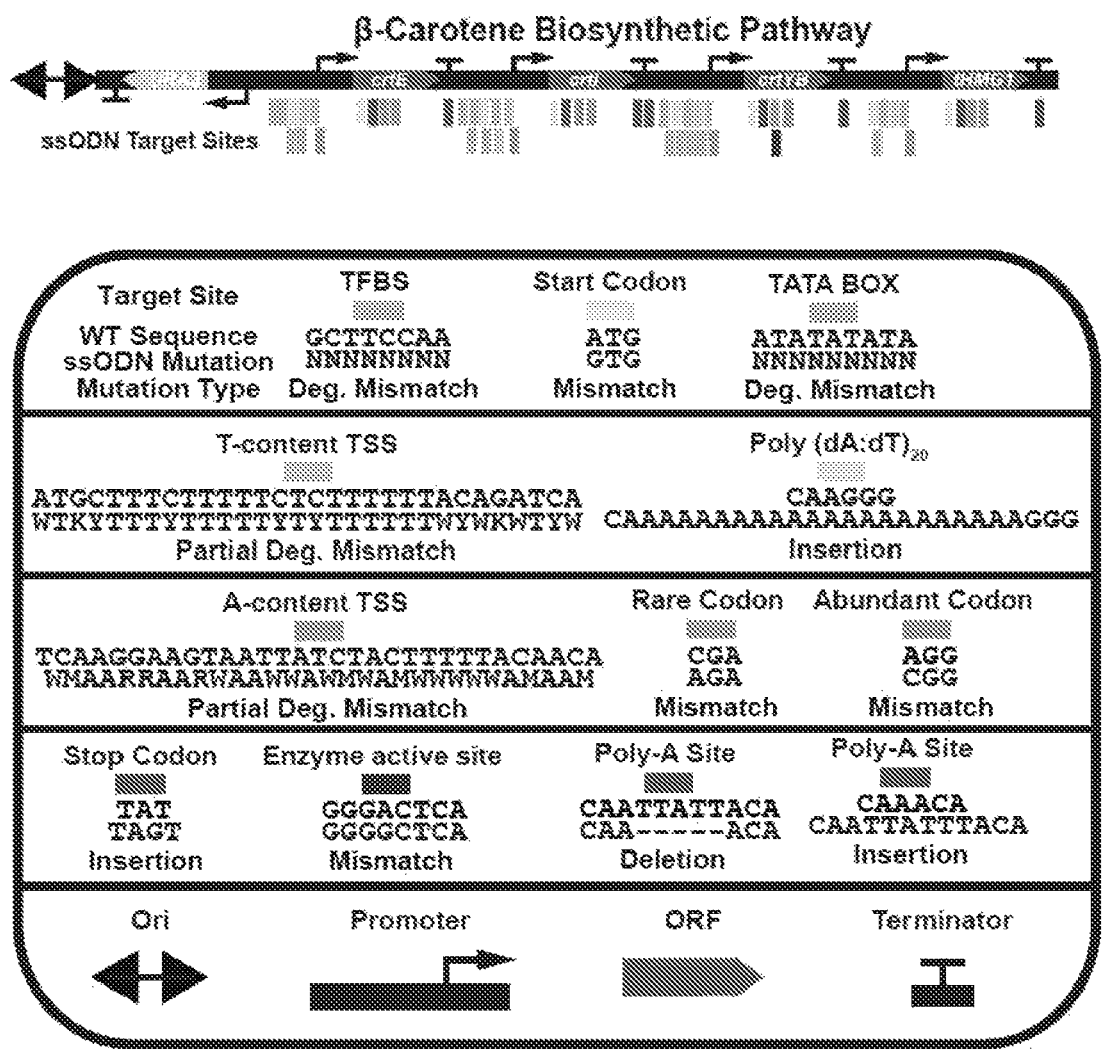
FIG. 4B is a genetic map of the β-carotene biosynthetic pathway showing target sites in promoters, ORFs, and terminators. The Table below the genetic map shows examples of targeted mutation sequence types. The sequences in FIG. 4B are.
Figure 4C:
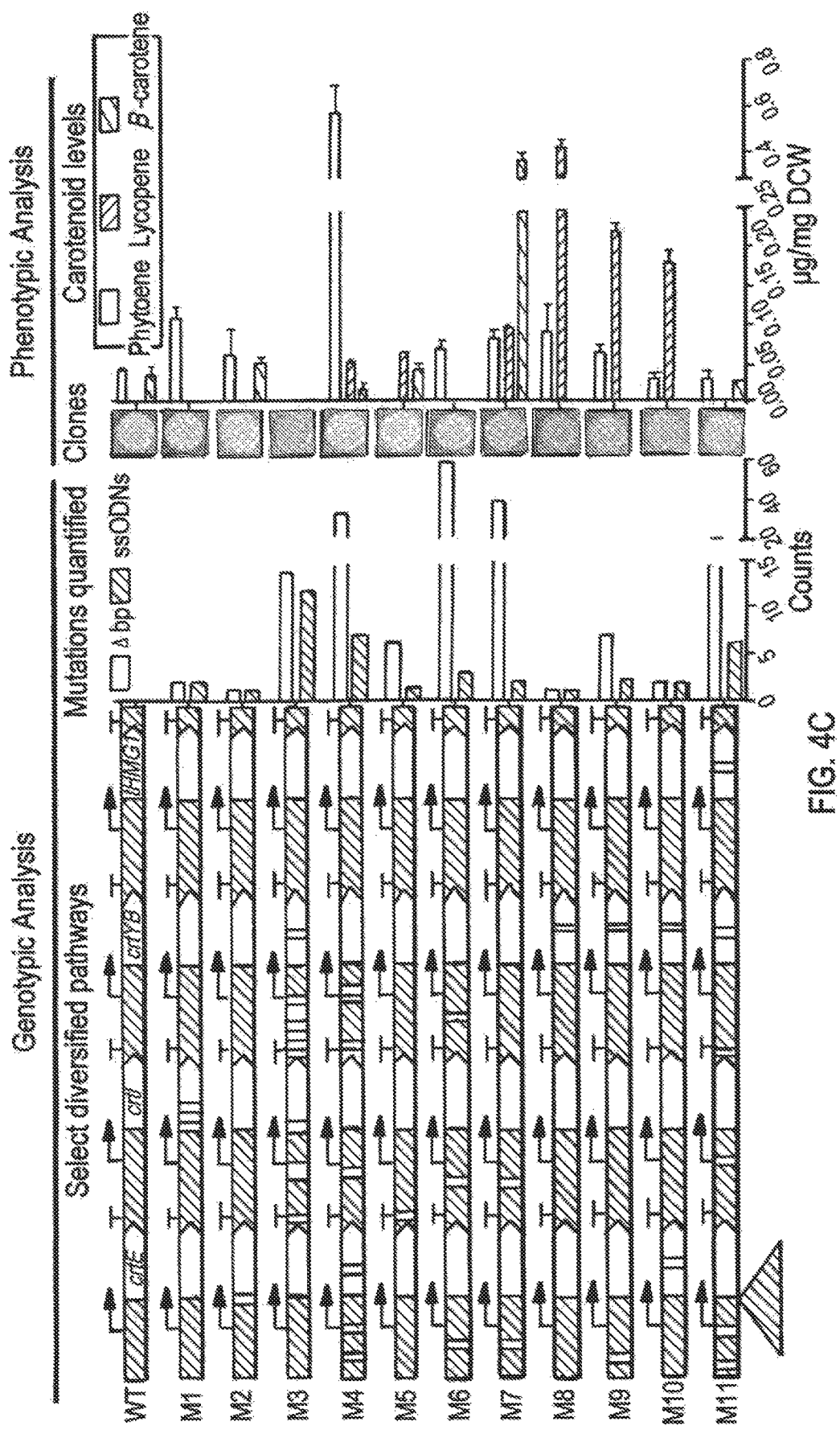

FIG. 4C shows genotypic and phenotypic analysis of select clones containing diversified genotypes and phenotypes uncovered with Sanger sequencing and HPLC analysis. Total number of ssODNs incorporated and number of targeted base-pair changes and HPLC data for clonal production of β-carotene lycopene, and phytoene (ug/mg dry cell weight) are shown in bar graphs. Values represent mean+/−SD.

The sequences in FIG. 4C are:

| Target Element | Promoter | Promoter | Promoter | Terminator | ORF | ORF |
|---|---|---|---|---|---|---|
| WT | ATTTTCC | TCAAGGAA GTAATTAT CTACTTTT TAG (SEQ ID NO: 110) | CATTCA ATC | TTCTAGTT ATTGGTC AT (SEQ ID NO: 168) | CGA | AGG |
| Oligo | NNNNNNN | WCAAGGA AKTAATTA WCWACWT TTWAC (SEQ ID NO: 166) | RWTTRW WTR | TTCTAG---- -GGTCAT | AGA | CGG |
| Mutant | CGCATGT | ACAAGGA AATAATTA ACAACATT TAAC (SEQ ID NO: 167) | CTTTCAT TT | TTCTAGG GTCAT (SEQ ID NO: 169) | AGA | CGG |

FIG. 4D shows and expanded view of clone M14 containing targeted edits in promoters, ORFs, and a terminator. Sequence of ancestral WT clone aligned to ssODN design, and M14 mutant sequence. The mutation type (Degenerate mutations abbreviated as 'Deg.', Mismatch as 'MM') and location are indicated.

Figure 5:
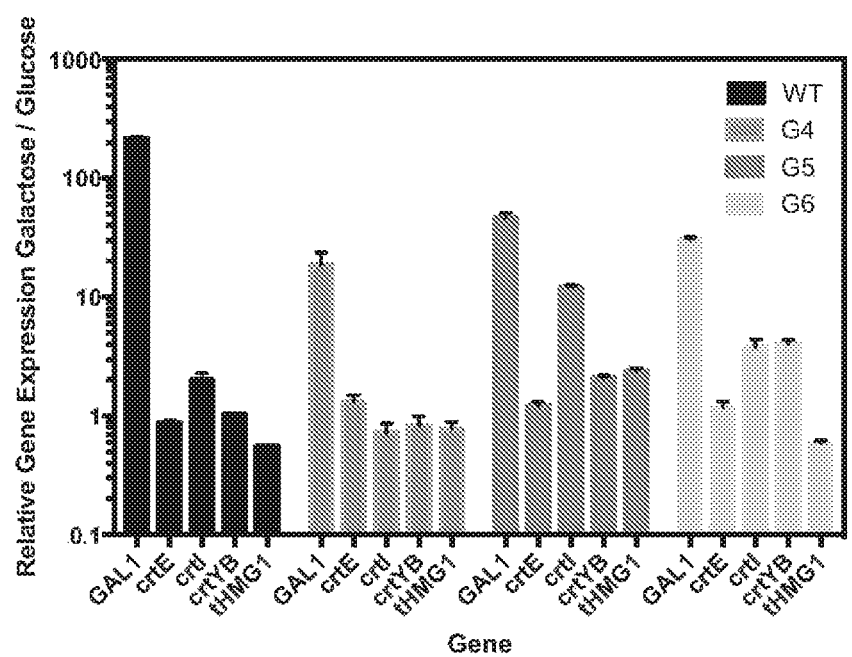

FIG. 5 is bar graph showing relative gene expression galactose/glucose in four mutant pathways with Gal4-TFBS targeted to replace native TFBS in promoters.

DETAILED DESCRIPTION OF THE INVENTION

I. Definitions

As used herein, the term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the terms "oligonucleotide," "nucleic acid oligomers," and "polynucleotide" refers to a natural or synthetic molecule including two or more linked nucleotides.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As used herein, the term "vector" refers to a polynucleotide capable of transporting into a cell another polynucleotide to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

As used herein, the terms "transformation" and "transfection" refer to the introduction of a polynucleotide, e.g., an expression vector, or single stranded oligonucleotide into a recipient cell including introduction of a polynucleotide to the chromosomal DNA of the cell.

As used herein, the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

As used herein, the terms "host," "parent," "parental," "progenitor," and "background," when used to describe a cell, population of cells, or strain of cells, refer to the cell type or strain type that is subjected to the disclosed methods of editing eukaryotic genomes.

II. Methods of Editing Eukaryotic Genomes

RAD51 dependent methods of gene editing exhibit low efficiency. RAD51-independent methods of gene editing are provided. In the disclosed methods, eukaryotic genome editing is carried out by targeting modification at the replication fork. Unlike most prokaryotes, eukaryotic genomes are typically arranged in linear chromosomes with multiple origins of replication that are known to fire stochastically throughout S-phase. Targeting synthetic oligonucleotides to the DNA replication fork has been a major technical challenge compared to prokaryotes.

At any given time a subset of cells in a given population have a replication fork active at the genomic site of interest. Thus methods for selecting these cells from the population to enrich for cells that can be highly edited by synthetic oligonucleotides using a replication fork annealing mechanism are provided.

The disclosed methods typically include one or more rounds of replication fork annealing-induced genome modification, followed by selection for cells likely to carry a modification in the target region. Typically at least one oligonucleotide is designed to mutate a selectable marker and at least one oligonucleotide is designed to mutate a target region near, preferably downstream of, the marker on the same chromosome. Cells are selected based on mutation of the selectable marker and can be screened for desirable mutations in the target region. The method can be harnessed to induce single or multiple mutations into one or more target regions during each round of transformation and selection.

A. Selectable Markers

The disclosed methods of genome editing are typically carried out in cells including a selectable marker. To improve selection of genetically modified mutants the marker should be adjacent, preferably directly adjacent, to one or more origins of replication near the region that is the target of genomic modification. In the most preferred embodiments, the cells include a marker adjacent, preferably directly adjacent, to the origin of replication that is closest to the region that is the target of genomic modification. Selected cells that incorporate the mutagenic oligonucleotide at the selectable marker gene are primed for incorporating other oligonucleotides in the target region at the same replication fork.

Figure 1A:
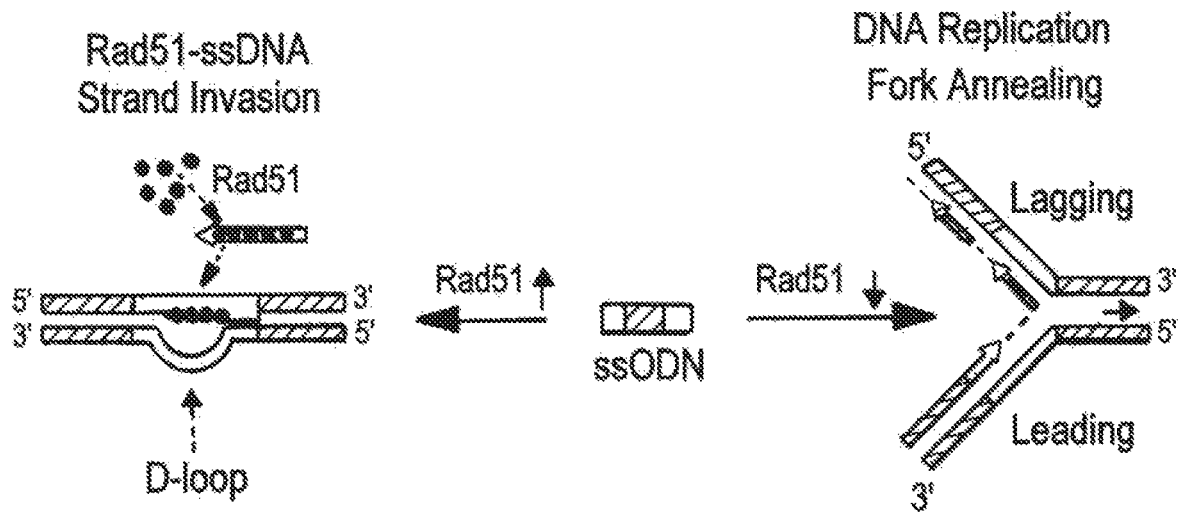
FIG. 1A is diagram illustrating two pathways for ssODN incorporation in the genome. Rad51-dependent ssDNA strand invasion and annealing of ssODNs at the replication fork independently of Rad51.
Figure 1B:
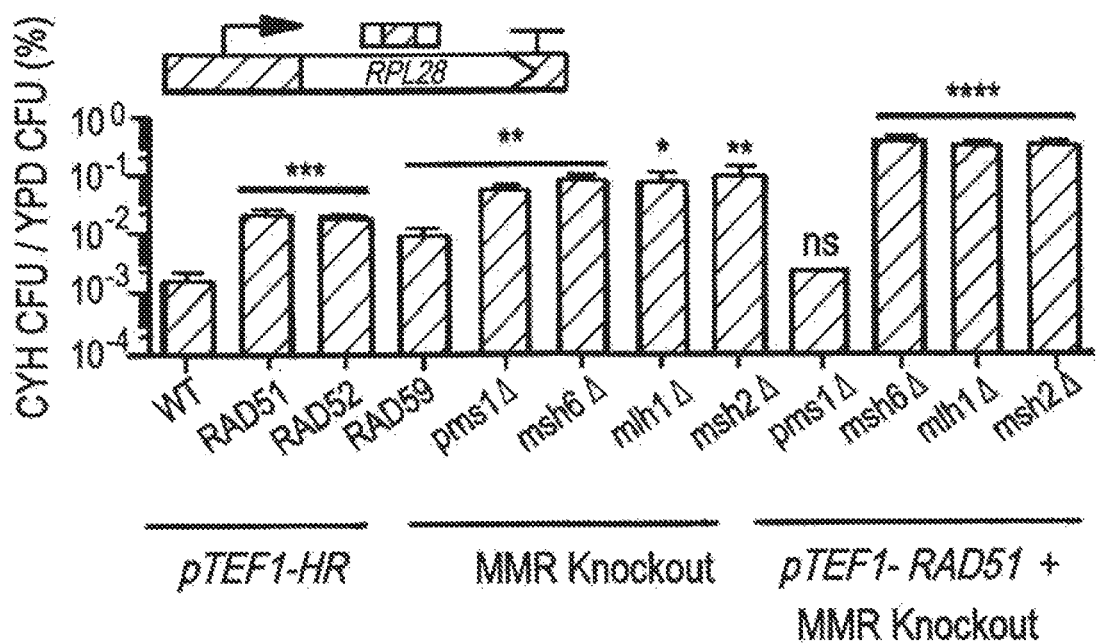
FIG. 1B is a bar graph showing ssODNs gene targeting with pTEF1 overexpression of HR genes (capitalized), MMR knockout strains, and combinations of pTEF1-RAD51 and MMR knockouts.
Figure 1C:
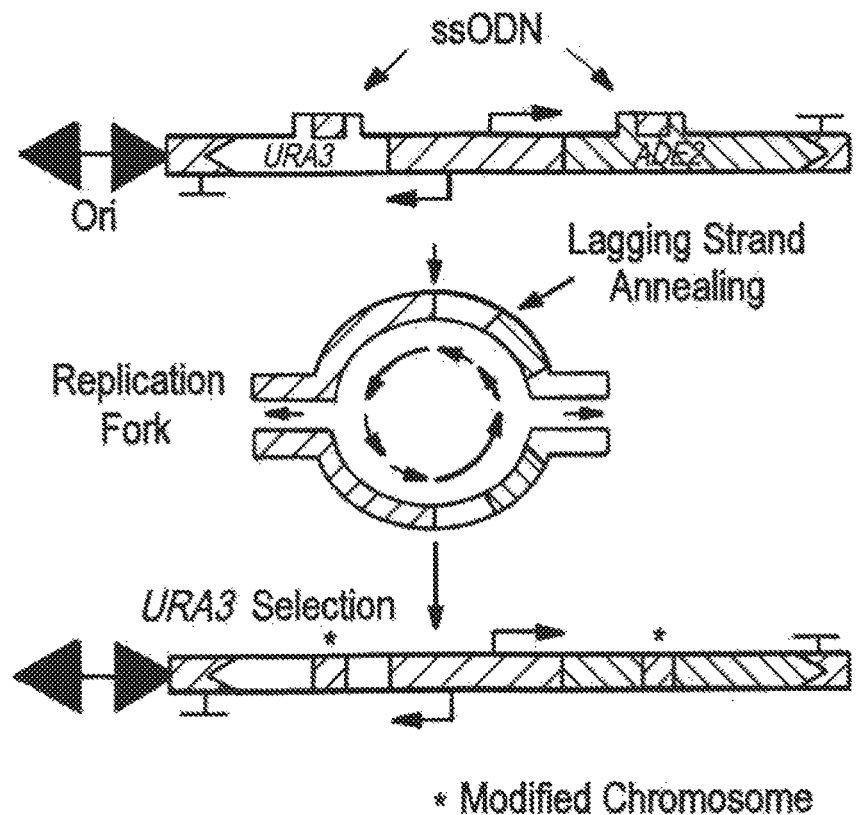
FIG. 1C is a diagram illustrating two structural cases for URA3 and the target gene orientation with respect to the origin of replication (Ori).
Figure 1D:
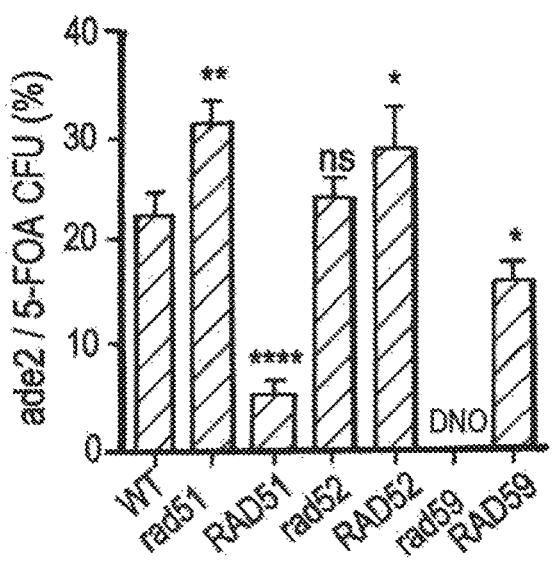
FIG. 1D is a bar graph showing ssODN annealing events at the replication fork in WT vs. Rad51, Rad52, and Rad59 knockout strains vs. constitutive expression (capitalized) of the indicated gene. (DNO: did not observe).
Figure 1E:
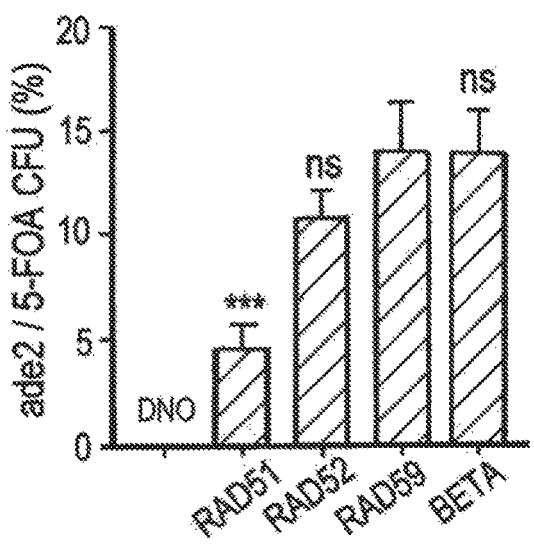
FIG. 1E is a bar graph showing rescue of Rad59 knockout phenotype with expression of Rad51, Rad52, and lambda red SSAP beta.
Figure 1F:
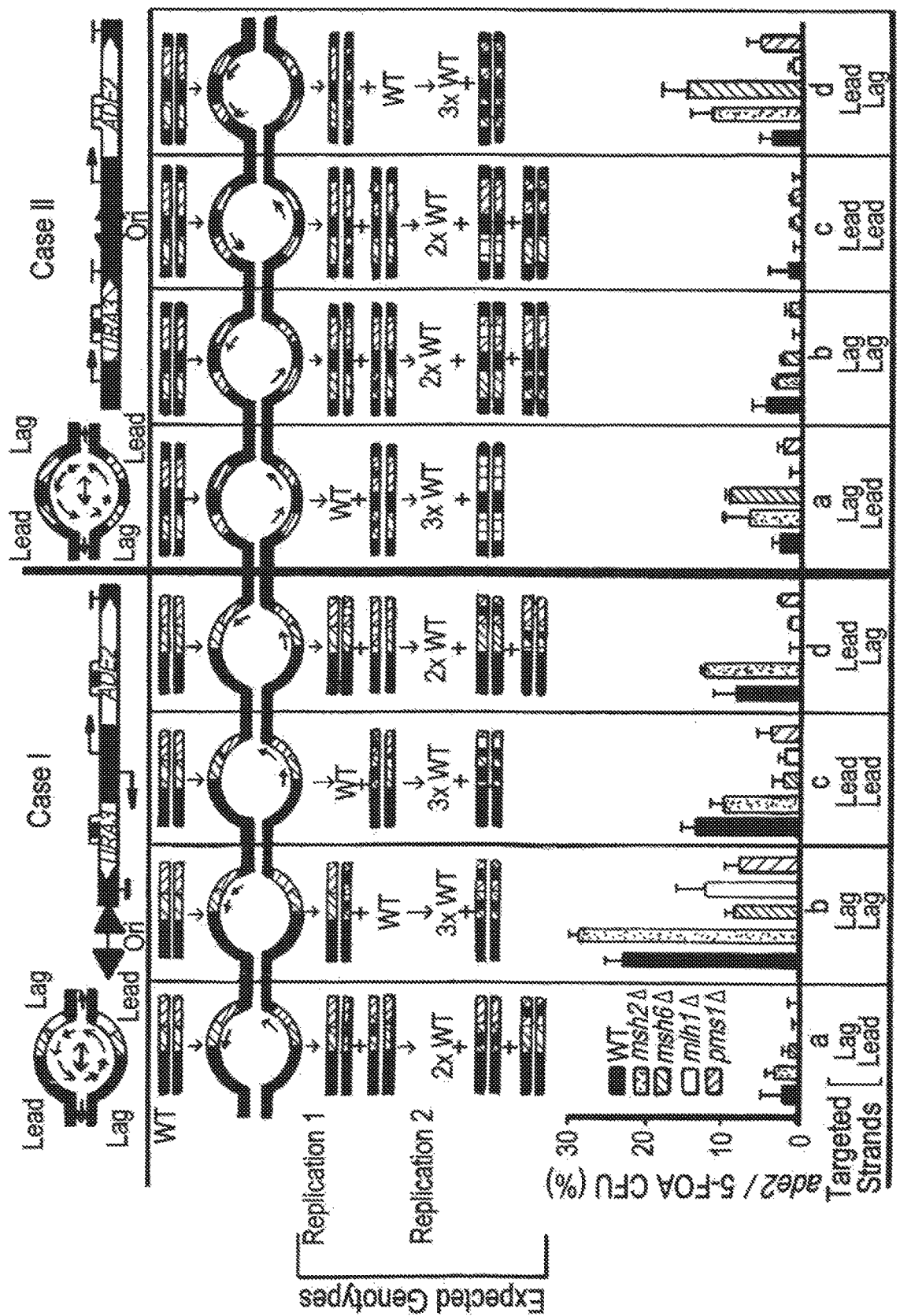
FIG. 1F shows efficiencies of strand targeting combinations at the replication fork for Case I and Case II orientations. Diagrams for each subcase a-d indicate the predicted segregation of the edited URA3 and ADE2 alleles after two replications. Allelic Replacement Frequency (ARF) represents percentage of edited cells per surviving cell after transformation and selection for the indicated phenotype. Values represent mean+/−SD. Two-tailed p-values from unpaired T-test vs. WT control strain. (*p<0.05; p<0.005; *p≤0.001;****p<0.0001).

In the most preferred embodiments, there is only one or zero origins of replication between the selectable marker and the target region, though in some cases there can be more, particularly if the oligos are targeted to the appropriate strand (see, e.g., FIG. 1F). FIGS. 1C and 1F also exemplified a target locus that is on the opposite side of an origin of replication from the selectable marker. Alternatively, the origin between two loci can be deleted, and/or methods could be employed to promote the firing of one origin and not the other through manipulation of the cell-cycle with chemicals or via a targeted protein such as CRISPR/cas to physically bind to the origin and prevent its function.

Figure 2A:
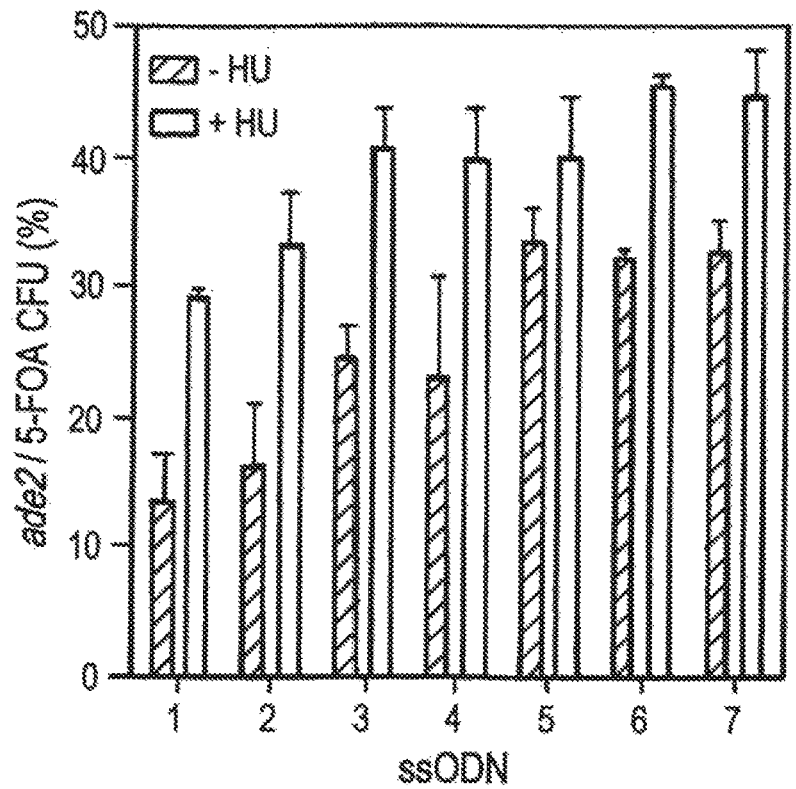
FIG. 2A is a bar graph showing the effect of hydroxyurea (HU) treatment for seven ssODNs each containing a single base-pair change.
Figure 2B:
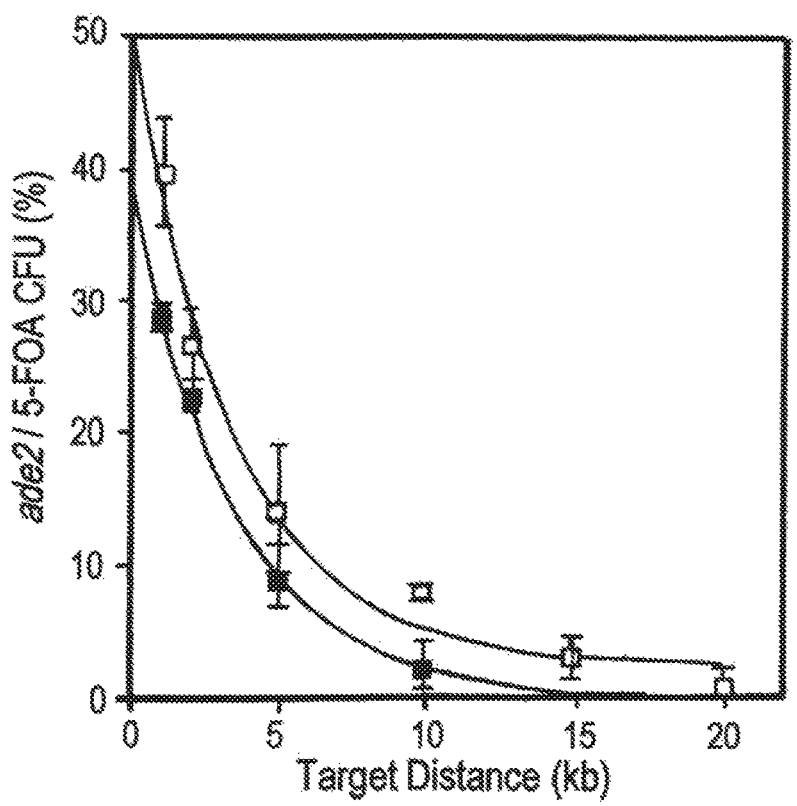
FIGS. 2B-2D are plots showing the allelic replacement frequencies (ARFs) of various genome modifications: (2B) Mismatches, (2C) Insertions, and (2D) Deletions.

In yeast the average distance between origins of replication is approximately 30 kb, while in mammals the origin distances can be 1-2 million bases. Thus in some embodiments the target region can be from 1 base pair to up to about 2 million or more (as many as 100 million bp) base pairs in either direction from the origin of replication closest to the selectable marker. FIG. 2B in the Examples below shows that methods achieved >40% at 1-2 kb and >1% Allelic Replacement Frequencies (ARF), which is more than 10-fold higher than standard oligo recombination, when targeting a region at a distance of 20 kb away from the origin of replication.

The selectable marker is typically adjacent to an origin of replication. In some embodiments, the selectable marker can be, or begin, within 500 bp, 1 kb, 1.5 kb, 5 kb, 10 kb, 15 kb, or 20 kb of the origin or replication. In some embodiments, the distance from the origin of replication is measured by genetic markers. For example, the selectable marker can be placed between the origin of replication and 0, 1, 2, 3, 4, 5, 10, 15, 20, 25 or more intact endogenous or heterologous genes in either direction from the origin.

The target region and the selectable marker can be separated by, for example, 4, 3, 2, 1, or 0, preferably 0 or 1, origins of replication. The target region can range from, for example, 1 base pair to 1 million, 2 million, 5 million, 10 million, 100 million, or more base pairs in either direction from the origin of replication closest to the selectable marker. The selectable marker can be placed such that 0, 1, 2, 3, 4, 5, 10, 15, 20, 25 or more genes are between it and the target gene or target region.

Preferably, the target region is closer to the origin of replication closest to the selectable marker than the next origin of replication, as the strand biases can change as the target region gets closer to the origin that is replicating from the other direction.

The selectable marker can be any marker that can drive a selection. The selectable marker can be a counter-selectable marker. A counter-selectable marker is a gene that can be selected in its presence and absence by altering specific chemicals in the cellular growth media. For example, under appropriate growth conditions, a counter-selectable gene promotes the death of the microorganisms harboring it (Reyrat, et al., *Infect Immun.* 1998 September; 66(9): 4011-4017). Transformants which have integrated a suicide vector containing a counterselectable marker (e.g., by a single event of homologous or illegitimate recombination) retain a copy of the counterselectable marker in the chromosome and are therefore eliminated in the presence of the counterselective compound. Consequently, counterselectable markers have been used for the positive selection of mutants that have undergone defined genetic alterations leading to the loss of the marker. The most-used counterselectable markers are the genes that confer sucrose, streptomycin, or fusaric acid sensitivity. An example is thymidine kinase, which makes the host sensitive to ganciclovir selection. Exemplary counter-selectable markers suitable for use in eukaryotes include, but are not limited to, hygromycin and zeocin. Another counter-selection marker for higher order eukaryotes is HPRT (Fukagawa, et al., *Nucleic Acids Research*, 27(9):1966-1969 (2000)

Positive selection markers are markers that confer selective advantage to the host organism, for example antibiotic resistance, which allows the host organism to survive antibiotic selection, or an enzyme that can complement an auxotrophy.

Positive and negative selectable markers can serve as both a positive and a negative marker by conferring an advantage to the host under one condition, but inhibits growth under a different condition. An example is an enzyme that can complement an auxotrophy (positive selection) and be able to convert a chemical to a toxic compound (negative selection). URA3, an orotidine-5' phosphate decarboxylase from yeast is a positive and negative selectable marker. It is required for uracil biosynthesis and can complement ura3 mutants that are auxotrophic for uracil (positive selection). The enzyme URA3 also converts 5-fluoroorotic acid (5FOA) into the toxic compound 5-fluorouracil, so any cells carrying the URA3 gene will be killed in the presence of 5FOA (negative selection).

A marker does not need to be a gene. It can also be a sequence of DNA base pairs in the chromosome that serve as the target site for a targeted nuclease. In this case, cells that acquire a targeted mutation in this "marker" region from the oligo are "immune" to the nuclease cleavage at the "marker" site. Cells that do not contain the mutation at the "marker" site will undergo nuclease-driven cleavage and present a growth disadvantage in the cell population.

As used in the disclosed methods, the marker is designed to be selectable following mutation by replication fork annealing of a mutagenic oligonucleotide. Thus in some embodiments, the marker is a counter-selectable marker that confers sensitivity to a compound and mutation alleviates sensitivity to the compound (e.g. URA3). Thus cells with a wildtype copy of the marker are killed when cultured in the presence of the compound, while cells with a mutated copy, induced by the mutagenic oligonucleotide, survive. In some embodiments, the marker is a mutated positive selectable marker, a wildtype copy of which is needed for the cells to survive in the presence of a compound. Thus cells with the mutant copy of the marker are killed when cultured in the presence of the compound, while cells with a copy of the marker reverted to wildtype by the mutagenic oligonucleotide, survive.

High levels of combinatorial genomic diversity can be achieved through iterative cycling of oligo incorporation. In the Examples below, cycling was achieved by the counter-selectable capability of URA3 through liquid selection of the population after each transformation. The odd cycle oligo targeted a nonsense mutation to URA3 for 5-FOA selections, and the even cycle oligo restored the functional URA3 gene for auxotrophic selection. A similar strategy of repeating cycles of introducing a mutation followed by reversing the mutation, or reversing a mutation followed by introducing a mutation, can likewise be applied to other selectable markers and marker strategies as discussed herein.

A string of several tandem unidirectional selection markers would also allow for many rounds of selection if the targeted marker was changed each round.

Other strategies include, for example, a GFP gene harboring a null mutation, which could be used for selecting cells via FACS if the "selectable" oligo restores the GFP, YFP, or any other fluorescent marker. It could be used in the opposite logic as well to sort out clones lacking GFP.

Other exemplary markers that can be used for positive and/or negative selection include, but are not limited to, lacZ gene, which encodes β-galactosidase, dihydrofolate reductase (DHFR), thymidine kinase, and antibiotics such as neomycin, neomycin analog G418, hydromycin, chlorophenicol, zeocin, blasticidin, KanR, geneticin, and puromycin.

Suitable auxotrophic markers are also known in the art. See, for example, ade1-14, ade1-101, ade2-1, ade2-101, ade2-BglII, can1-100, his3delta200, his3delta1, his3-11,15, his3delta, leu2delta1, leu2-3,112, leu2delta, lys2-801, lys2delta202, lys2delta, trp1delta1, trp1delta63, trp1-1, trp1-1, trp1delta, trp1-289, trp5delta, ura3-52, ura3-1, ura3delta, ura4delta, ade2delta::hisG, leu2delta0, lys2delta0, met15delta0, and ura3delta0, which are discussed in SGD Wiki, "Commonly Used Auxotrophic Markers."

In some embodiments, the selectable marker is an essential gene. The essential gene can be endogenous essential gene. In some embodiments the selectable marker is an endogenous essential gene that has been moved from its endogenous loci to be adjacent to an origin of replication. In some embodiments, the selectable marker is not an endogenous essential gene.

The Examples below illustrate oligos targeting four possible strand combinations for URA3 (selectable marker) and ADE2 (region targeted for genomic modification). In some embodiments, a selectable marker is present both adjacent to the origin of replication and as part of, or adjacent to, the region targeted for genomic modification. Thus in some embodiments, there is a marker that allows for direct selection of modifications at the region targeted for genomic modification.

The foregoing marker strategies are intended to by illustrative, and it will be appreciated that numerous marker strategies can be employed provided they allow the user to select for cells that have a mutation in a selectable marker adjacent to an origin of replication near a target region of interest. The Examples below illustrate that when cells were first selected based on mutation of a selectable marker and subsequently screened for additional mutations in target site locus, a dramatic 100-fold increase in the frequency of oligonucleotides incorporated at the adjacent target locus downstream of the marker were observed. Thus in some embodiments, including a selection step increases the frequency of oligonucleotides incorporated at the adjacent target locus 10, 25, 50, 75, 100, 150 or more —fold over the same method carried out absent selection based on mutation of a selectable marker adjacent to the target origin of replication.

The Examples below also illustrate that the observed targeting efficiencies at the target site increased from approximately 0.2% to 20% of colonies containing the desired mutations. Thus in some embodiments, the observed targeting efficiencies at the target site increases to 1%, 5%, 10%, 15%, 20%, 25%, 50%, or more of colonies containing the desired mutations when selection based on mutation of a selectable marker adjacent to the target origin of replication is included in the method.

In some embodiments, the cells include two or more selectable markers adjacent to the same origin of replication. In some embodiments, the cells include one or more selectable markers adjacent to two or more different origins of replication. The selectable markers can be the same or different. In this way, target regions at two adjacent to two or more origins of replication, on the same or different chromosomes, can be targeted at one time.

The selectable marker can be inserted into genome of the cells using traditional cloning methods, DSB, CRISPR/Cas9, or other methods that are known in the art.

B. Oligonucleotide Design

As introduced above, typically at least one oligonucleotide is designed to mutate the selectable marker and at least one oligonucleotide is designed to mutate a target region near, preferably downstream of, the marker on the same chromosome. Although it will be appreciated that mutation of the selectable marker is a genomic modification, as used herein, "target region," "target site of genomic modification," " etc., typically refers to one or more additional sites, which is not part of the selectable marker, at which genomic modification is desired. The target region(s) can be one or more genetic elements including, but not limited to, regulatory elements such as promoters and terminators, open reading frames, or other elements within the genome.

The oligonucleotides are typically single stranded oligonucleotides designed to hybridize to single stranded template strands of genomic DNA during replication. The oligonucleotide includes one or more mutations relative to the genome of the host cell, which is incorporated into the newly synthesized strand during replication. The selectable marker can be encoded on the same or opposite strand as the region targeted for genomic modification, or a combination thereof. The selectable maker can be on the same or opposite side of the origin of replication as the region targeted for genomic modification, or a combination thereof.

The Examples below illustrate oligos targeting four possible strand combinations for URA3 (selectable marker) and ADE2 (region targeted for genomic modification) arrangement were tested allelic replacement frequencies (ARF) is dependent on URA3/ADE2 orientation with respect to origin of replication (ARS1516). Targeting the lagging-lagging strand combination for URA3 and ADE2 was the most efficient when URA3 was located adjacent to ADE2. When the selectable marker and target region of genomic modification were divided by the origin of replication, targeting the URA3 leading strand and ADE2 lagging strand was most efficient, which is likely due to the two oligos targeting the same chromosomal strand. Thus in preferred embodiments, the selectable maker is on the same side of the selectable marker as the target region, and in particularly preferred embodiments, the oligos are designed to hybridize to the lagging strand of both the selectable marker and the target region. Thus in preferred methods, incorporation of the selectable marker and design of the oligonucleotides are coordinated such that oligonucleotides are incorporated as Okazaki fragments.

Although oligonucleotides greater than 120 or even those greater than 150 nucleotides in length can be used and should be suitable, typically synthetic oligonucleotides are prepared in the ranges of about 30 to about 120 nucleotides. In particular embodiments, the oligonucleotides are 30-90 nucleotides, 40-90 nucleotides, 50-90 nucleotides, 70-90 nucleotides, 30-120 nucleotides, or 40-120 nucleotides. The oligonucleotides contain at least one mutated, inserted or deleted nucleotide relative to the target DNA sequence. Target sequences can be within the coding DNA sequence of a gene or within introns. Target sequences can also be within DNA sequences which regulate expression of the target gene, including promoter or enhancer sequences or sequences that regulate RNA splicing.

The oligonucleotides can contain a variety of mutations relative to the target sequence. Representative types of mutations include, but are not limited to, point mutations, deletions and insertions. Deletions and insertions can result in frameshift mutations or deletions. Point mutations can cause missense or nonsense mutations. These mutations may disrupt, reduce, stop, increase, improve, or otherwise alter the expression of the target gene.

The methods can include use of one or more oligos targeting the selectable marker and one or more oligos targeting one or more target regions. The oligonucleotides can be administered in a single transfection, or sequential transfections, though a single transfection is preferred.

The methods can include introducing large pools of oligos with different sequences. In some embodiments one or a few oligos target the selectable marker and a much larger number of oligos target one or more genetic loci (i.e., region targeted for genomic modification).

Oligonucleotides can be DNA oligonucleotides, composed of the principal naturally-occurring nucleotides (uracil, thymine, cytosine, adenine and guanine) as the heterocyclic bases, deoxyribose as the sugar moiety, and phosphate ester linkages. Oligonucleotides can include modifications to nucleobases, sugar moieties, or backbone/linkages, depending on the desired structure of the replacement sequence at the target site or to provide some resistance to degradation by nucleases, to enhance stability introduced during chemical synthesis or subsequent enzymatic modification or polymerase copying. These modifications include, but are not limited to, the inclusion of one or more alkylated nucleic acids, locked nucleic acids (LNAs), peptide nucleic acids (PNAs), phosphonates, phosphothioates, and the like in the oligomer. Examples of modified nucleotides include, but are not limited to 5-fluorouracil, 5-bromouracil, 5-chlorouracil, 5-iodouracil, hypoxanthine, ÿanthine, 4-acetylcytosine, 5-(carboxyhydroxylmethyl)uracil, 5-carboxymethyl-aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

C. Mutagenesis

1. Methods of Mutagenesis

The disclosed methods can be used to introduce one or more nucleic acid sequences into a cell. The methods typically include introducing oligonucleotides including the desired nucleic acid sequence into cells by transformation or transfection.

The oligos can be introduced by methods known in the art, for example infection, transfection, transformation or transconjugation. Techniques for transferring DNA into such organisms are widely known and provided in references such as Sambrook, et al. (2012) *Molecular Cloning: A Laboratory Manual,* 4th ed., vol. 1-3, Cold Spring Harbor Press, Plainview N.Y. Exemplary preferred methods include electroporation, lipofection, calcium phosphate, or calcium chloride co-precipitation, DEAE dextran, or other suitable transfection method. For example, the cells can be transformed or transfected using transformation medium or transfection medium including at least one nucleic acid oligomer containing one or more mutations, replacing the transformation medium or transfection medium with growth medium, incubating the cell in the growth medium, and repeating the steps if necessary or desired until nucleic acid sequences have been introduced into the cell.

In some embodiments, the one or more nucleic acid oligomers is a pool of oligomers having a diversity of different random or non-random mutations at the location(s) of desired mutagenesis. Cells can be transfected with a variety of combinations of oligonucleotides leading to the formation of a diverse genomic library of mutants. The diversity of the library can be increased by increasing the number of cycles. Thus in some embodiments, multiple mutations are generated in a chromosome or in a genome. The oligomers can be single-stranded DNA.

Genetic diversity can be tuned by selecting the number and/or diversity of the oligonucleotides introduced during any step of the mutagenesis processes. It will be appreciated that the number of oligonucleotides can be increased, that the oligonucleotides can include one or multiple mutations per oligonucleotide and therefore target multiple position (e.g., amino acid positions encoded by the target DNA, etc.); that the oligonucleotides can introduce various types of mutations (mismatches, insertions, deletions and with varying degrees of degeneracy (4N—A, T, G, C, 2 selected therefrom, or 3 selected therefrom) or specificity (N equals specific nt).

As exemplified in the experiments below, the disclosed methods are amenable to transfection with very large numbers of mutagenic oligonucleotides, in the range, for example of 1 to 1,000,000,000,000 oligonucleotides. This number can be very high because the oligos can be designed to have degenerate positions and thus quickly expand the complexity of the oligo pool, i.e., the number of oligos. The experiment reported in FIGS. 3A-3I utilized a pool of 10,024 oligonucleotides. Other experiments described below utilized an oligo pool that contained a design with 17 degenerate 'N' positions thus having a complexity of $4^{17}$, which is greater than $1.7*10^{10}$ different oligos in single transfection.

Genetic diversity of the mutants can also be tuned by the number of cycles of mutagenesis. For example, increasing the number of cycles of mutagenesis generally increases the diversity of the library. In particular embodiments, a library is prepared by one or more cycles or transformation and selection, for example, 1, 2, 3, 4, 5, 6, 7, 8, 9, 10, 11, 12, 13, 14, or 15. In a particular embodiment, a library of mutants is prepared by, for example, between 1 and 50, between 3 and 15, between 5 and 9 cycles. In some embodiments, one or more round of transformation is carried out without intervening rounds of selection. The methods can also be modified to include additional or alternative steps to improve genetic diversity. See, for example, Carr, et al., *Nucleic Acids Research*, 1; 40(17):e132, 12 pages (2012), and Gregg, et al., *Nucleic Acids Research*, 42(7):4779-90 (2014).

The disclosed methods allow for multiplex automated genome engineering (MAGE) or eukaryotic cells (also referred to as "eMAGE" and "eukaryotic MAGE"). This approach was can be used in a similar fashion to bacterial MAGE to create generate multi-site gene modifications with base-pair precision at increased efficiencies. The methods can be used for pathway diversification, whole genomic recoding, and molecular evolution of proteins.

In general, the experiments can be divided into three classes, characterized by varying degrees of scale and complexity: (i) many target sites, single genetic mutations; (ii) single target site, many genetic mutations; and (iii) many target sites, many genetic mutations. For example, in the first class, the methods can be used to recode all instances of a stop codon (e.g., TAG) with a synonymous codon (e.g., TAA) to produce a genetically recoded organism with a 'blank' codon available. The 'blank' codon can be reassigned, for example, for site-specific incorporation of nonstandard amino acids.

In the second class, the methods can be used to explore the effects of all possible amino acid substitutions at a single target locus. In such an experiment, it is possible, for example, to use a single degenerate ssDNA containing the NNN triplet at its center to introduce all possible amino acid substitutions.

In the third class, the method can be used to construct diverse cell populations containing combinations of alleles across many loci involved in the biosynthesic pathways. This method is exemplified in the experiments below using a beta carotene biosynthetic pathway. In this implementation, discrete oligos designed to knockout competing pathways by deletion can be mixed with degenerate oligos designed to randomize target positions in the coding sequence or regulatory regions of key pathway enzymes. The highly diverse population resulting from use of the provided methods can be used downstream to screen or select for mutants with a prescribed phenotype (e.g., overproduction of a metabolite or small molecule).

2. Methods of Selection

As discussed above, in some embodiments, such as those discussed above, a diverse population is the desired result and no further selection or analysis is needed. However, in some embodiments, one or more particular phenotypes or genotypes are desired. Thus, in some embodiments, coincident with or after a preferred population of prospective mutants is prepared by one or more rounds of transfection and selection for modification of the selectable marker at the desire origin of replication, a subset or individual cells can be selected based on a desirable phenotype or genotype.

Selection can include one or more cycles of negative selection, one or more cycles of positive selection, or a combination thereof. Selection can be integrated in between cycles of mutagenesis, reserved until after mutagenesis is complete, or a combination thereof. Negative selection can be before or after positive selection, or a combination thereof. Positive selection can be before or after negative selection, or a combination thereof. Therefore, selection can include any combination of iterative rounds of positive and/or negative selection.

Negative selection generally refers to a process of reducing undesirable mutants from the library of mutants. Positive selection generally refers to a process of choosing desirable mutants from the library of mutants. Selection can include, for example, in some embodiments, the mutagenesis creates or corrects auxotrophy, creates or destroys sensitivity to a compound or a nuclease, or creates, alters or destroys another biochemical, morphological, or phenotypic characteristic. In some embodiments, the individuals are additionally or alternatively screened or selected by genotyping, such can include genomic sequencing, as well as hybridization techniques that allow the practitioner to select the desire cell(s) without actually sequencing the cell's genome. By way of non-limiting illustration, the target region of some of the experiments below was the ADE2 gene, and red/white phenotype of ADE2 was used as a screening assay for ade2 mutants.

D. Tuning Replication Fork Speed and Other Considerations

Mutagenesis can be improved by reducing the speed of the replication fork. Cells can be cultured or otherwise treated with a compound, such as hydroxyurea, that transiently slows the DNA replication fork in an effective amount to allow for even higher efficiencies of oligonucleotide incorporation. In some embodiments, oligonucleotide incorporation is improved 10, 25, 30, 35, 40, 45, 50, 55, 60, 70, 75, 80, 85, 90, 95, 100 percent or more. The Examples below utilize hydroxyurea in range of about 200 nM to about 800 nM, with the greatest changes in oligonucleotide incorporation observed in the range of about 300 nM to about 700 nM, and about 400 nM to about 600 nM. In the non-limiting experiments below, a short exposure time of 30 minutes prior to transformation was utilized to minimize any mutagenic effects of HU. In some embodiments, the exposure to hydroxyurea or another agent that reduces replication fork speed, is between about "x" minutes and about "y" minutes, wherein "x" is an integer between 1 and 359, and "y" is an integer between 2 and 360 that is greater than "x".

The Examples also show that efficiencies of replication fork oligonucleotide incorporation were decreased by high levels of RAD51 and the efficiencies increased in the rad51 knockout conditions. In some embodiments, the cells utilized in the disclosed methods are mutated or deleted at rad51 and/or rad52 (or their homologs in another species). These data indicate that replication fork annealing is a competing alternative mechanism to the canonical RAD51 ssDNA strand invasion mechanism used in other methods.

RAD59 appears to play a role in replication fork annealing. Thus in some embodiments, the rad59 gene (or its homologs in another species) is intact and/or expression is expressed or supplemented using compositions and methods known in the art. For example, cells can be genetically modified to increase (or constitutively express RAD59), cells can be transfected with a rad59 expression construct, or mRNA or protein can be transiently transfected into the cells. Additionally or alternatively expression of another ssDNA annealing or binding protein or recombinase (e.g., Beta recombinase) or a homolog thereof, is increased. A heterologous recombinase (beta) can complement rad59 deletion. Examples of ssDNA recombinases include, but are not limited to

| Recombinase | Bacterial Source |
| --- | --- |
| Beta | E. coli |
| EF2132 | E. faecalis |
| OrfC | L. pneumophila |
| S065 | V. cholerae |
| Plu2935 | P. luminescens |
| RecT | E. coli |
| Orf48 | L. monocytogenes |
| Orf245 | L. lactis |
| GP35 | B. subtilis |
| GP61 | M. smegmatis |
| GP20 | S. aureus |

Other examples of recombinases are known in the art and can be found in the Remote Homology Detection of Viral Protein Families (VIRFAM) website.

In some embodiments, the cells are mutated or deleted at one or more DNA mismatch repair (MMR) genes. Exemplary genes include msh2, msh6, mlh1, and pms1 in yeast, and their homologous in other species.

In some embodiments, mutations are amplified by mating two cells. For example, in the experiments below, haploid yeast mutant libraries were prepared targeting mutations to different target regions, and haploids carrying varying mutations were subsequently mated to compound the mutations.

E. Cells

The disclosed methods are designed for use in eukaryotic systems. The methods are particularly suitable for use with eukaryotic genomes arranged in linear chromosomes with multiple origins of replication that fire stochastically throughout S-phase. Typically, the host, parent, parental, progenitor, or background cell, population of cells, or strain of cells is one that has one or more modifications, typically genetic modifications, which improve its use or application in the disclosed methods. For example, the host, parent, parental, progenitor, or background cell, population of cells, or strain of cells can be the one(s) that is transformed or transfected with one or more single-stranded oligonucleotides for selectable marker modification, target region modification, or a combination thereof or a predecessor cell thereof 1. Eukaryotic Cells Yeasts useful as host cells include, but are not limited to, those from the genus *Saccharomyces, Pichia, K. Actinomycetes, Kluyveromyces,* and *Yarrowia* (e.g., *Yarrowia lipolytica*). The methods can include other standard molecular biological techniques, and may utilize, for example, vectors. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, (1980)) or other glycolytic enzymes (Holland et al., *Biochem.* 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., Gene 344:43-51 (2005) and Daly and Hearn, *J. Mol. Recognit.* 18(2):119-38 (2005). Other suitable promoters and vectors for yeast and yeast transformation protocols are well known in the art.

In some embodiments, the cells are mammalian, fungal, insect, or plant cells. Suitable host cell culture systems are well known in the art. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The disclosed methods are exemplified below using a yeast system, however, most or all of the steps should be adaptable for use in other eukaryotic cells. Small changes may be employed to utilize molecular biological techniques that are particularly advantageous or disadvantageous in one system over another. For example, the physical method of oligo delivery might be dictated by the system: Lipofection might be used as the most optimal delivery method in mammalian cells compared to electroporation in yeast. However once inside the cell, the oligo will encounter structurally the same replication fork and the same principles of fork slowing with hydroxyurea (shown to work the same way mammalian cells), and annealing to the lagging strand as an Okazaki fragment mimic would apply, etc. Other eukaryotes can also be cultured for several generations so the general principles of cycling protocol to generate targeted genomic diversity also apply, and the relevant replication, recombination, and repair proteins are conserved in eukaryotes from yeast upwards to human.

2. Parent Cells

Cells for use as the host, parent, parental, progenitor, or background cell, population of cells, or strain of cells in the disclosed methods are also provided. As introduced above, preferred cells can be predisposed, genetically modified, or otherwise inclined to increase, enhance, or favor replication fork annealing, enhance introduction of genetic mutations, or a combination thereof. For example, as discussed above, RAD59 appears to play a role in replication fork annealing. The rad59 gene (or its homologs in another species) can be intact and/or expression is expressed or supplemented using compositions and methods known in the art and discussed above. Additionally or alternatively expression of another ssDNA annealing or binding protein or recombinase (e.g., Beta recombinase) or a homolog thereof, is increased or supplemented as discussed above.

The parent or progenitor cells can have pre-existing modification(s) that reduce the effectiveness of intrinsic DNA damage prevention, DNA damage repair, or a combination thereof. The cells include those wherein the ability to carry out a DNA mismatch repair pathway is reduced or prevented. For example, the cells can be mutated or deleted at rad51 and/or rad52 (or their homologs in another species). Other pathways include the post-replicative DNA mismatch repair system (MMR), which in eukaryotic systems including human can include two different heterodimers: MutS alpha (MSH2-MSH6 heterodimer) and MutS beta (MSH2-MSH3 heterodimer) which binds to DNA mismatches thereby initiating DNA repair. Base-pair mismatches are recognized by MutS alpha and beta heterodimers. The complex of MutS and mismatched DNA recruits MutL (related genes include: MLH1, MLH2, MLH3, MLH4, PMS1, PMS2, and others) leading to subsequent strand separation and degradation by a variety of other factors. Cells can have mutation or deletion in one or more msh, mlh, or pms genes that can reduce the function or effectiveness of MMR. In the examples below, some of the yeast strains have a msh2 deletion.

The parent or progenitor cells can also be predisposed, genetically modified, or otherwise inclined to increase, enhance, or favor selection of the desirable progeny or clones after the parent or progenitor cells are subjected to the genome modification methods disclosed herein. For example, the parent or progenitor cell can be genetically modified to include a selectable marker adjacent, preferably directly adjacent, to an origin of replication near the region that is the target of genomic modification. Suitable selectable markers are discussed in more detail above and exemplified in the experiments described below.

In some embodiments, the cells have modified to express an exogenous or heterologous single-stranded annealing protein (SSAP), or recombinase, or overexpress an endogenous SSAP or recombinase system, or any combination thereof. In some embodiments, the cells have been modified to exclude a non-essential endogenous single-stranded annealing protein (SSAP) or recombinase, have not been modified to include an exogenous or heterologous SSAP or recombinase, or any combination thereof. Additionally or alternatively, the expression can be modulated up or down transiently with mRNA (increased expression) or inhibitory nucleic acids (e.g. siRNA) (decreased expression).

Examples of single-stranded annealing protein (SSAP) systems and recombinase systems include, but are not limited to, beta protein of λ Red, RecT protein of the RecET system, and/or proteins like Rad52-like, Rad51-like, or Gp2.5-like superfamilies, or a combination thereof. Single-stranded annealing protein (SSAP) systems or recombinase systems are discussed in WO 2015/017866. The SSAPs can be modified to include specific targeting sequences, such as a nuclear localization sequence (NLS) to promote trafficking to the eukaryotic nucleus.

Other exemplary genetic modifications for parental or progenitor cells are discussed in more detail in the examples below. See, for example, Table 1, which provides various parental yeast strains utilized in the experiments disclosed below. Any of the genetic modifications and strains provided in Table 1 can be used. The synonymous or homologous modification(s) can also be reproduced in other eukaryotes including, but not limited to, human cells.

The genetic background for the host cell can be selected based on the application. For example, the practitioner may desire to evolve a cell with one or more specific properties but these are agnostic to the genome sequence of the resultant organism. In this case, the MMR deficient background is useful in generating a large library of variants at the targeted sites with potential additional mutations that might contribute beneficially to the desired phenotype in an unforeseen manner. In some embodiments, the user might want to create one or more specific genetic mutants to test. In this case a preferred host cell would contain an intact MMR system or a transiently disabled MMR system to reduce the likelihood of additional mutations elsewhere in the genome.

Host cells can also include a selectable marker adjacent to an origin of replication.

3. Genetically Modified Cells

Cells resulting from the disclosed methods of eukaryotic genome modification are also provided. Such a cell is typically one (or a population thereof) that has one or more genomic modifications relative to its parent. The genomic modification is typically induced according to a disclosed method. Such cells can also be referred to as genetically modified cells, child or children cells, progeny, etc., relative to its parent cell. Most typically the genetically modified cells have one or more genetic modifications in one or more target regions or genes as discussed herein. In some embodiments, genetically modified cells, child or children cells, progeny, etc., may be further modified to remove or replace modifications that reduced the effectiveness of intrinsic DNA damage prevention, DNA damage repair, selectable markers, or a combination thereof, including those discussed above with respect to parent cells. These modifications may no longer be needed, or are even undesirable once a preferred child cells has been identified and selected. Additionally, or alternatively, mating techniques or other genetic manipulations can be used to compound the genetic modifications in two or more different child cells.

Additionally or alternatively RNAi or CRISPRi can be used as a knockdown strategy to transiently repress target changes. Also, those same genes and others can be modulated by expression from tunable promoters induced by chemicals, temperature or light.

III. Applications

The disclosed methods can be used for deeper exploration of genome sequence space and ultimately drive the ability to study and engineer new phenotypes for both fundamental research and industrial purposes. By altering multiple sites in the genome in a programmable fashion without cytotoxic effects, the methods and the cells made therewith can be utilized in every key area of eukaryotic biology. For example, the compositions and methods can be used in production of natural products from heterologous pathways (building off beta-carotene example discussed below), production of specialty chemicals, hydrocarbons (alkanes, alkenes), biofuels, drugs, and remediation (e.g., bioremediation).

Specific exemplary applications include, but are not limited to,

Elucidate causality for combinatorial sets of mutations related to disease or a phenotype of interest.

Exhaustive analysis of mutational landscapes for efficacy of drugs and the ability to test novel drugs against diversified mutants of the drug target or a related gene in a high-throughput manner.

Tuning expression of biosynthetic pathways from heterologous biological sources in a tractable eukaryotic host such as yeast.

Antibody engineering

Recoding of eukaryotic chromosomes

Tuning or enhancing the catalytic properties of enzymes.

Engineering production of biofuels, wine, beer, and high value compounds (i.e., fragrance compounds, opiates, etc).

Engineering in vivo sensors for desired chemicals or physical environments.

Engineering cells to tolerate harsh industrial environments (low pH, metal ions, salinity, ethanol concentrations, acetate concentrations, etc) more robustly.

Engineering plant enzymes for higher or tuned catalytic efficiencies (i.e., RuBisCO)

Targeting dividing cancer cells with ssODNs at the replication fork to increase the mutagenic load in the cell.

Engineering yeast for alternative carbon source utilization (e.g., pentose/cellulose from cheap feedstocks).

Enhance production of desired molecules in plants

Alter properties of plants to be tailored for specific environments

Algae genetic engineering

Furthermore, the disclosed methods are complementary and distinct with CRISPR/cas9 editing technology. Although recent advances in CRISPR/cas (or other nuclease-mediated technologies, e.g., Zinc Finger Nucleases, TALENs) have demonstrated new capabilities to introduce targeted gene editing modifications, the ability to generate high density, diverse and combinatorial modifications in eukaryotic genomes is limited by current technologies that require double-stranded DNA cleavage. The fundamental mechanism of CRISPR and its sister technologies will prevent it alone from achieving a comparable goal. The disclosed methods satisfy a complementary need of the CRISPR technology and expand the scaling of targeted genome modification across many loci, namely precise editing at many positions of the genome simultaneously, the ability to generate combinatorial genomic variation and a facile ability to iteratively introduce genome modifications from a complex oligonucleotide pool. The approach employs a fundamentally different mechanism than the CRISPR technology, which makes advantageous for editing genomes at high resolution and at many genomic sites at once.

EXAMPLES

Example 1: ssODN can be Designed to Anneal at DNA Replication Forks

Materials and Methods

Strain Construction

A complete list of strains used in this study can be found in Table 1. Strain BY4741 (MATa his3Δ1 leu2Δ0 met15Δ0 ura3Δ0) was chosen due to its common use as a laboratory strain and for its use in the *Saccharomyces Genome Deletion Project*. MMR knockout strains from the Saccharomyces Genome Deletion Project were purchased (Open Biosystems, Thermo Scientific). Strains harboring the URA3 marker for coupled ssODN selection (eMAGE) were constructed via homologous recombination with a dsDNA URA3 PCR product and selection on CSM-Ura plates. The β-carotene pathway is derived from *Xanthophyllomyces dendrorhous* and was PCR-amplified from plasmid pJC178, then incorporated at ARS1516 adjacent to the URA3 marker or at the indicated ARS location. Strains harboring the β-carotene biosynthetic pathway were constructed using a CRISPR-Cas9 genome integration step using gRNA target site sequence 'CTTGTTGCATGGCTACGAAC' located at chrXV 566360.

TABLE 1

A complete list of strains used in this study

| Name | Genotype | Ancestor | Description | Reference |
|---|---|---|---|---|
| BY4741 | MATahis3Δ1 leu2Δ0 met15Δ0 ura3Δ0 | NA | WT Strain | Brachmann et al. Yeast. 1998 Jan 30;14(2):115-32. |
| msh2Δ | MATahis3Δ1 leu2Δ0 met15Δ0 ura3Δ0 msh2::kanMX | BY4741 | msh2 knockout | Winzeler et al. Science. 1999 Aug 6;285(5429):901-6. |
| msh3Δ | MATahis3Δ1 leu2Δ0 met15Δ0 ura3Δ0 msh3::kanMX | BY4741 | msh3 knockout | Winzeler et al. Science. 1999 Aug 6;285(5429):901-6. |
| msh4Δ | MATahis3Δ1 leu2Δ0 met15Δ0 ura3Δ0 msh4::kanMX | BY4741 | msh4 knockout | Winzeler et al. Science. 1999 Aug 6;285(5429):901-6. |
| msh5Δ | MATahis3Δ1 leu2Δ0 met15Δ0 ura3Δ0 msh5::kanMX | BY4741 | msh5 knockout | Winzeler et al. Science. 1999 Aug 6;285(5429):901-6. |
| msh6Δ | MATahis3Δ1 leu2Δ0 met15Δ0 ura3Δ0 msh6::kanMX | BY4741 | msh6 knockout | Winzeler et al. Science. 1999 Aug 6;285(5429):901-6. |
| mlh1Δ | MATahis3Δ1 leu2Δ0 met15Δ0 ura3Δ0 mlh1::kanMX | BY4741 | mlh1 knockout | Winzeler et al. Science. 1999 Aug 6;285(5429):901-6. |
| mlh2Δ | MATahis3Δ1 leu2Δ0 met15Δ0 ura3Δ0 mlh2::kanMX | BY4741 | mlh2 knockout | Winzeler et al. Science. 1999 Aug 6;285(5429):901-6. |
| mlh3Δ | MATahis3Δ1 leu2Δ0 met15Δ0 ura3Δ0 mlh3::kanMX | BY4741 | mlh3 knockout | Winzeler et al. Science. 1999 Aug 6;285(5429):901-6. |
| pms1Δ | MATahis3Δ1 leu2Δ0 met15Δ0 ura3Δ0 pms1::kanMX | BY4741 | pms1 knockout | Winzeler et al. Science. 1999 Aug 6;285(5429):901-6. |
| rad51Δ | MATahis3Δ1 leu2Δ0 met15Δ0 ura3Δ0 rad51::kanMX | BY4741 | rad51 knockout | Winzeler et al. Science. 1999 Aug 6;285(5429):901-6. |
| rad52Δ | MATahis3Δ1 leu2Δ0 met15Δ0 ura3Δ0 rad52::kanMX | BY4741 | rad52 knockout | Winzeler et al. Science. 1999 Aug 6;285(5429):901-6. |
| rad59Δ | MATahis3Δ1 leu2Δ0 met15Δ0 ura3Δ0 rad59::kanMX | BY4741 | rad59 knockout | Winzeler et al. Science. 1999 Aug 6;285(5429):901-6. |
| EMB116 | MATahis3Δ1 leu2Δ0 met15Δ0 ura3Δ0 pRCVS6H-pTEF1-RAD51 | BY4741 | Rad51 overexpression | This Study |
| EMB117 | MATahis3Δ1 leu2Δ0 met15Δ0 ura3Δ0 msh2::kanMX pRCVS6H-pTEF1-RAD51 | msh2Δ | Rad51 overexpression, msh2 knockout | This Study |
| EMB118 | MATahis3Δ1 leu2Δ0 met15Δ0 ura3Δ0 msh6::kanMX pRCVS6H-pTEF1-RAD51 | msh6Δ | Rad51 overexpression, msh6 knockout | This Study |
| EMB119 | MATahis3Δ1 leu2Δ0 met15Δ0 ura3Δ0 mlh1::kanMX pRCVS6H-pTEF1-RAD51 | mlh1Δ | Rad51 overexpression, mlh1 knockout | This Study |

TABLE 1-continued

A complete list of strains used in this study

| Name | Genotype | Ancestor | Description | Reference |
|---|---|---|---|---|
| EMB120 | MATahis3Δ1 leu2Δ0 met15Δ0 ura3Δ0 pms1::kanMX pRCVS6H-pTEF1-RAD51 | pms1Δ | Rad51 overexpression, pms1 knockout | This Study |
| EMB126 | MATahis3Δ1 leu2Δ0 met15Δ0 ura3Δ0 pRCVS6H-pTEF1-RAD52 | BY4741 | Rad52 overexpression | This Study |
| EMB127 | MATahis3Δ1 leu2Δ0 met15Δ0 ura3Δ0 msh2::kanMX pRCVS6H-pTEF1-RAD52 | msh2Δ | Rad52 overexpression, msh2 knockout | This Study |
| EMB128 | MATahis3Δ1 leu2Δ0 met15Δ0 ura3Δ0 msh6::kanMX pRCVS6H-pTEF1-RAD52 | msh6Δ | Rad52 overexpression, msh6 knockout | This Study |
| EMB129 | MATahis3Δ1 leu2Δ0 met15Δ0 ura3Δ0 mlh1::kanMX pRCVS6H-pTEF1-RAD52 | mlh1Δ | Rad52 overexpression, mlh1 knockout | This Study |
| EMB130 | MATahis3Δ1 leu2Δ0 met15Δ0 ura3Δ0 pms1::kanMX pRCVS6H-pTEF1-RAD52 | pms1Δ | Rad52 overexpression, pms1 knockout | This Study |
| EMB146 | MATahis3Δ1 leu2Δ0 met15Δ0 ura3Δ0 pRCVS6H-pTEF1-RAD55 | BY4741 | Rad55 overexpression | This Study |
| EMB147 | MATahis3Δ1 leu2Δ0 met15Δ0 ura3Δ0 msh2::kanMX pRCVS6H-pTEF1-RAD55 | msh2Δ | Rad55 overexpression, msh2 knockout | This Study |
| EMB148 | MATahis3Δ1 leu2Δ0 met15Δ0 ura3Δ0 msh6::kanMX pRCVS6H-pTEF1-RAD55 | msh6Δ | Rad55 overexpression, msh6 knockout | This Study |
| EMB149 | MATahis3Δ1 leu2Δ0 met15Δ0 ura3Δ0 mlh1::kanMX pRCVS6H-pTEF1-RAD55 | mlh1Δ | Rad55 overexpression, mlh1 knockout | This Study |
| EMB150 | MATahis3Δ1 leu2Δ0 met15Δ0 ura3Δ0 pms1::kanMX pRCVS6H-pTEF1-RAD55 | pms1Δ | Rad55 overexpression, pms1 knockout | This Study |
| EMB156 | MATahis3Δ1 leu2Δ0 met15Δ0 ura3Δ0 pRCVS6H-pTEF1-RAD59 | BY4741 | Rad59 overexpression | This Study |
| EMB157 | MATahis3Δ1 leu2Δ0 met15Δ0 ura3Δ0 msh2::kanMX pRCVS6H-pTEF1-RAD59 | msh2Δ | Rad59 overexpression, msh2 knockout | This Study |
| EMB158 | MATahis3Δ1 leu2Δ0 met15Δ0 ura3Δ0 msh6::kanMX pRCVS6H-pTEF1-RAD59 | msh6Δ | Rad59 overexpression, msh6 knockout | This Study |
| EMB159 | MATahis3Δ1 leu2Δ0 met15Δ0 ura3Δ0 mlh1::kanMX pRCVS6H-pTEF1-RAD59 | mlh1Δ | Rad59 overexpression, mlh1 knockout | This Study |
| EMB160 | MATahis3Δ1 leu2Δ0 met15Δ0 ura3Δ0 pms1::kanMX pRCVS6H-pTEF1-RAD59 | pms1Δ | Rad59 overexpression, pms1 knockout | This Study |
| EMB98 | MATahis3Δ1 leu2Δ0 met15Δ0 ura3Δ0 msh6::kanMX ARS1516-URA3-ADE2 | msh6Δ | Case-I URA3-ADE, msh6 knockout | This Study |
| EMB99 | MATahis3Δ1 leu2Δ0 met15Δ0 ura3Δ0 mlh1::kanMX ARS1516-URA3-ADE2 | mlh1Δ | Case-I URA3-ADE, mlh1 knockout | This Study |
| EMB100 | MATahis3Δ1 leu2Δ0 met15Δ0 ura3Δ0 pms1::kanMX ARS1516-URA3-ADE2 | pms1Δ | Case-I URA3-ADE, pms1 knockout | This Study |
| EMB101 | MATahis3Δ1 leu2Δ0 met15Δ0 ura3Δ0 ARS1516-URA3-ADE2 | BY4741 | Case-I URA3-ADE | This Study |
| EMB102 | MATahis3Δ1 leu2Δ0 met15Δ0 ura3Δ0 msh6::kanMX URA3-ARS1516-ADE2 | msh6Δ | Case-II URA3-ADE, msh6 knockout | This Study |
| EMB103 | MATahis3Δ1 leu2Δ0 met15Δ0 ura3Δ0 mlh1::kanMX URA3-ARS1516-ADE2 | mlh1Δ | Case-II URA3-ADE, mlh1 knockout | This Study |
| EMB104 | MATahis3Δ1 leu2Δ0 met15Δ0 ura3Δ0 pms1::kanMX URA3-ARS1516-ADE2 | pms1Δ | Case-II URA3-ADE, pms1 knockout | This Study |
| EMB105 | MATahis3Δ1 leu2Δ0 met15Δ0 ura3Δ0 URA3-ARS1516-ADE2 | BY4741 | Case-II URA3-ADE | This Study |
| EMB106 | MATahis3Δ1 leu2Δ0 met15Δ0 ura3Δ0 msh2::kanMX URA3-ARS1516-ADE2 | msh2Δ | Case-II URA3-ADE, msh2 knockout | This Study |
| EMB259 | MATahis3Δ1 leu2Δ0 met15Δ0 ura3Δ0 msh2::kanMX ARS1516-URA3-ADE2 | msh2Δ | Case-I URA3-ADE, msh2 knockout | This Study |

TABLE 1-continued

A complete list of strains used in this study

| Name | Genotype | Ancestor | Description | Reference |
|---|---|---|---|---|
| EMB271 | MAThis3Δ1 leu2Δ0 met15Δ0 ura3Δ0 rad51::kanMX ARS1516-URA3-ADE2 | rad51Δ | Case-I URA3-ADE, rad51 knockout | This Study |
| EMB272 | MAThis3Δ1 leu2Δ0 met15Δ0 ura3Δ0 rad52::kanMX ARS1516-URA3-ADE2 | rad52Δ | Case-I URA3-ADE, rad52 knockout | This Study |
| EMB273 | MAThis3Δ1 leu2Δ0 met15Δ0 ura3Δ0 rad59::kanMX ARS1516-URA3-ADE2 | rad59Δ | Case-I URA3-ADE, rad59 knockout | This Study |
| EMB392 | MAThis3Δ1 leu2Δ0 met15Δ0 ura3Δ0 rad59::kanMX ARS1516-URA3-ADE2 pRCVS6H-pTEF1-RAD51 | rad59Δ | Case-I URA3-ADE, rad59 knockout, Rad51 overexpression | This Study |
| EMB393 | MAThis3Δ1 leu2Δ0 met15Δ0 ura3Δ0 rad59::kanMX ARS1516-URA3-ADE2 pRCVS6H-pTEF1-RAD52 | rad59Δ | Case-I URA3-ADE, rad59 knockout, Rad52 overexpression | This Study |
| EMB394 | MAThis3Δ1 leu2Δ0 met15Δ0 ura3Δ0 rad59::kanMX ARS1516-URA3-ADE2 pRCVS6H-pTEF1-RAD59 | rad59Δ | Case-I URA3-ADE, rad59 knockout, Rad59 overexpression | This Study |
| EMB395 | MAThis3Δ1 leu2Δ0 met15Δ0 ura3Δ0 rad59::kanMX ARS1516-URA3-ADE2 pRCVS6H-pTEF1-BETA | rad59Δ | Case-I URA3-ADE, rad59 knockout, Beta overexpression | This Study |
| EMB317 | MAThis3Δ1 leu2Δ0 met15Δ0 ura3Δ0 ARS1516-URA3-ADE2 pRCVS6H-pTEF1-RAD51 | EMB101 | Case-I URA3-ADE, Rad51 overexpression | This Study |
| EMB318 | MAThis3Δ1 leu2Δ0 met15Δ0 ura3Δ0 ARS1516-URA3-ADE2 pRCVS6H-pTEF1-RAD52 | EMB101 | Case-I URA3-ADE, Rad52 overexpression | This Study |
| EMB319 | MAThis3Δ1 leu2Δ0 met15Δ0 ura3Δ0 ARS1516-URA3-ADE2 pRCVS6H-pTEF1-RAD59 | EMB101 | Case-I URA3-ADE, Rad59 overexpression | This Study |
| EMB112 | MAThis3Δ1 leu2Δ0 met15Δ0 ura3Δ0 msh2::kanMX URA3-RPL28 | msh2Δ | Case-I URA3-RPL28, msh2 knockout | This Study |
| EMB114 | MAThis3Δ1 leu2Δ0 met15Δ0 ura3Δ0 msh2::kanMX RPL28-URA3 | msh2Δ | Case-II URA3-RPL28, msh2 knockout | This Study |
| EMB285 | MAThis3Δ1 leu2Δ0 met15Δ0 ura3Δ0 ARS1516-URA3-crtE-crtI-crtYB-tHMG1-ADE2 | BY4741 | Case-I URA3-Beta Carotene Pathway | This Study |
| EMB294 | MAThis3Δ1 leu2Δ0 met15Δ0 ura3Δ0 ARS1516-URA3-crtE-crtI-crtYB-tHMG1-ADE2 msh2::hphMX | EMB285 | Case-I URA3-Beta Carotene Pathway, msh2 knockout | This Study |
| EMB296 | MAThis3Δ1 leu2Δ0 met15Δ0 ura3Δ0 ARS1516-URA3-1-crtI-crtYB-tHMG1-ADE2 msh2::hphMX | EMB294 | Strain expressing crtI, crtYB, and tHMG1 | This Study |
| EMB297 | MATαhis3Δ1 leu2Δ0 met15Δ0 ura3Δ0 ARS446-URA3-crtE | BY4741 | Case-I URA3-crtE at Origin ARS446, Mating Type α | This Study |
| EMB298 | MATαhis3Δ1 leu2Δ0 met15Δ0 ura3Δ0 ARS510-URA3-crtE | BY4741 | Case-I URA3-crtE at Origin ARS510, Mating Type α | This Study |
| EMB299 | MATαhis3Δ1 leu2Δ0 met15Δ0 ura3Δ0 ARS702-URA3-crtE | BY4741 | Case-I URA3-crtE at Origin ARS702, Mating Type α | This Study |
| EMB301 | MATαhis3Δ1 leu2Δ0 met15Δ0 ura3Δ0 ARS446-URA3-crtE msh2::hphMX | EMB297 | Case-I URA3-crtE at Origin ARS446, Mating Type α, msh2 knockout | This Study |
| EMB302 | MATαhis3Δ1 leu2Δ0 met15Δ0 ura3Δ0 ARS510-URA3-crtE msh2::hphMX | EMB298 | Case-I URA3-crtE at Origin ARS510, Mating Type α, msh2 knockout | This Study |
| EMB303 | MATαhis3Δ1 leu2Δ0 met15Δ0 ura3Δ0 ARS702-URA3-crtE msh2::hphMX | EMB299 | Case-I URA3-crtE at Origin ARS702, Mating Type α, msh2 knockout | This Study |

Media

For general strain manipulation cells were grown in YPADU liquid medium, which consists of YPD (10 g/L Yeast Extract, 20 g/L Peptone, 20 g/L Dextrose), supplemented with 40 mg/L adenine hemisulfate, and 40 mg/L uracil. For URA3-coupled ssODN experiments (eMAGE), strains were grown in CSM-Ura medium during odd numbered cycles and CSM-Ura+5-FOA (1 g/L)+uracil (50 mg/L) medium during even numbered cycles. For HR gene overexpression experiments, CEN/ARS plasmids were maintained with the hygromycin B resistance marker. After electroporation, cells were allowed to recover in YPADU/ 0.5M Sorbitol (Recovery Medium).

Plasmid Assembly for Overexpression of HR Genes

To clone pTEF1 expression plasmids for HR genes, all HR gene ORFs were PCR amplified from BY4741 genomic DNA prepared via a standard glass bead yeast genomic preparation protocol. Forward primers for each ORF contained 40 bases of 5' overhang with sequence identity to 3' end of the TEF1 promoter. Reverse primers for each ORF contained 5' overhang with 40 bases of cyc1T terminator identity. Gibson assembly cloning was used to assemble a hygromycin B resistant (hphMX) CEN/ARS plasmid backbone (pRCVS6H) for each ORF to generate (pRCVS6H-pTEF1-ORF-CycT-hphMX plasmids). All HR plasmids were sequence verified.

Yeast ssODN Electroporation with Rad51-Dependent HR

A 2 mL culture was inoculated with a single colony and grown to saturation overnight in YPADU or YPADU+ Hygromycin B (200 ug/mL) for plasmid maintenance during HR overexpression experiments. The next day a 10 mL culture was inoculated at $OD_{600}$~0.1 and grown for 6 hours in a roller drum at 30° C. until $OD_{600}$~1.0 (~$3 \times 10^7$ cells/mL). Cells were pelleted at 2,900×g for 3 minutes and washed twice with 40 mL of room temperature $dH_2O$. Cells were pre-treated with 1 mL of TE pH 8 containing 500 mM Lithium Acetate/25 mM DTT (Pretreatment Buffer) for 30 minutes in the roller drum at 30° C. Cells were washed 1× with 1 mL ice cold $dH_2O$ and 1× with 1 mL ice cold 1M sorbitol. Cells were gently suspended in 200 uL of 1M sorbitol+2 uM of total ssODN for each transformation, and added to a pre-chilled electroporation cuvette (0.2 cm) on ice. 2 uM of ssODN was previously determined to be optimal for Rad51-dependent HR (DiCarlo et al., 2013). Electroporation was performed with the following parameters: 1500V, 25 uF, 200Ω. Immediately after pulsing, the cells were recovered in 6 mL of Recovery Medium for 12 hours in the roller drum at 30° C.

ssODN Transformations for eMAGE

A list of ssODNs used for FIGS. 1-4 in this study can be found in Table 2. For eMAGE experiments, a single colony was inoculated in 2 mL CSM-Ura medium and grown overnight to saturation. The next day the culture was diluted 1:50 in 10 mL of CSM-Ura and grown for 6 hours prior to electroporation. The ssODN concentration and size were determined from optimization experiments performed in Figure S2D,F. A total of 20 uM of 90nt ssODNs consisting of 50% selection ssODN 50% target ssODN(s) was used for eMAGE transformations. The optimal HU concentration was determined from figure S2A. The eMAGE pretreatment mixture contained 500 mM HU in TE pH 8/500 mM Lithium Acetate/25 mM DTT. Electroporation for eMAGE was performed exactly as described above. After 12 hours of recovery, ~$10^5$ cells were plated on 5-FOA selection plates for msh2Δ and MMR mutant strains and ~$10^7$ cells were plated for strains with WT MMR. The resultant 5-FOA plates contained ~100 colonies which were subject to screening for target ssODN incorporation. The indicated ARF values represent mean+/−SD. All data sets were collected in triplicate. For the Rad51 chemical inhibitor experiment (Figure S1J) the recovery medium was supplemented with inhibitor RI-1 (Abcam ab144558)+1.5% DMSO for solubility.

TABLE 2

List of ssODNs for RPL28, ADE2, and target distance experiments

| | RPL28, URA, and ADE2 ssODNs Targeting Leading and Lagging Strands |
|---|---|
| CyH90 | GGTAAGCACAGAAAGCACCCCGGTGGTAGAGGTATGGC CGGTGGTA AACATCACCACAGAATTAACATGGATAAATACCATCCA GGTTAT (SEQ ID NO: 1) |
| CyH90RC | ATAACCTGGATGGTATTTATCCATGTTAATTCTGTGGTG ATGTTTACC ACCGGCCATACCTCTACCACCGGGGTGCTTTCTGTGCTT ACC (SEQ ID NO: 2) |
| URA3190 | CGTGGATGATGTGGTCTCTACAGGATCTGACATTATTAT TGTTGAAAGAGGACTATTTGCAAAGGGAAGGGATGCTA AGGTAGAGGGTGA (SEQ ID NO: 3) |
| URA3190RC | TCACCCTCTACCTTAGCATCCCTTCCCTTTGCAAATAGT CCTCTTT AACAATAATAATGTCAGATCCTGTAGAGACCACATCAT CCACG (SEQ ID NO: 4) |
| ADE290 | GGCAGCAAACAGGCTCAACATTAAGACGGTAATACTAG ATGCTTAAAATTCTCCTGCCAAACAAATAAGCAACTCC AATGACCACGTTAA (SEQ ID NO: 5) |
| ADE290RC | TTAACGTGGTCATTGGAGTTGCTTATTTGTTTGGCAGGA GAATTTTAAGCATCTAGTATTACCGTCTTAATGTTGAGC CTGTTTGCTGCC (SEQ ID NO: 6) |
| His3gtoT | GGTCCCCTAGCGATAGAGCACTCGATCTTCCCAGAAAA AGAGGCAGAAGCAGTAGCAGAACAGGCCACACAATCG CAAGTGATTAACGTC (SEQ ID NO: 7) |

TABLE 2-continued

List of ssODNs for RPL28, ADE2, and target distance experiments

Multiplex Point Mutant ssODNs

| | |
|---|---|
| ADE2_Mult_1 | AATCATACGTCCCAATTGTCCCCCTCCTAATATACCAACTGTTCAAGAATCCATACTTGATTGTTTTGTCCGATTTTCTTGTTTTTCTTG (SEQ ID NO: 8) |
| ADE2_Mult_2 | TTACTTGAAGATTCTTTAGTGTAGGAACATCAACATGCTCAATCTAAATCGTTAGCACATCACATTTTTCAGCTAGTTTTTCGATATCAA (SEQ ID NO: 9) |
| ADE2_Mult_3 | CTATACCATTTTTGATTAAATGCTCTTTTTGAATATATTTGTCTTATATCAATCTGATTGTTTCTGGAGAAGGGTAAATTTTTAATTTGG (SEQ ID NO: 10) |
| ADE2_Mult_4 | ATGCCAAAGTCCTCGACTTCAAGACGAATGGAAAACCCAAATCTCATCCAACATTCAATAGGGACGTCTCACTGGCTTGTTCCACAGGAA (SEQ ID NO: 11) |
| ADE2_Mult_5 | ATTTTTCGGCGTACAAAGGACGATCCTTCAGTACTTCCAAAGCTTACGGAATCATTTCCTTATTCTTTACAACGAAGTTACCTCTTCCAT (SEQ ID NO: 12) |
| ADE2_Mult_6 | ACATAAGTCACAAATATTGTCCTTGTGGATAGTCTCTACAATTGGCTAAGAAAACACTAAACCGTTAACAGATCTCACAATCATGACTGC (SEQ ID NO: 13) |
| ADE2_Mult_7 | CCACACCAAATATACCACAACCGGGAAAAGATTTGATTGCATTTTATGCCAACAACTTCGCCTTAAGTTGAACGGAGTCCGGAACTCTAG (SEQ ID NO: 14) |
| ADE2_Mult_8 | GAGCTTCAAATTGAGAAGTGACGCAAGCATCAATGGTATAATGTCAAGAGTTGTGAGGCCTTGGGGCAATTTCGTTAATAAGCAATTCCC (SEQ ID NO: 15) |
| ADE2_Mult_9 | CCAATGCTCTTTCGCAAGTTTCTAGCTCTTTATCTTTTGTATGTTAGTCTCCAAGAACATTTAGCATAATGGCGTTCGTTGTAATGGTGG (SEQ ID NO: 16) |
| ADE2_Mult_10 | CACATTCCGCCATACTGGAGGCAATAATATTTATGTGACCTACTTATCTGTTAGGTCTAGACTCTTTTCCATATAAGTACACTGAGGAAC (SEQ ID NO: 17) |

Distance ssODNs

| | |
|---|---|
| 5distERI90RC | TCAAATTGATCCTCCAAATAACAGTTCACGAAATGCAAGTGAATTCTTGACCTCGGTATTGCATAGCCCAGTTTCTGTTAATATGAAAAA (SEQ ID NO: 18) |
| 10distERI90RC | ATTTGATGTTTCATATTTGTAAATAGATAGCAAAGTCGCCTCATTGAATTCGGAGATGTTACACTCTTTAGGGTTAATTTTAAACATTAA (SEQ ID NO: 19) |
| 15distERI90RC | ATAATTAGCGTCAATCAATAAAATATTTGTAAAATAGGAAGCGAATTCCCGCAGATGCCAGAATAGGTGGTGTATAAGGCAAGAAAACTT (SEQ ID NO: 20) |
| 20distERI90RC | CTGCTGTTTATCTCTTTATCACTTCAGAAAACTGACAAAGAAGAATTCTCCGAAGAAAGTGAAAACGACGGAAACAAGGAGTTGACTATA (SEQ ID NO: 21) |

Degenerate ADE2 ssODNs

| | |
|---|---|
| NADe2Mult 1 | CATACGTCCCAATTGTCCCCCTNCCTAATATACNCAACTGTTCTNAGAATCCATANCTTGATTGTTNTTGTCCGATTTTCTTGTTTTTCT (SEQ ID NO: 22) |
| NADe2Mult 2 | CTTGAAGATTCTTTAGTGTAGGNAACATCAACANTGCTCAATCTNCAATCGTTAGNCACATCACATNTTTTCAGCTAGTTTTTCGATATC (SEQ ID NO: 23) |
| NADe2Mult 3 | TACCATTTTTGATTAAATGCTCNTTTTTGAATANTATTTGTCTTNGTATCAATCTNGATTGTTTCTNGGAGAAGGGTAAATTTTTAATTT (SEQ ID NO: 24) |
| NADe2Mult 4 | CCAAAGTCCTCGACTTCAAGACNGAATGGAAAANCCCAAATCTCNTTCCAACATTNCAATAGGGACNGTCTCACTGGCTTGTTCCACAGG (SEQ ID NO: 25) |

TABLE 2-continued

List of ssODNs for RPL28, ADE2, and target distance experiments

| | |
|---|---|
| NADe2Mult 5 | TTTCGGCGTACAAAGGACGATCNCTTCAGTACTNTCCA AAGCTTNCCGGAATCATNTTCCTTATTCNTTTACAACGA AGTTACCTCTTCC (SEQ ID NO: 26) |
| NADe2Mult 6 | TAAGTCACAAATATTGTCCTTGNTGGATAGTCTNCTACA ATTGGNGTAAGAAAACNACTAAACCGTNTAACAGATCT CACAATCATGACT (SEQ ID NO: 27) |
| NADe2Mult 7 | CACCAAATATACCACAACCGGGNAAAAGATTTGNATTG CATTTTNCTGCCAACAANCTTCGCCTTANAGTTGAACGG AGTCCGGAACTCT (SEQ ID NO: 28) |
| NADe2Mult 8 | CTTCAAATTGAGAAGTGACGCANAGCATCAATGNGTAT AATGTCNCAGAGTTGTGNAGGCCTTGGGNGCAATTTCG TTAATAAGCAATTC (SEQ ID NO: 29) |
| NADe2Mult 9 | ATGCTCTTTCGCAAGTTTCTAGNCTCTTTATCTNTTTGTA TGTTNTGTCTCCAAGNAACATTTAGCNATAATGGCGTTC GTTGTAATGGT (SEQ ID NO: 30) |
| NADe2Mult10 | ATTCCGCCATACTGGAGGCAATNAATATTTATGNTGAC CTACTTNTTCTGTTAGGNTCTAGACTCTNTTTCCATATA AGTACACTGAGGA (SEQ ID NO: 31) |

Results

Recombinase proteins (e.g., Rad51) catalyze the pairing and exchange of homologous DNA sequences (San Filippo, et al., *Annual Review of Biochemistry*, 77:229-257 (2008)). In *S. cerevisiae* additional factors, including Rad52, Rad54, Rad55, Rad57, and Rad59 participate in HR by promoting the formation and stabilization of Rad51-ssDNA filaments or through annealing of ssDNA (San Filippo, et al., *Annual Review of Biochemistry*, 77:229-257 (2008); Sung, J Biol Chem, 272: 28194-28197 (1997)). Prior work proposed that ssODNs are incorporated in the yeast genome through Rad51-mediated HR (FIG. 1A) (DiCarlo, et al., *ACS Synth Biol*, 2:741-749 (2013); Liu, et al., *Nucleic Acids Research*, 32:2093-2101 (2004)). Experiments were designed to determine if ssODN-mediated recombination could be enhanced by increasing expression of HR genes and impairing MMR. Average recombination frequency (AFR) was measured for a ssODN containing a single base-pair mutation in the RPL28 gene, which confers cycloheximide resistance, for a panel of HR genes and MMR knockout strains (FIG. 1B). Overexpression of the three HR factors Rad51, Rad52 and Rad59 increased the ARF at least 10-fold above the empty vector control, with Rad51 and Rad52 producing the highest ARF (0.02%), followed by Rad59 (0.01%). Ablation of MMR led to ~100-fold enhancement above background (0.1%) in the strain msh2Δ (FIG. 1B). HR overexpression was next combined with MMR knockout strains (FIG. 1B). The combination of Rad51 overexpression in msh2Δ, msh6Δ, and mlh1Δ strains increased ARF four-fold above the level of the msh2Δ strain alone, yielding a maximum observed ARF of 0.4% that is consistent with previous reports (DiCarlo, et al., *ACS Synth Biol*, 2:741-749 (2013)). Taken together, these data indicate that ssODN incorporation by promoting Rad51-ssDNA invasion may be limited to the levels previously reported.

Experiments were designed to determine if Rad51-dependent ssODN recombination and incorporation of ssODNs at the DNA replication fork are two distinct pathways in eukaryotes (FIG. 1A). Unlike the *E. coli* chromosome, the linear chromosomes of *S. cerevisiae* contain multiple firing origins of replication that confound the precise designation of the lagging strand at each locus (Raghuraman, et al., *Science*, 294:115-121 (2001); Wyrick, et al., Science, 294: 2357-2360 (2001)). Sherman and colleagues observed high frequencies of co-transformation for two ssODNs targeted within a cyc1 mutant gene when one of the ssODNs included a selectable mutation (Yamamoto, et al., Yeast, 8:935-948 (1992a)). This observation indicates that the two ssODNs were incorporated at the same DNA replication fork. An analogous replication fork selection strategy resulted in improved recovery of edited *E. coli* cells (Carr, et al., *Nucleic Acids Research*, 40:e132 (2012)). Experiments were designed to determine whether Sherman's observation could be expanded for ssODNs targeting multiple proximal genes by constructing an experimental locus on chromosome XV with a defined DNA replication direction by placing the URA3 gene proximal to the origin ARS1516 (Ori) directly adjacent to ADE2, which confers a colorimetric phenotype (WT=white; Mutant=red) (FIG. 1C). Cells were transformed with ssODNs targeting the predicted lagging strand of both URA3 and ADE2, and it was observed that ssODN-derived modifications at ADE2 were increased by >$10^4$-fold (ARF=22%) in URA3-edited (5-FOA resistant) clones (FIG. 1C). To determine if the observed mode of ssODN incorporation requires targeting within the same replication fork, a marker-target (RPL28-ADE2) pair separated on different chromosomes was tested. ssODN incorporation at RPL28 were selected for with cycloheximide resistance and the resultant clones were screened for ssODN incorporation at ADE2. Targeted mutations in ADE2 were recovered with low ARF (0.4%), and overexpression of Rad51 led to a ~75% enhancement (0.7%). Taken together, the enrichment for ADE2 mutations in clones edited in proximity to URA3 indicated that the ssODNs were incorporated at the same DNA replication fork.

To assess the impact of HR factors on the proposed replication fork annealing mechanism, a set of knockout and overexpression strains for HR genes were created and ssODN incorporation at the Ori-URA3-ADE2 experimental locus was assayed. Unlike the observation for targeting the RPL28-ADE2 interchromosomal pair, overexpression of Rad51 decreased ARF to ~5% (four-fold) and deletion of Rad51 increased ARF to ~30% (FIG. 1D). In a further test of the counteracting effect of Rad51 on ssODN annealing, ARF enhancement was observed with the Rad51 inhibitor RI-1. Knockout or overexpression of Rad52 yielded no significant ARF change. Deletion of Rad59 ablated the recovery of 5-FOA resistant colonies and overexpression of Rad59 decreased ARF by 25%. A partial rescue of the Rad59 knockout was observed by pTEF1 expression of Rad51, Rad52, and the lambda red SSAP-Beta (FIG. 1E). In summary, depletion of Rad51 increases ssODN incorporation at the replication fork, and the replication fork annealing mechanism is distinct from Rad51-mediated ssODN recombination.

To further elucidate the mechanism of ssODN incorporation at the replication fork, the effect of targeting the leading versus lagging strands by placing URA3 was tested in two orientations with respect to ADE2 (FIG. 1F). In Case I, URA3 and ADE2 reside on the same side of the bidirectional replication fork such that they are replicated in the same replication fork. In Case II, URA3 and ADE2 are replicated in opposing directions. The four possible leading-lagging strand target combinations were tested in a set of WT (BY741) and MMR mutant strains (msh2Δ, msh6Δ, mlh1Δ, and pms1Δ) (FIG. 1F), in which WT and msh2Δ strains had the highest observed ARFs. The replication fork annealing model predicts the highest ARFs for ssODNs targeting the same chromosomal strand; whereas ssODNs targeting different chromosomal strands will be segregated to separate cells after division. In addition, the model predicts higher ARFs for targeting the lagging strand due to the prevalence of available ssDNA at the lagging strand. Consistent with this model, it was observed that the lag-lag (URA3-ADE2) strand combination for Case I was most efficient in all strains (Case-I b), followed by the lead-lead combination (Case-I c); both of which result in co-segregation of the ssODN-derived allele to the same daughter cell (FIG. 1F). The observed ARFs for lag-lead (Case-I a) and lead-lag (Case-I d) combinations indicate that the ssODNs can persist for more than a single cell cycle, namely that URA3 and ADE2 were edited during multiple replication events. For these scenarios, ssODN incorporation was observed at the ADE2 lead strand with lower ARFs than the ADE2 lag strand, which is consistent with reported strand biases (Yamamoto, et al., Genetics, 131:811-819 (1992b)). For Case II, the highest ARFs for ssODNs targeting the co-segregating strands (Case-II a,d) was again observed, and the ADE2 lead strand (Case-II c) with lower ARFs than the ADE2 lag strand (Case-II b) was again observed. To validate these findings, equivalent strand biases for both Case I and Case II was observed for a distal locus (RPL28) on chromosome VII.

Example 2: Manipulation of Replication Fork Speed can be Used to Modulate Diverse Genetic Changes and Target Distance Effects Materials and Methods
Target Distance Efficiency Determination
Target mutation distance is reported as the distance between the URA3 marker mutation incorporated by the selection-ssODN and the mutation incorporated by the target-ssODN. For target distances of 1 and 2 kb, ssODNs ADE290RC and ADE2_Mult10 were used within the ADE2 gene and the ARFs for these sites were determined by red/white phenotype screening. For targets at 5, 10, 15, and 20 kb distances from the Ori-URA3, target sites were chosen that differ by only a single base-pair from an EcoRI restriction site. The target ssODN was designed to incorporate a base-pair change to create the EcoRI restriction site. For each target assayed, 96 clones were analyzed by colony PCR (Primers for the amplicons analyzed are listed in Table 3) coupled to EcoRI (NEB) digestion of the amplicon for 1 hr at 37° C. The percentage of amplicons cut vs. uncut is represented as the ARF for each distance site. Each distance experiment was performed in triplicate+/−HU treatment. ARF values represent mean+/−SD.

Results
Hydroxyurea (HU) has been shown to slow the rate of DNA replication fork progression and increase the availability of ssDNA at the lagging strand (Alvino, et al., Mol Cell Biol, 27: 6396-6406 (2007)). Experiments were designed to determine if transient treatment with HU would increase the efficiency for ssODN annealing at the replication fork. A 30 minute treatment with 500 mM HU increased the ARF by ~two-fold compared to the untreated condition. Seven different ssODNs containing a single base-pair mismatch (ssODNs 1,2,5-7), insertion (ssODN #4), or deletion (ssODN #3) in ADE2 were tested and an average ARF increase of 56% (FIG. 2A) was observed. There was no significant increase in spontaneous URA3 mutations with the transient HU treatment. The HU effect was also observed using a HIS3 selection marker in replace of URA3. The effect of ssODN size and concentration was also tested. Robust cell survival post electroporation (85%) was tested for ssODN concentrations up to 20 uM, which decreased to 45% at 80 uM ssODN. The efficiency of URA3 single-plex targeting increased with increasing ssODN size and concentration with the highest ARF observed (0.08%) for 100nt ssODN at 60 uM. For coupled ADE2-URA3 targeting an optimum ade2 mutant per 5-FOA CFU was determined using a 90nt ssODN at 20 uM. For all subsequent experiments 90nt ssODNs at 20 uM were used.

Figure 2C:
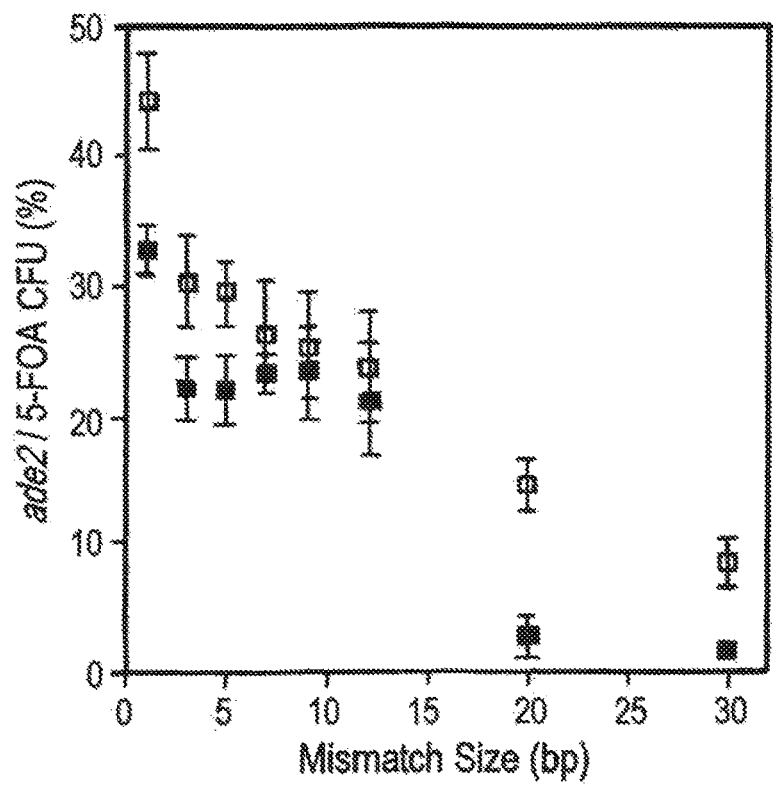
Figure 2D:
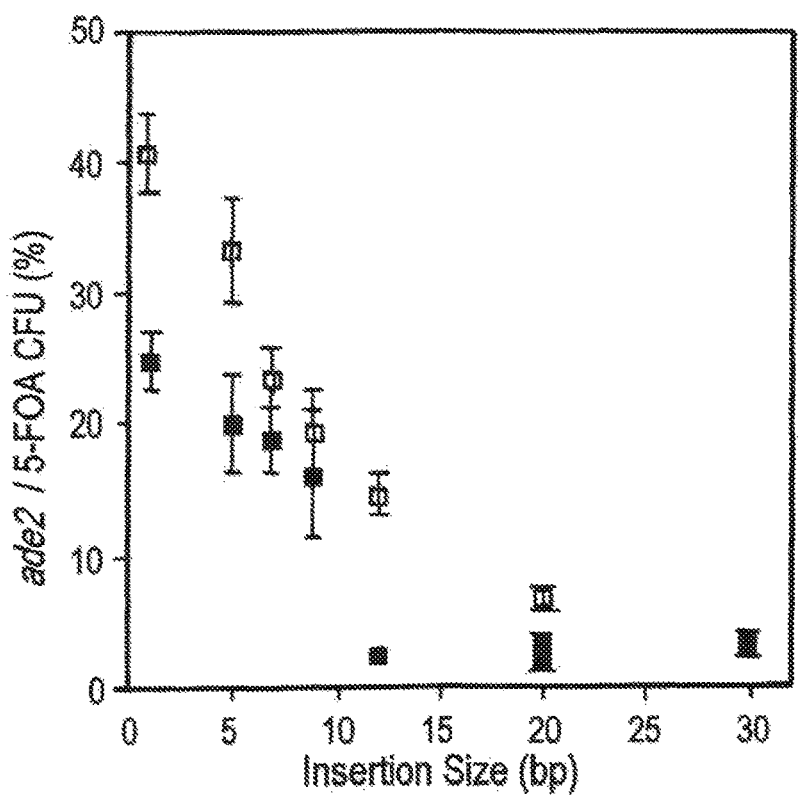
Figures 2E, 2F:
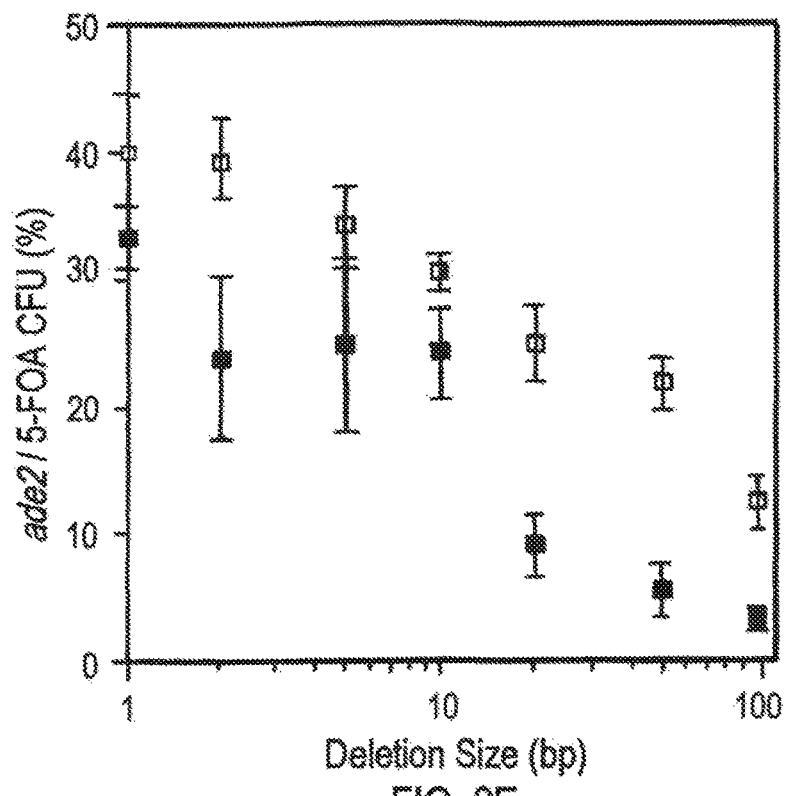
FIG. 2E is a plot showing the Hybridization free energy correlated to the average ARF for all ssODNs tested in FIG. 2B-2D with linear regression Pearson correlation coefficients indicated.
FIG. 2F is a plot showing ARF for increasing target site distances from the URA3 marker (Table S3). Curves represent ARF curve fit using GraphPad Prism 6 software non-linear curve fitting one-phase decay equation: $Y=(Y0-Z)*\exp(-K*X)+Z$; (+HU: Y0=49.6, Z=2.25, K=0.279), (−HU: Y0=38.7, Z=2.22*e$^{-16}$, K=0.2826) Values represent mean+/−SD.

To determine the ability to introduce diverse genetic mutations at the replication fork, a set of ssODNs containing mismatches, insertions, and deletions within ADE2 (msh2Δ strain) were tested. ARFs were inversely correlated to the number of nucleotides targeted for modification. More specifically, a single base-pair mismatch, insertion, or deletion was incorporated with an ARF>40% (FIGS. 2B-2D). Mismatches of up to 30 base-pairs and deletions up to 100 base-pairs were incorporated at ~10% efficiency (FIGS. 2B and 2D). Insertions are the least efficient modification with ARFs≤10% for insertion sizes greater than 12 base-pairs (FIG. 2C). The two-state hybridization free energy between the ssODN and genomic target sequence was a better predictor of ARFs for ssODNs tested in the +HU condition than −HU (FIG. 2E) (Markham, et al., Methods Mol Biol, 453:3-31 (2008)). ARFs decreased exponentially for targets at increasing distances from the Ori-URA3 locus (FIG. 2F; Table 2). Since yeast origins are ~30 kb apart the decrease in ARF with target distance from the Ori-URA3 locus could be due to interference of replication from adjacent origins. Together, these data demonstrate that ssODN annealing at the replication fork is enhanced in close proximity to the Ori-URA3 locus, and can generate a wide range of mutations required for precision genome editing.

Example 3: Precise Combinatorial Genome Modifications can be Generated Via Multiplexing and Cycling Materials and Methods
Multiplex Incorporation of ssODNs and Cycling
For multiplex eMAGE experiments targeting ADE2, red clones that grew on 5-FOA plates were assayed via yeast colony PCR and Sanger sequencing (Genewiz). Insertions were chosen for easy sequence detection since degenerate mismatches would contain WT sequence positions. For cycling experiments, cells were recovered in recovery media after electroporation as described above. After recovery, the population was subjected to liquid selection in 5-FOA for odd cycles and CSM-Ura for even numbered cycles to enrich for edited clones. Selections were performed for 500 uL of recovery culture seeded into 50 mL of selection medium and grown to saturation at 30° C. (~2 days).

After the first 1:100 selection the population was diluted 1:50 in selection media and grown for 6 hours for the next electroporation step. The process was repeated for 3 cycles. A total of 100 red clones were sequenced after each cycle. For cycles 1 and 2, 200 unique genotypes were observed out of 200 sequenced, but for cycle 3, 76 unique genotypes were observed out of the 100 clones sequenced. Given that the degeneracy of the ssODN pool largely out-scales the number of clones assayed redundant genotypes would not be expected to arise for independent clones in any cycle assayed. The 24 redundant clones observed in cycle 3 were comprised of 5 genotypes. These clones observed in cycle 3 are due to an enrichment of those genotypes that occurred from selection after cycle 2. For future experiments improved selection capabilities are highly desired in order to ensure maintenance of high population diversity between multiple cycles. For the purposes of this small-scale demonstration the liquid selections were seeded with ~$10^3$-$10^4$ edited genotypes between each cycle. For applications requiring large library sizes, larger scale selections (Liters) could be employed to maintain the population complexity generated after electroporation.

Results

Figure 3A:
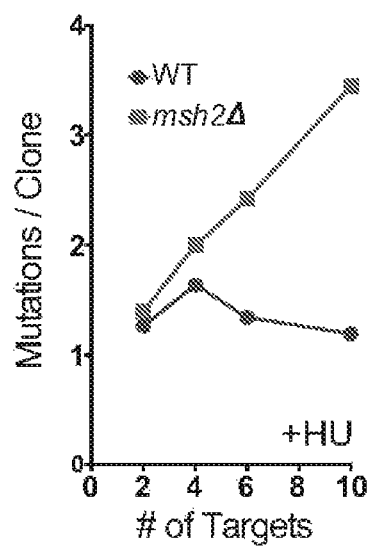
FIG. 3A is a line graphs showing multiplexed ssODNs harboring single point mutations across ADE2. Pools of 2, 4, 6, and 10 ssODNs with hydroxyurea (HU) in msh2Δ compared to WT (average mutations per clone).

To determine if multiple ssODNs can be introduced via annealing at the replication fork, 10 loci across the ADE2 gene in WT and msh2Δ strains (FIG. 3A; Table 2). The average number of ssODNs incorporated per clone was higher in msh2Δ (2.2 per clone) than WT (1.2 per clone). The effect of HU on ssODN multiplexing was tested on ssODN pools targeting 2-, 4-, 6-, and 10-sites across the ADE2 gene with HU (FIG. 3A). For 10-target multiplexing, HU increased the mean number of ssODNs incorporated in msh2Δ to 3.4 per clone, whereas WT exhibited no multiplex enhancement with HU. The mean number of ssODNs incorporated per clone plateaued at ~1 mutation per clone for WT and increased as a function of the number of target loci for msh2Δ (FIG. 3A). Clones were observed with diverse combinations of targeted changes for all multiplex pools. Notably, C-C mismatch mutations at position 6 were enriched by an average of 7.3-fold in WT cells, which is consistent with prior work showing that C-C mismatches evade MMR (Detloff, et al., *Mol Cell Biol*, 11:737-745 (1991)).

Figure 3B:
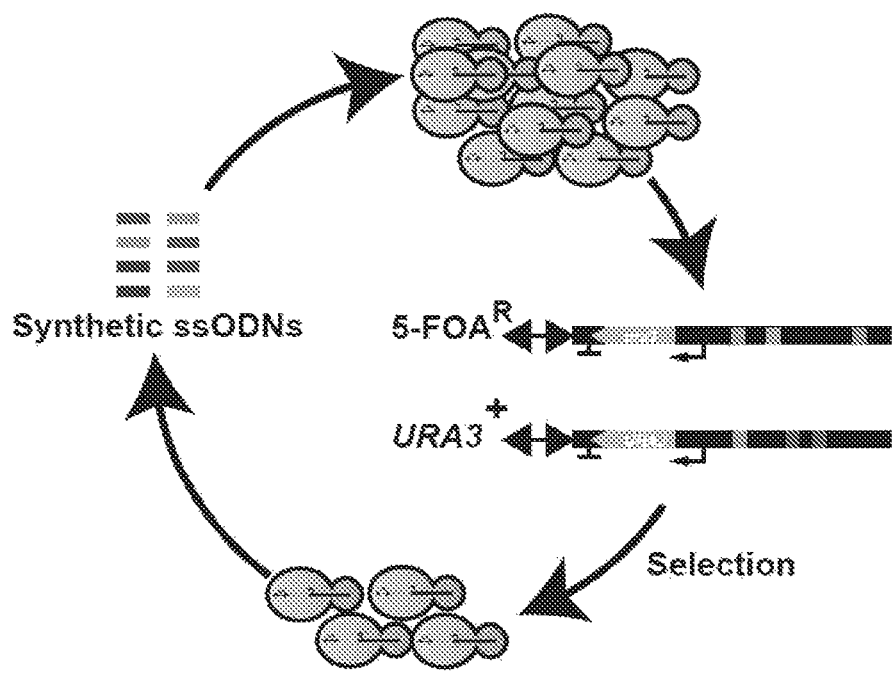
FIG. 3B is a diagram illustrating iterative cycling of ssODNs to a population of cells. URA3 is targeted by an 'OFF' ssODN in odd cycles and an 'ON' ssODN in even cycles. Positive-negative selections enable recovery of diversified chromosomes.

To further increase the rate and accumulation of genetic diversity, a strategy was developed for continuous diversification of a yeast cell population by cyclical introduction of a complex pool of ssODNs coupled to positive and negative URA3 selections (FIG. 3B). For odd numbered cycles, the selection-ssODN creates a non-sense mutation in URA3 for negative selection with 5-FOA, and the even cycle selection-ssODN restores the functional URA3 gene for positive selection in uracil-dropout media. A set of 10 ssODNs containing 5 degenerate ('N') insertion positions across each ssODN were designed, establishing a pool with theoretical complexity >$10^{30}$. 100 ade2 clones were analyzed by Sanger sequencing after each cycle, and a broad distribution of ade2 genotypes was observed. For each ssODN position, a range of 1 to 5 mutations was incorporated even though all ssODNs were designed to contain five degenerate insertions. Prior work (Rodriguez, et al., *PloS One*, 7:e42905 (2012)) implicated the Fen1-endonuclease in flap degradation at the 5' end of ssODNs. Consistent with this observation mutations closer to the 3' end of the ssODN were enriched more than 5' mutations by an average of 69%. This effect may be due to truncated ssODNs arising from errors in DNA synthesis. Transformation of PAGE purified ssODNs reduced the 3' bias. After 3 cycles, the maximum number of mutations increased from 37 to 42 per clone and the average number of mutations increased from 14.4 to 20.4 per clone. The average number of ssODNs incorporated increased from 5.1 to 6.0 ssODNs per clone (Table 3). 100% of the sequenced clones contained unique genotypes in cycles 1 and 2, and 76% were unique in cycle 3. Taken together these data illustrate the ability to rapidly create combinatorial genomic diversity by iterative incorporation of a complex pool of ssODNs at the replication fork.

TABLE 3

Statistics associated with cycling experiment

| Mutations per clone | Cycle 1 | Cycle 2 | Cycle 3 |
| --- | --- | --- | --- |
| Total number of Clones Analyzed | 100 | 100 | 76 |
| Minimum | 1 | 1 | 1 |
| 25% Percentile | 6 | 11 | 14 |
| Median | 15 | 19 | 22 |
| 75% Percentile | 21 | 27.75 | 29 |
| Maximum | 37 | 41 | 42 |
| Mean | 14.37 | 18.89 | 20.9474 |
| Std. Deviation | 9.15705 | 11.005 | 10.4854 |
| Lower 95% CI of mean | 12.553 | 16.7064 | 18.5513 |
| Upper 95% CI of mean | 16.187 | 21.0736 | 23.3434 |
| ssODNs per clone | Cycle 1 | Cycle 2 | Cycle 3 |
| Total number of Clones Analyzed | 100 | 100 | 76 |
| Minimum | 1 | 1 | 1 |
| 25% Percentile | 2 | 4 | 4 |
| Median | 5 | 7 | 7 |
| 75% Percentile | 8 | 8 | 9 |
| Maximum | 10 | 10 | 10 |
| Mean | 5.05 | 6.02 | 6.18421 |
| Std. Deviation | 2.72428 | 2.82836 | 2.70659 |
| Lower 95% CI of mean | 4.50944 | 5.45879 | 5.56573 |
| Upper 95% CI of mean | 5.59056 | 6.58121 | 6.80269 |

Example 4: eMAGE Protocol does not Increase Background Mutation Rate

The msh2Δ strain was shown to have a background mutation rate that is elevated ~225-fold greater than the WT yeast strain (Lang, et al., *G3 (Bethesda)*, 3:1453-1465 (2013)). Throughout the process of eMAGE cells can be grown for as many as hundreds of generations and are exposed to relatively higher stress conditions such as DTT-HU treatment, electroporation, and osmotic stress. In order to understand the effect of the eMAGE protocol on the background mutation rate whole genome sequencing was performed for 12 clones from each eMAGE cycle. In accordance with the previously reported mutational rate from (Lang, et al., *G3 (Bethesda)*, 3:1453-1465 (2013)) ($7.1 \times 10^{-8}$) for the msh2Δ strain, an average mutation rate of $8.3 \times 10^{-8}$ mutations per base pair per generation was observed. The majority of mutations were indels (80%) compared to SNPs (20%). The average SNP rate across the three cycles ($1.7 \times 10^{-8}$) was approximately four-fold greater than the published rate ($4.0 \times 10^{-9}$).

Example 5: eMAGE Created Diverse Populations

Materials and Methods

Generation of Mutant Population for NGS Diversity Analysis

Approximately $3 \times 10^8$ cells were electroporated in a 20 uM solution containing ssODNs designed to introduce insertions at targeted sites. Three ssODNs each encoding five insertions were pooled together. After electroporation and recovery the entire population was then seeded in 1 L of liquid 5-FOA selection media and grown to saturation over 2 days. 10 mL of this selected population was used for the genome prep and bug or approximately $5 \times 10^9$ genomic copies were seeded into the PCR reaction.

NGS Diversity Sample Preparation and Sequencing

A 307-322 bp region (depending on the number of insertions introduced) including the bases targeted for mutagenesis was PCR amplified with primers that added five degenerate base pairs on each end. The addition of degenerate bases aided in initial base calling during sequencing and reduced the need to add an increased fraction of phiX DNA (Tewhey et al 2016) The number of PCR cycles was limited to 12 in order to reduce the introduction of errors and bias. The PCR product was then gel purified and sent to the Yale Center for Genome Analysis for adaptor ligation and 2×250 paired end sequencing on an Illumina HiSeq4000. This allowed for coverage of the entire amplicon and sufficient overlap between the paired end reads to assemble phased sequences for each observed variant.

NGS Diversity Filtering and Processing of Paired End Reads into Merged Sequences The sequencing process generated 49,714,782 paired end reads. Trimmomatic was used to remove the first five degenerate bases added by the primers and trim reads with low quality bases (Bolger, A. M., Lohse, M., & Usadel, B. (2014). A sliding window requiring an average quality score of either 20, 25, or 30 over two bases was used to trim the ends of lower quality reads. This resulted in 49,384,456, 48,711,289, and 47,505,196 paired end reads respectively passing quality control. BBMerge was then used to assemble the overlapping paired end reads into full length amplicons. The "strict" stringency setting was used during this step. This resulted in 37,227,893, 24,116,204, and 12,065,464 fully assembled amplicons of which 16,704,731, 12,952, 187, and 9,048,602 were wild type length of 307 bp. BBMerge seeks to reduce the error rate in the assembled amplicons by considering the quality score of the bases in the overlapping sequences during merging and when there is a mismatch between the two reads selecting the base with the higher quality score. Similar numbers of reads pass the quality trimming step at Q20 and Q30, but the number of assembled amplicons is dramatically different between the two cutoffs. This indicates that while a large number of reads are passing quality control at Q30 they are being trimmed to a greater extent and this is resulting in read pairs that no longer overlap and are unable to be assembled.

NGS Diversity Computational Analysis

The merged reads were then arranged in the same orientation and aligned to a wildtype copy of the edited genomic locus using the BWA mem algorithm (Li, et al., *Nucleic Acids Research*, 31:6674-6687 (2003)). Picard tools were used to calculate the experimental substitution error rate. Custom scripts then utilized the CIGAR and MD strings in the resulting SAM file to extract the position and base introduced when insertions occurred at the targeted sites. Calculations of the distribution of the number of insertions introduced and the positional insertion distribution were then performed on these vectors containing the base introduced by each targeted insertion in an amplicon.

Results

In order to quantify the genetic diversity generated by an eMAGE experiment, Next-Generation Sequencing (NGS) was performed on a diversified cell population. To a starting population of approximately $3 \times 10^8$ cells were transformed with a pool of three ssODNs each encoding five degenerate insertions at ADE2. After electroporation and recovery in nonselective media the entire population was seeded in liquid 5-FOA selection media and grown to saturation. A genomic prep from the 5-FOA selected population served as the template for a PCR reaction of the ADE2 target region. High-throughput sequencing reads of the target amplicon were analyzed with a computational pipeline including rarefaction analysis (Amiram, et al., *Nature Biotechnology*, 33:1272-1279 (2015)). The number of unique variants detected at the read limit was $\sim 1.59 \times 10^5$ and $\sim 6.70 \times 10^5$ for read quality score cutoffs of Q30 and Q20, respectively. In line with the Sanger sequencing data a distribution of insertions per ssODN and a 3' position insertion bias were observed.

Example 6: eMAGE is Effective for Targeted Diversification of a Heterologous Biosynthetic Pathway Materials and Methods HPLC Characterization of Carotenoids Each of the analyzed clones was grown for 3 days at 30° C. in 5 mL YPADU media. Carotenoids were harvested from 1 mL of cell culture. 1 mL of cells was pelleted via centrifugation and washed twice with water. The resulting pellet was extracted with 200 uL of hexane using glass bead disruption with the Beadbeater cell homogenizer (3×45 s at 7,000 rpm). After centrifugation, 120 uL of the hexane carotenoid mixture was transferred to a glass vial and dried with a speedvac machine for 1 hour. The sample was then resuspended in 50/50 Hexane/Ethyl Acetate and filtered before HPLC analysis. 20 uL of sample was injected for HPLC using an Agilent Poroshell 120 EC-C18 2.7 um 3.0×50 mm column. Peaks were detected using an isocratic elution with 50/50 Methanol/Acetonitrile (containing 0.1% Formic Acid). Analytical standards were used for quantification of β-carotene (detected at 475 nm), phytoene (286 nm), and lycopene (475 nm). Carotenoid quantifications were calculated in relation to dry cell weight (DCW) for 100 uL of cell culture dried for 2 days and weighed. Additional carotenoid peaks were observed beyond the three carotenoid peaks analyzed, which likely contribute to clone color in some cases (i.e., M30, M35). HPLC experiments were carried out in technical triplicate for all clones.

Results

To further study the ability to generate multi-site combinatorial genetic variation with base-pair-level precision, a heterologous β-carotene pathway was targeted for the creation of diverse genotype-phenotype variants. The pathway consists of four constitutively expressed genes (crtE, crtI, crtYB, and tHMG1), and was previously engineered in *S. cerevisiae* to convert farnesyl diphosphate (FPP) to β-carotene through a series of enzymatic steps (FIG. 4A) (Mitchell, et al., *Nucleic Acids Research*, 43:6620-6630 (2015); Verwaal, et al., Appl Environ Microbiol, 73:4342-4350 (2007)). ssODNs were designed to precisely target distinct genetic elements in promoters, open reading frames (ORFs), and terminators (FIG. 4B, Table 4 (below)) (Lubliner, et al., *Nucleic Acids Research*, 41:5569-5581 (2013); Raveh- Sadka, et al., *Nat Genet*, 44:743-750 (2012)). For promoters, annotated transcription factor binding sites (TFBS), TATA boxes, insertion of nucleosome-disfavoring $(dT)_{20}$ sequences were targeted, and the A and T sequence content were altered near the transcription start signal (TSS). Mutations to TFBS and TATA boxes were designed as 'N' degenerate and LOGO-inspired sequences to create the potential for both highly divergent sequences and single-base-pair changes. For each ORF, the ssODNs encoded an alternate start codon (GTG), a common codon mutation, a rare codon mutation, and a frame-shift knockout mutation. In addition to mutations that alter gene expression, a ssODN conferring a protein sequence change in the bifunctional enzyme crtYB lycopene-cyclase domain known to increase lycopene production was also included (Xie, et al., Metab Eng, 30:69-78 (2015)). Lastly, terminators were targeted at putative poly-A signal sites. Overall, the ssODN pool contained 74 ssODNs containing targeted mutations at 482 dispersed nucleotide positions at a theoretical complexity $>10^{174}$.

To understand the phenotypic contribution from each of the four pathway genes, a complete set of the 15 possible combinatorial gene knockouts were generated in a single transformation. The lack of broad phenotypic diversity in the knockout set indicates that precise modifications to the pathway sequence might result in gene expression variants with color changes unlike the gene knockouts. Diverse clones with colorimetric phenotypes were observed to deviate from the ancestral strain after a single cycle of diversification (Figure S5B). Variants of diverse colorimetric phenotypes were selected for Sanger sequencing and HPLC analysis of phytoene, lycopene, and β-carotene levels and the analyzed clones contained a range of 1-60 base-pair changes and 1-12 ssODNs incorporated with a subset of the characterized clones highlighted. Many examples were observed of precise genetic modifications that resulted in distinct phenotypic variation. For example, three color variants contained mutations in the crtE gene element: an alternative start codon (M2), polyadenylation signal site insertion (M5), and a rare codon (M3) all with varied carotenoid levels different from the crtE knockout (KO1). Knockout of crtI (KO2) resulted in buildup of phytoene corresponding to a white phenotype, which was indistinguishable from a clone containing an alternate start and an abundant arginine codon in crtI (M1). In contrast, a deletion of 6 base-pairs in the crtI terminator (M39) resulted in β-carotene buildup and no detectable phytoene. Incorporation of nucleosome disfavoring poly$(dT)_{20}$ sequences in promoters for crtE and crtI resulted in ~7-fold increase in β-carotene production (M7), whereas an additional poly(dT)$_{20}$ in the promoter of crtYB led to detection of phytoene only (M6). Orange variants containing additional gene modifications combined with crtYB-D52G (M8-M13) were also recovered. Clone M11 contained a rare codon in crtE that resulted in a ~26% decrease in lycopene, and clone M10 was identical to M11 with an additional TATA box mutation in crtE that further reduced lycopene levels by ~60%. Clone M14 contained targeted mutations in all three classes of genetic elements targeted spanning all four genes (FIG. 4C, 4D). Many additional precisely edited clones were observed with a range of genotypes and phenotypes. To assess the background mutation rate and potential oligo off-target events whole genome sequencing was performed for 55 clones that arose after diversification. A similar mean mutation rate for these clones ($6.6 \times 10^{-8}$) was observed as was reported for the ADE2 cycling experiment. Since the engineered β-carotene pathway contains four promoters and three terminators found at native loci in the genome oligo incorporation was checked at these sites. No oligo-derived mutations were observed at these off-target sites. Taken together, the results demonstrate the ability to sample phenotypic variation through precision base-pair editing at pre-defined target sites, which could be applied to any set of genetic elements to elucidate causal links between genotype and phenotype.

Whether targeted edits in genes located on different chromosomes could be generated across haploids in parallel and then combined through mating was also tested. A MATα haploid were constructed containing the crtE gene adjacent to a URA3 cassette at Ori ARS510 on chromosome V, and a MATa haploid containing the crtI, crtYB, and tHMG1 genes at Ori ARS1516 on chromosome XV. Control mating was used to demonstrate that the resultant diploids showed the yellow phenotype indicative of the presence of all four genes of the wildtype β-carotene pathway (FIG. 4B). Next, parallel diversity of the haploids was generated with ssODN pools targeting the genes present in each strain, and lastly the populations were mated to generate diploid strains with diversified phenotypes resulting from the independent chromosomes targeted. The process was repeated for crtE at Ori ARS446 on chromosome IV and Ori ARS702 on chromosome VII and observed equivalent results. Importantly, these experiments demonstrate the generalizability of replication fork targeting of distinct loci on multiple chromosomes (IV, V, VII, and XV) in parallel across haploid strains and subsequent combining of the modified haploids in bulk to amplify combinatorial genetic variation in diploids.

Example 7: Transcriptional Logic can be Altered with ssODNs

Since ssODN annealing at the replication fork can enact a wide range of sequence modification, experiments were designed to determine whether ssODNs can be used to seamlessly replace promoter elements such as TFBS to change the transcriptional logic of constitutive promoters. A set of ssODNs was designed to precisely replace native TFBS of the β-carotene pathway with the 18 nucleotide galactose-inducible Gal4 binding sequence. Cells were transformed with the set of Gal4 ssODNs and an ssODN containing the crtYB-D52G mutation. Clones were identified with altered color phenotypes on glucose plates and these clones were inspected for phenotypic changes when spotted to plates containing galactose. Several clones with altered color phenotypes (G2-G6) and one clone (G1) with impaired growth on galactose were observed. To confirm that the different phenotypes observed on glucose and galactose corresponded to altered gene expression at the Gal4 engineered gene, RT-qPCR of the four pathway genes (FIG. 7C) was performed. In clone G4 a 1.3 fold-change in expression of crtE was observed. Expression of crtI in G5 was induced 12.3-fold, which was the strongest galactose gene induction in the tested clones. Clone G6 exhibited a 4.0-fold induction of crtYB-D52G, but also showed elevated expression of crtI, which did not contain an engineered Gal4 binding sequence. Elevated crtI expression was also observed in the WT ancestor. In all strains, low Gal4-based gene induction was observed compared to the native GALL Strains that contained Gal4 binding sites in pathway genes exhibited lower GAL1 induction, potentially due to competition from the additional Gal4 site. Taken together, the data show that eMAGE can introduce functional sequence elements that can impart galactose-induction logic in otherwise constitutive promoters. This strategy can be applied to many other transcriptional logic elements (e.g., tetO, lacI) and promoters.

In this study, a eukaryotic genome engineering technology was developed that targets annealing of ssODNs at the DNA replication fork and avoids the creation of DSBs in the genome to enact base-pair precision and combinatorial genome editing across many genetic loci. Although the mechanism is independent of Rad51, other HR factors could be involved in ssODN incorporation. In addition to its role as a mediator for Rad51 (Sung, *J Biol Chem*, 272: 28194-28197 (1997)), Rad52 is also implicated in replication fork processing of Okazaki fragments with Rad59 (Lee, et al., *J Biol Chem*, 289:15064-15079 (2014)). Thus, it is possible that Rad52 participates in ssODN annealing at the replication fork. The lack of transformants in the Rad59 knockout indicated that it enhances ssODN incorporation at the replication fork whereas overexpression of Rad59 showed a decrease in ARF (FIG. 1C). The partial rescue of the Rad59 knockout by Rad51 could be due to ssODN incorporation events occurring by Rad51-dependent HR in the absence of Rad59. The rescue by Rad52 and particularly the SSAP beta indicate that the strand-annealing function of Rad59 is important for ssODN incorporation process.

For single base-pair editing similar ARFs were observed in WT and msh2Δ strains, however, the data showed that MMR inhibits multiplex gene editing and therefore decreases the generation of genome complexity across the population. Although MMR mutants are not always desirable when trying to maintain genome stability, directed evolution and pathway engineering applications, as shown here, could benefit from an elevated mutation rate. Alternatively, transient disabling of MMR through small molecule inhibitors or CRISPRi (Gilbert, et al., *Cell*, 154:442-451 (2013)) approaches could be used to achieve desired genetic modifications during a transient relaxed genomic state (disabled MMR) followed by rapid return to a stabilized genomic state (intact MMR).

The approach to diversify the β-carotene pathway is also a blueprint that could be applied to metabolic engineering applications and natural product biosynthesis to optimize the production of high-value molecules from heterologous genetic sources currently produced in yeast (Galanie, et al., *Science*, 349:1095-1100 (2015); Krivoruchko, et al., *Curr Opin Biotechnol*, 35: 7-15 (2007); Mitchell, et al., *Nucleic Acids Research*, 43:6620-6630 (2015); Montiel, et al., *Proceedings of the National Academy of Sciences of the United States of America*, 112:8953-8958 (2015)). Large microbial gene clusters are often genetically silent and require modulation of pathway expression dynamics or refactoring to produce the desired secondary metabolites (Smanski, et al., Nature Biotechnology, 32:1241-1249 (2014)). Current methods to tune the expression of biosynthetic pathways in yeast rely on the use of combinatorial promoter swapping strategies (Mitchell, et al., *Nucleic Acids Research*, 43:6620-6630 (2015); Montiel, et al., *Proceedings of the National Academy of Sciences of the United States of America*, 112:8953-8958 (2015); Wingler, et al., Proceedings of the National Academy of Sciences of the United States of America, 108:15135-15140 (2011)). While promoter library approaches are effective, the possible modes of gene expression are limited to quantal units of transcription dictated by the promoter library. Precision editing with ssODNs in live cells enables rapid exploration of diverse gene expression states. Since CRISPR-Cas9 can efficiently introduce large genetic fragments into the genome and eMAGE can enact many precise combinatorial edits with ssODNs, the two approaches could be used in concert to recombine and diversify heterologous pathways for discovery and production of secondary metabolites and valuable compounds in yeast.

Eukaryotic MAGE can also uniquely enable the construction of targeted sets of genetic variants that can be functionally studied to elucidate causal links between genotype and phenotype. The diversification and mating studies established here could be automated (Wang, et al., Nature, 460:894-898 (2009)), employed to uncover many types of precise allelic interactions between specific sets of genes complementary to those explored by synthetic genetic arrays (Costanzo, et al., *Science,* 353 (2016); Tong, et al., Methods Mol Biol, 313:171-192 (2006)), and used to hierarchically construct highly modified chimeric genomes from multiple strains. Moreover, the approach used for *S. cerevisiae* targets conserved mechanisms and establishes a framework for developing efficient multiplex ssODN annealing methods in multicellular eukaryotes, including plants and animals. eMAGE capabilities could be included in future synthetic eukaryotic chromosome projects (Annaluru, et al., *Science*, 344: 55-58 (2014); Boeke, et al., *Science*, 353: 126-127 (2016)) to enable efficient single base-pair precision editing of designer genomes.

Table 4: List of ssODNs targeting the Beta Carotene pathway. Each targeted sequence is indicated with its WT sequence (Column 3) and the ssODN mutation design (Column 4), the type of sequence (Column 5), and notes on the mutation outcome (Column 6). Abbreviations: Transcription factor binding site (TFBS), Transcription start site (TSS). Mutation annotations for oligos: 'N'=mixed bases A,T,G,C; 'W'=mixed bases A,T; 'Y'=mixed bases C,T; 'R'=mixed bases A,G; 'K'=mixed bases G,T; 'M'=mixed bases A,C.

TABLE 4

List of ssODNs targeting the Beta Carotene pathway.

| ssODN Name | Promoter ssODNs (5' to 3') Reverse complement of top strand targeting the lagging strand. | WT Target Sequence Top Strand | Mutation Sequence Top Strand | Sequence Type | Description |
| --- | --- | --- | --- | --- | --- |
| PGKGcr1N | AAACCTGTGAGCCGTCGCTA GGACCTTGTTGTGTGACGAA ANNNNNNNNTGCAATCAAT AGGAAGACAGGAAGTCGAG CGTGTCTGGGTT (SEQ ID NO: 32) | GCTTCC AA | NNNN NNNN | TFBS | Degenerate Mismatch |

TABLE 4-continued

List of ssODNs targeting the Beta Carotene pathway.

| | | | | | |
|---|---|---|---|---|---|
| PGKMsrt2aN | ATGTAAATGTAAGTTTCACG AGGTTCTACTAAACTAAACC ACNNNNNNGGTTAGAAGAA AAGAGTGTGTGAGAACAGG CTGTTGTTGTCA (SEQ ID NO: 33) | AAGGGG | NNNN NN | TFBS | Degenerate Mismatch |
| PGKMsn2bN | GCTCTGGAGATCACAGTGG GCATCATAGCATGTGGTACT AAANNNNNCCCGCCATTC CAGAACCTTCGATTGCTTGT TACAAAACCTGT (SEQ ID NO: 34) | AAAGGG | NNNN NN | TFBS | Degenerate Mismatch |
| PGKTye7N | GACCAATTTATGCAAGTTTA TATATATGTAAATGTAAGTT TNNNNNNNNTTCTACTAAACT AAACCACCCCCTTGGTTAGA AGAAAAGAGT (SEQ ID NO: 35) | CCTCGT G | NNNN NNN | TFBS | Degenerate Mismatch |
| PGKHsf1N | GTGGGCATCATAGCATGTGG TACTAAACCCTTTCCCGCNN NNNNNNNNNNNNNGATTGC TTGTTACAAAACCTGTGAGC CGTCGCTAGGA (SEQ ID NO: 36) | GAAGGT TCTGGA ATG (SEQ ID NO: 101) | NNNN NNNN NNNN NNN (SEQ ID NO: 119) | TFBS | Degenerate Mismatch |
| TIP1phd1aN | GCTCGAAGAATTGGAGAGA AAAAAGATGCTTTTAGAA AATANNNNNNATTTCCCGG AACAATCAATTATTTCCATC ACAATCTTTGAAA (SEQ ID NO: 37) | GTGTCT | NNNN NN | TFBS | Degenerate Mismatch |
| TIP1phd1bN | GCCAATGTACTATTTATATT AAATGGTGAATGAAGCAAC GCANNNNNNCAAAGAGGTT GGAGACATATTCACCCTTAC AGCAAACCTTTT (SEQ ID NO: 38) | AGGTAC | NNNN NN | TFBS | Degenerate Mismatch |
| TIP1adr1N | ATATTAAATGGTGAATGAA GCAACGCAGTACCTCAAAG AGGNNNNNNNCATATTCAC CCTTACAGCAAACCTTTTTT TTCCTTTACTGGA (SEQ ID NO: 39) | TCTCCA A | NNNN NNN | TFBS | Degenerate Mismatch |
| TIP1rgt1N | GGATTCAAAACCACAAGTA CATTCTTCAACGGAAAAGA GTCNNNNNNNCGGAAAAGG GACCTCCCGAAGACATTAGT CTCATAATTAAGG (SEQ ID NO: 40) | ATTTTCC | NNNN NNN | TFBS | Degenerate Mismatch |
| TDH3Hsf1N | ACCTTTTTTTCAGCTTTTTC CAAATCAGAGAGAGCANNN NNNNNNNNNNNNTGTAAGA AAATGAGATAGATACATGC GTGGGTCAATTG (SEQ ID NO: 41) | CCTTCTA TTACCTT C (SEQ ID NO: 102) | NNNN NNNN NNNN NNN (SEQ ID NO: 119) | TFBS | Degenerate Mismatch |
| TDH3Pho2aN | AAACTAAAAAAAGACTAA CTATAAAGTAGAATTTAAG AAGNNNNNNAAATAGATTT ACAGAATTACAATCAATACC TACCGTCTTTAT (SEQ ID NO: 42) | CTTAAA | NNNN NN | TFBS | Degenerate Mismatch |
| TDH3Pho2bN | TGTTTGTTTATGTGTGTTTAT TCGAAACTAAGTTCTTGGTG TNNNNNNNACTAAAAAAAG ACTAACTATAAAGTAGAA TTTAAGAAGTT (SEQ ID NO: 43) | TTTAAA | NNNN NN | TFBS | Degenerate Mismatch |

TABLE 4-continued

List of ssODNs targeting the Beta Carotene pathway.

| | | | | | |
|---|---|---|---|---|---|
| TDH3Msn2aN | TTACAATCAATACCTACCGT CTTTATATACTTATTAGTCA AGNNNNNNAATAATTTCAG GGAACTGGTTTCAACCTTTT TTTTCAGCTTT (SEQ ID NO: 44) | CCCCTA | NNNN NN | TFBS | Degenerate Mismatch |
| TDH3Msn2bN | CATCACTCCATTGAGGTTGT GCCCGTTTTTTGCCTGTTTGT GNNNNNNTTCTCTGTAGTTG CGCTAAGAGAATGGACCTA TGAACTGATG (SEQ ID NO: 45) | CAGGGG | NNNN NN | TFBS | Degenerate Mismatch |
| TDH3OrIN | GTAGGGGAATAATTTCAGG GAACTGGTTTCAACCTTNNN NNNNNNNNNNNNNNAAATC AGAGAGAGCAGAAGGTAAT AGAAGGTGTAAGA (SEQ ID NO: 46) | GGAAAA AGCTGA AAAAA (SEQ ID NO: 103) | NNNN NNNN NNNN NNNN N (SEQ ID NO: 120) | TFBS | Degenerate Mismatch |
| ZEOgln3N | GAGCAAACCAGCATTAACT AAAGATGATAAAATAAAA TTNNNNNNNNNNCCTTAATT GGATATACAAAAATACACT GGAGGCACAAATC (SEQ ID NO: 47) | TTTCTTA CCT (SEQ ID NO: 104) | NNNN NNNN NN (SEQ ID NO: 121) | TFBS | Degenerate Mismatch |
| ZEOAce2N | AGAGAAGAGGAGAACCGCA CAGAAAGCAGCAGAAACAG AGCNNNNNNNCATTAACTA AAGATGATAAAATAAAAT TAGGTAAGAAACCT (SEQ ID NO: 48) | CTGGTTT | NNNN NNN | TFBS | Degenerate Mismatch |
| PGKTATN | ACCAAATATGTATTTCTTGC ATTGACCAATTTATGCAAGT TNNNNNNNNNGTAAATGTA AGTTTCACGAGGTTCTACTA AACTAAACCAC (SEQ ID NO: 49) | ATATAT ATA | NNNN NNNN N | TATA Box | Degenerate Mismatch |
| PGKTAT | ACCAAATATGTATTTCTTGC ATTGACCAATTTATGCAAGT TYWTWTATAGTAAATGTAA GTTTCACGAGGTTCTACTAA ACTAAACCAC (SEQ ID NO: 50) | TATA | WAWR | TATA Box | LOGO Mismatch |
| TIPTATN | AGCGAGAATAATTGACGTTT GAAAGAGGGCTGCCAATGT ACNNNNNNNNTTAAATGGT GAATGAAGCAACGCAGTAC CTCAAAGAGGTTG (SEQ ID NO: 51) | TATAAA TA | NNNN NNNN | TATA Box | Degenerate Mismatch |
| TIPTAT | AGCGAGAATAATTGACGTTT GAAAGAGGGCTGCCAATGT ACYWTWTATATTAAATGGT GAATGAAGCAACGCAGTAC CTCAAAGAGGTTG (SEQ ID NO: 52) | AATA | WAWR | TATA Box | LOGO Mismatch |
| TDH3TATN | TAAGAAATAGATTTACAGA ATTACAATCAATACCTACCG TCNNNNNNNNCTTATTAGTC AAGTAGGGGAATAATTTCA GGGAACTGGTTT (SEQ ID NO: 53) | TATATA AA | NNNN NNNN | TATA Box | Degenerate Mismatch |
| TDH3TAT | TAAGAAATAGATTTACAGA ATTACAATCAATACCTACCG TCYWTWTATACTTATTAGTC AAGTAGGGGAATAATTTCA GGGAACTGGTTT (SEQ ID NO: 54) | TAAA | WAWR | TATA Box | LOGO Mismatch |

TABLE 4-continued

List of ssODNs targeting the Beta Carotene pathway.

| | | | | | |
|---|---|---|---|---|---|
| ZEOTATN | CAAGCAAACTGAGATGATC TTCGACGTAAAAACTCGCTC NNNNNNNNNNCGCCATATA AGCCCATCGGCGATGGGGG ACAACACGAAGAA (SEQ ID NO: 55) | TATATAT ATA (SEQ ID NO: 105) | NNNN NNNN NN (SEQ ID NO: 121) | TATA Box | Degenerate Mismatch |
| ZEOTAT | CAAGCAAACTGAGATGATC TTCGACGTAAAAACTCGCTC YWTWTATACGCCATATAAG CCCATCGGCGATGGGGGAC AACACGAAGAA (SEQ ID NO: 56) | TATATAT A | TATA WAWR | TATA Box | LOGO Mismatch |
| PGKTSSup | GTTGTAAAAAGTAGATAATT ACTTCCTTGAWRAWMWRW AAAAAARARAAAAARAAAR MAWCTAAGAACTTGAAAAA CTACGAATTAGAAA (SEQ ID NO: 57) | ATGCTTT CTTTTTC TCTTTTT TACAGA TCA (SEQ ID NO: 106) | WTKY TTTYT TTTTY TYTTT TTTWY WKWT YW (SEQ ID NO: 122) | Upstream Region of Transcription Start Site | Increase T Content |
| TIP1TSSup | TTTATTTTATTTAGCAGAGG GTATAGTTATRMAAWARMA AWWAWWRWWAMWRAWW RAAWRCCTTTATAATTTCGG TCCGAACAAAGTTAG (SEQ ID NO: 58) | CATTCA ATCAGT AACAAT AATTGC TATTGC (SEQ ID NO: 107) | YWTT YWWT YWKT WWYW WTWW ttkyt WTTK Y (SEQ ID NO: 123) | Upstream Region of Transcription Start Site | Increase T Content |
| TDH3TSSup | ATGTGTGTTTATTCGAAACT AAGTTCTTGGWRWWWWAA AAMWAAAAAAAARAMWAA MWAWAAAAGTAGAATTTA AGAAGTTTAAGAAATA (SEQ ID NO: 59) | ATAGTT AGTCTTT TTTTTAG TTTTAAA ACA (SEQ ID NO: 108) | WTWK TTWKT YTTTT TTTTW KTTTT WWW WYW (SEQ ID NO: 124) | Upstream Region of Transcription Start Site | Increase T Content |
| ZEOTSSup | ATATAAACGTAGTTTTGTAT GTTTCTTTGAWWWRAAMW WWWAARWAWAMARARAA AAAAACCGATCAAAGAAAA CTAAAGTATAATGAGG (SEQ ID NO: 60) | CTCTGTA TACTTA AAAGTT CAAA (SEQ ID NO: 109) | YTYTK TWTW YTTW WWWK TTYW WW (SEQ ID NO: 125) | Upstream Region of Transcription Start Site | Increase T Content |
| PGKTSSdwn | TCTTGTTCTTTTCCCATTTGT TTATATTTKTTKTWWWWW KTWKWTWWTTWYTTYYTT KWTGATCTGTAAAAAAGAG AAAAAGAAAGCAT (SEQ ID NO: 61) | TCAAGG AAGTAA TTATCTA CTTTTTA CAACA (SEQ ID NO: 110) | WMAA RRAAR WAAW WAWM WAMW WWW WAMA AM (SEQ ID NO: 126) | Downstream Region of Transcription Start Site | Increase A Content |
| TIP1TSSdwn | ATTGCTGTGAGGATGTTCGC GTAATCCATTTTTWTTTTWT TTWKYWKWKKKTWTWKTT WTGCAATAGCAATTATTGTT ACTGATTGAATG (SEQ ID NO: 62) | TAACTA TACCCTC TGCTAA ATAAAA T (SEQ ID NO: 111) | WAAM WAWA MMM WMWR MWAA AWAA AAW (SEQ ID NO: 127) | Downstream Region of Transcription Start Site | Increase A Content |
| TDH3TSSdwn | ATATGCGAGAGCCGTCATTT TTGTTTGTTTWTKTKTKTTTT WTTYKWWWYTWWKTTYTT | CCAAGA ACTTAG TTTCGA | MMAA RAAM WWAR | Downstream Region | Increase A Content |

TABLE 4-continued

List of ssODNs targeting the Beta Carotene pathway.

| | | | | | |
|---|---|---|---|---|---|
| | KKTGTTTTAAAACTAAAAAA AAGACTAACTAT (SEQ ID NO: 63) | ATAAAC ACACAT A (SEQ ID NO: 112) | WWW MRAA WAAA MAMA MAW (SEQ ID NO: 128) | of Transcription Start Site | |
| ZEOTSSdwn | GTTTTCACCAATTGGTCCAT TTATTAATTGWTWTWWWY KTWKTTTTKTWTKTTTYTTT KWTTTGAACTTTTAAGTATA CAGAGAAAAAA (SEQ ID NO: 64) | TCAAAG AAACAT ACAAAA CTACGTT TATAT (SEQ ID NO: 113) | WMAA ARAAA MAWA MAAA AMWA MRWW WAWA W (SEQ ID NO: 129) | Downstream Region of Transcription Start Site | Increase A Content |
| PGKdAdT | TTTCACGAGGTTCTACTAAA CTAAACCACCCCCTTTTTTT TTTTTTTTTTTTTGGTTAGA AGAAAAGAGTGTGTGAGAA CAGGCTGTT (SEQ ID NO: 65) | CAAGGG | cAAAA AAAA AAAA AAAA AAAA AAGG G (SEQ ID NO: 130) | Upstream of TFBS | Poly dA/dT insertion |
| TIP1d<sub>4</sub>dT | AATGAAGCAACGCAGTACC TCAAAGAGGTTGGAGATTTT TTTTTTTTTTTTTTTCATATT CACCCTTACAGCAAACCTTT TTTTTCCTT (SEQ ID NO: 66) | T<sub>4</sub>TGTCT | TATGA AAAA AAAA AAAA AAAA AAATC T (SEQ ID NO: 131) | Upstream of TFBS | Poly dA/dT insertion |
| TDH3dAdT | TTTCCAAATCAGAGAGAGC AGAAGGTAATAGAAGGTTT TTTTTTTTTTTTTTTTTTGTA AGAAAATGAGATAGATACA TGCGTGGGTCAA (SEQ ID NO: 67) | ACACCT | ACAAA AAAA AAAA AAAA AAAA AACCT (SEQ ID NO: 132) | Upstream of TFBS | Poly dA/dT insertion |
| ZEOdAdT | AACTAAAGATGATAAAAAT AAAATTAGGTAAGAAATTTT TTTTTTTTTTTTTTTCCTTA ATTGGATATACAAAAATAC ACTGGAGGCAC (SEQ ID NO: 68) | AGGTTT | AGGA AAAA AAAA AAAA AAAA AAATT T (SEQ ID NO: 133) | Upstream of TFBS | Poly dA/dT insertion |
| PGKGcr1Log | AAACCTGTGAGCCGTCGCTA GGACCTTGTTGTGTGACGAA ATTNGWAGCTGCAATCAATA GGAAGACAGGAAGTCGAGC GTGTCTGGGTT (SEQ ID NO: 145) | GCTTCC AA | GCTW CNAA | TFBS | LOGO Mismatch |
| PGKMsn2aLog | ATGTAAATGTAAGTTTCACG AGGTTCTACTAAACTAAACC ACCCYTTGGTTAGAAGAAA AGAGTGTGTGAGAACAGGC GTTGTTGTCA (SEQ ID NO: 146) | AAGGGG | AARR GG | TFBS | LOGO Mismatch |
| PGKMsn2bLog | GCTCTGGAGATCACAGTGGG CATCATAGCATGTGGTACTA AACCYYTTCCCGCCATTCCA GAACCTTCGATTGCTTGTTAC AAAAACCTGT (SEQ ID NO: 147) | AAAGGG | AARR GG | TFBS | LOGO Mismatch |

TABLE 4-continued

List of ssODNs targeting the Beta Carotene pathway.

| | | | | | |
|---|---|---|---|---|---|
| PGKTye7Log | GACCAATTTATGCAAGTTTA TATATATGTAAATGTAAGTT TCWCGWGGTTCTACTAAACT AAACCACCCCCTTGGTTAGA AGAAAAGAGT (SEQ ID NO: 148) | CCTCGT G | CCWC GWG | TFBS | LOGO Mismatch |
| PGKHsf1Log | GTGGGCATCATAGCATGTGG TACTAAACCCTTTCCCGCCA YYCCAGRRCCTTCGATTGCT TGTTACAAAACCTGTGAGCC GTCGCTAGGA (SEQ ID NO: 149) | GAAGGT TCTGGA ATG (SEQ ID NO: 101 | GAAG GTTCT GGAA TG (SEQ ID NO: 101) | TFBS | LOGO Mismatch |
| TIP1phd1Log | GCTCGAAGAATTGGAGAGAA AAAAAGATGCTTTTAGAAAA TARGACMCATTTCCCGGAAC AATCAATTATTTCCATCACA ATCTTTGAAA (SEQ ID NO: 150) | GTGTCT | GKGT CY | TFBS | LOGO Mismatch |
| TIP1phd1bLog | GCCAATGTACTATTTATATTA AATGGTGAATGAAGCAACGC AGKACCYCAAAGAGGTTGG AGACATATTCACCCTTACAG CAAACCTTTT (SEQ ID NO: 151) | AGGTAC | RGGT MC | TFBS | LOGO Mismatch |
| TIP1adr1Log | ATATTAAATGGTGAATGAAG CAACGCAGTACCTCAAAGAG GTTYYRGACATATTCACCCT TACAGCAAACCTTTTTTTTCC TTTACTGGA (SEQ ID NO: 152) | TCTCCA A | TCYRR AA | TFBS | LOGO Mismatch |
| TIP1rgt1Log | GGATTCAAAACCACAAGTAC ATTCTTCAACGGAAAAGAGT CGGAWAATCGGAAAAGGGA CCTCCCGAAGACATTAGTCT CATAATTAAGG (SEQ ID NO: 153) | ATTTTCC | ATTW TCC | TFBS | LOGO Mismatch |
| TDH3Hsf1Log | ACCTTTTTTTTCAGCTTTTTC CAAATCAGAGAGCAGAA GGTRRTAGAAGGTGTAAGAA AATGAGATAGATACATGCGT GGGTCAATTG (SEQ ID NO: 154) | CCTTCT ATTACC TTC (SEQ ID NO: 102) | CCTTC TAYY ACCTT C (SEQ ID NO: 162) | TFBS | LOGO Mismatch |
| TDH3Pho2Log | AAACTAAAAAAAGACTAA CTATAAAGTAGAATTTAAG AAGWWWWWGAAATAGATT TACAGAATTACAATCAATAC CTACCGTCTTTAT (SEQ ID NO: 155) | CTTAAA | CWW WWW | TFBS | LOGO Mismatch |
| TDH3Pho2bLog | TGTTTGTTTATGTGTGTTTAT TCGAAACTAAGTTCTTGGTG TWWWWWWACTAAAAAAA AGACTAACTATAAAAGTAGA ATTTAAGAAGTT (SEQ ID NO: 156) | TTTAAA | WWW WWW | TFBS | LOGO Mismatch |
| TDH3Msn2aLog | TTACAATCAATACCTACCGT CTTTATATACTTATTAGTCAA GTARRRAATAATTTCAGGG AACTGGTTTCAACCTTTTTTT TCAGCTTT (SEQ ID NO: 157) | CCCCTA | TA | TFBS | LOGO Mismatch |
| TDH3Msn2bLog | CATCACTCCATTGAGGTTGT GCCCGTTTTTTGCCTGTTTGT GYYYYTGTTCTCTGTAGTTG CGCTAAGAGAATGGACCTAT GAACTGATG (SEQ ID NO: 158) | CAGGGG | CARRR R | TFBS | LOGO Mismatch |

TABLE 4-continued

List of ssODNs targeting the Beta Carotene pathway.

| | | | | | |
|---|---|---|---|---|---|
| TDH3Orc1Log | GTAGGGAATAATTTCAGGG AACTGGTTTCAACCTTWWW WWWCAGCWWWWWTCCAA ATCAGAGAGCAGAAGGT AATAGAAGGTGTAAGA (SEQ ID NO: 159) | GGAAAA AGCTGA AAAAA (SEQ ID NO: 103) | GGAW WWW WGCT GWW WWW W (SEQ ID NO: 163) | TFBS | LOGO Mismatch |
| ZEOgln3Log | GAGCAAACCAGCATTAACTA AAGATGATAAAAATAAAATT AGGTWWGWWWCCTTAATT GGATATACAAAAATACACTG GAGGCACAAATC (SEQ ID NO: 160) | TTTCTTA CCT (SEQ ID NO: 104) | WWW CWWA CCT (SEQ ID NO: 164) | TFBS | LOGO Mismatch |
| ZEOAce2Log | AGAGAAGAGGAGAACCGCA CAGAAAGCAGCAGAAACAG AGCAAAYYRRCATTAACTAA AGATGATAAAATAAAATTA GGTAAGAAACCT (SEQ ID NO: 161) | CTGGTT T | YYRRT TT | TFBS | LOGO Mismatch |
| ORF ssODNs | | | | | |
| CRTEStrt | AGTAAACTCGAGTGGAATT GCTGTGAGGATGTTCGCGTA ATCCACTTTTATTTTATTTAG CAGAGGGTATAGTTATCCTT TATAATTTCG (SEQ ID NO: 69) | ATG | GTG | Start Codon | Mismatch |
| CRTERare | TCTGCGGAATCCCGTAAATT AGATGGGCCACAGGCGACC CACGCCGGAGGACCGATGA ATCCTCCACATCGTCCATTA ATAAGCTAGCGG (SEQ ID NO: 70) | AGG | CGG | Abundant Arg Codon to Rare Arg Codon | Mismatch |
| CRTEOpt | TCTTGACATCCAACCAATAG TTGAAAGCCTCGATGAGTTG TGATCTAATTTCTTTTCCAG GGTTCTTTCCTAGGTAGTGA TACGGTTCAA (SEQ ID NO: 71) | CGA | AGA | Rare Arg Codon to Abundant Arg Codon | Mismatch |
| CRTEko | AGTTGTGATCGAATTTCTTT TCCAGGGTTCTTTCCTAGGT AGTGACTACGGTTCAAGGA GCACGATATCATCCTGAGGA GTAAACTCGAG (SEQ ID NO: 72) | TAT | TAGT | Nonsense Codon | Insertion |
| CRTIStrt | CCACGATGATAGCTGTGGGT TTATCCTGATCTTGTTCTTTT CCCACTTGTTTTATATTTGTT GTAAAAGTAGATAATTACT TCCTTGAT (SEQ ID NO: 73) | ATG | GTG | Start Codon | Mismatch |
| CRTIRar | TTTGACCCATGTACATCACT GCAAACGAGAAGACTCTTC GTAATCGGTCGGTCTTGAAA TATCGACAAACTCTTGTCCA GATAGACTCGA (SEQ ID NO: 74) | AGG | CGG | Abundant Arg Codon to Rare Arg Codon | Mismatch |
| CRTIOpt | GCAAGAGCAGCAAACTGGG CCCCTGATCGAATCGATAAC CATCTCTCTCGATTAAAGAG CATCGACCTCCGGAGTAGTC GTTCTTCTCGA (SEQ ID NO: 75) | CGA | AGA | Rare Arg Codon to Abundant Arg Codon | Mismatch |
| CRTIko | TCCGGAGTAGTCGTTCTTCT CGAACACCGTGACCTGGAA ACCTTCATTTAGCAAGACGA | TAT | TAGT | Nonsense Codon | Insertion |

TABLE 4-continued

List of ssODNs targeting the Beta Carotene pathway.

| | | | | | |
|---|---|---|---|---|---|
| | GCGGCAGTGGCGATTCCACC GATACCACATC (SEQ ID NO: 76) | | | | |
| CrYB2Strt | GGAGAGTATAGATCAGATG GATCTGGTAATATGCGAGA GCCGTCACTTTTGTTTGTTTA TGTGTGTTTATTCGAAACTA AGTTCTTGGTG (SEQ ID NO: 77) | ATG | GTG | Start Codon | Mismatch |
| CrYB2Rare | CGGACGATCTAGTCTTGGGA AGCGCGAGAGATGGGAGAA GGTGCCGAGTTGCCAAGAC GTAGACCAAGCCGGTGATT ACGGTTTGAATGA (SEQ ID NO: 78) | AGG | CGG | Arg Codon to Rare Arg Codon | Mismatch |
| CrYB2Opt | GATACACCGTCGGGATCATG ATTGCTGCAATAGTTGACTT TGCTCTGCCACTTTTCCAAT CGAAAGCATATTCGCCTGAT AATGCTGCCA (SEQ ID NO: 79) | CGA | AGA | Rare Arg Codon to Abundant Arg Codon | Mismatch |
| CrYB2ko | GCTGATGGATATGTCCATGC GCCATTTCTGATGATCCATG AGTCCTCATGGTGTGGTTGC ACTAAACGCAATAAATACG AGGATCGATAT (SEQ ID NO: 80) | TAT | TAGT | Nonsense Codon | Insertion |
| crYB04M | TCCGCTGATGGATATGTCCA TGCGCCATTTCTGATGATCC ATGAGCCCCATGGTGTGGTT GCACTAAACGCAATAAATA CGAGGATCGAT (SEQ ID NO: 81) | GGGACT CA | GGGGC TCA | crtYB Active Site | Mismatch |
| HMG1Strt | AGTAAAAGACTTCTTGGTGA CTTCAGTTTTCACCAATTGG TCCACTTATTAATTGATATA AACGTAGTTTTGTATGTTTC TTTGATTTGA (SEQ ID NO: 82) | ATG | GTG | Start Codon | Mismatch |
| HMG1Rare | CAGATGCTAATACAGGAGC TTCTGCCAAAATTGAAAGAG CCTTCCGACGTACCGCAACC GCTCTCGTAGTATCACCTAA TTTTTTCTCCA (SEQ ID NO: 83) | AGG | CGG | Abundant Arg Codon to Rare Arg Codon | Mismatch |
| HMG1Opt | AATTCTTCTAAAGGACGTAT TTTCTTATCCAAGCTTTCAA TATCTCTGGAATCATCTTCC TCACTAGATGATGAAGGTCC TGATGAGCTC (SEQ ID NO: 84) | CGC | AGA | Rare Arg Codon to Abundant Arg Codon | Mismatch |
| HMG1ko | ACGTATTTTCTTATCCAAGC TTTCAATATCGCGGGAATCA TCTTCACTCACTAGATGATG AAGGTCCTGATGAGCTCGAT TGCGCAGATG (SEQ ID NO: 85) | TAT | TAGT | Nonsense Codon | Insertion |
| Terminators | Terminator ssODNs | | | | |
| ttCIT1InpA | ATATAAATTATAAACTACTC ATTCGTATATGAAAATACGT GTAATAATTGAATAGTCGCA TACCCTGAATCAAAAATCAA ATTTTCCT (SEQ ID NO: 86) | CAAACA | CAATT ATTAC A (SEQ ID NO: 134) | Poly A signal site | Insertion |
| tACS2InpA | TAGAGCAAAAGTTGGGAAA ATAGAAAATAGAAAACAGA AAGAATAAGAGCGAAATT | CTCCTT | CTCTT ATTCT T (SEQ | Poly A signal site | Insertion |

TABLE 4-continued

List of ssODNs targeting the Beta Carotene pathway.

| | | | | | |
|---|---|---|---|---|---|
| | TTATCTCATTACGAAATTTT TCTCATTTAAGT (SEQ ID NO: 87) | | ID NO: 135) | | |
| ttASCIDpA | AAATATAGAAATTATTTTCT TTATTTTTACCATTTTAAAC ATGACCCTAGAAGATACAT AAAAGAACAAATGAACTTT ATACATATTCTC (SEQ ID NO: 88) | TAGTTAT TGGT (SEQ ID NO: 114) | TAGGG T | Putative Poly A signal site | Deletion |
| ttASCIDpAb | ACTTCGAAATCTATGACGAT TATATTATACACTAAAATAT AGAAATTTACCATTTTAAAC ATGACCAATAACTAGAAGA TACATAAAAGA (SEQ ID NO: 89) | AAAAAT AAAGAA AATAAT TT (SEQ ID NO: 115) | AAATT T | Putative Poly A signal site | Deletion |
| Gal4 Set | Gal4 TFBS ssODNs | | | | |
| Msn2aG4 | AATGTAAGTTTCACGAGGTT CTACTAAACTAAACCACCGG AGGAGAGTCTTCCGTGGTTA GAAGAAAAGAGTGTGTGAG AACAGGCTGTT (SEQ ID NO: 90) | AAGGG --- ---------GG | ACGGA AGACT CTCCT CCGG (SEQ ID NO: 136) | TFBS | Replaces TFBS with Gal4 TFBS |
| Msn2bG4 | GGAGATCACAGTGGGCATC GAGGAGAGTCTTCCGTCCCG CCATTCCAGAACCTTCGATT GCTTGTTACAA (SEQ ID NO: 91) | GAAAGG ------------ GT | GACGG TCTCC TCCGT (SEQ ID NO: 137) | TFBS | Replaces Gal4 TFBS |
| Hsf1G4 | ATAGCATGTGGTACTAAACG GGGGCATCATAGCATGTGGT ACTAAACCCTTTCCCGCCGG AGGAGAGTCTTCCGTGATTG CTTGTTACAAAACCTGTGAG CCGTCGCTAG (SEQ ID NO: 92) | TC --- GAAGGT TCTGGA ATGG (SEQ ID NO: 116) | AAGAC TCACG GAAG ACTCT CCTCC GG (SEQ ID NO: 138) | TFBS | TFBS with Replaces TFBS with Gal4 TFBS |
| phd1aG4 | AAGAATTGGAGAGAAAAAA AGATGCTTTTAGAAAATACG GAGGAGAGTCTTCCGTATTT CCCGGAACAATCAATTATTT CCATCACAATC (SEQ ID NO: 93) | GTGT ----- -------CTT | ACGGA AGACT CTCCT CCGT (SEQ ID NO: 137) | TFBS | Replaces TFBS with Gal4 TFBS |
| phd1bG4 | GTACTATTTATATTAAATGG TGAATGAAGCAACGCACGG AGGAGAGTCTTCCGTCAAA GAGGTTGGAGACATATTCAC CCTTACAGCAAA (SEQ ID NO: 94) | AGGTAC- -----------T | ACGGA AGACT CTCCT CCGT (SEQ ID NO: 137) | TFBS | Replaces TFBS with Gal4 TFBS |
| adr1G4 | AAATGGTGAATGAAGCAAC GCAGTACCTCAAAGAGGCG GAGGAGAGTCTTCCGTCATA TTCACCCTTACAGCAAACCT TTTTTTTCCTTT (SEQ ID NO: 95) | GTC------- ----- TCCAAC | GACGG AAGAC TCTCC TCCG (SEQ ID NO: 139) -C | TFBS | Replaces TFBS with Gal4 TFBS |
| Msn2aG4 | TCAATACCTACCGTCTTTAT ATACTTATTAGTCAAGCGGA GGAGAGTCTTCCGTAATAAT TTCAGGGAACTGGTTTCAAC CTTTTTTTC (SEQ ID NO: 96) | ATT-------- ---- CCCCTA CTT | ATTAC GGAA GACTC TCCTC CGCTT (SEQ ID NO: 140) | TFBS | Replaces TFBS with Gal4 TFBS |
| Msn2bG4 | CTCCATTGAGGTTGTGCCCG TTTTTTGCCTGTTTGTGCGG | AACAGG G---------- | AAACG GAAG | TFBS | Replaces TFBS with |

TABLE 4-continued

List of ssODNs targeting the Beta Carotene pathway.

| | | | | | |
|---|---|---|---|---|---|
| | AGGAGAGTCTTCCGTTTCTC TGTAGTTGCGCTAAGAGAAT GGACCTATGA (SEQ ID NO: 97) | -GC | ACTCT CCTCC GC (SEQ ID NO: 141) | | Gal4 TFBS |
| Orc1G4 | GTAGGGGAATAATTTCAGG GAACTGGTTTCAACCTTCGG AGGAGAGTCTTCCGTAAATC AGAGAGAGCAGAAGGTAAT AGAAGGTGTAAG (SEQ ID NO: 98) | TT-- GGAAAA AGCTGA AAAAAA AGG (SEQ ID NO: 117) | TTACG GAAG ACTCT CCTCC GAA (SEQ ID NO: 142) -GG | TFBS | Replaces TFBS with Gal4 TFBS |
| gln3G4 | AAACCAGCATTAACTAAAG ATGATAAAAATAAAATTCG GAGGAGAGTCTTCCGTCCTT AATTGGATATACAAAAATA CACTGGAGGCACA (SEQ ID NO: 99) | AGG------- -- TTTCTTA CCTAA (SEQ ID NO: 118) | AGGAC GGAA GACTC TCCT(S EQ ID NO: 143) CCGAA | TFBS | Replaces TFBS with Gal4 TFBS |
| Ace2G4 | AGAGGAGAACCGCACAGAA AGCAGCAGAAACAGAGCCG GAGGAGAGTCTTCCGTCATT AACTAAAGATGATAAAAAT AAAATTAGGTAAG (SEQ ID NO: 100) | GCTGGT TT---------- -GC | GACGG AAGAC TCTCC TCCGG C (SEQ ID NO: 144) | TFBS | Replaces TFBS with Gal4 TFBS |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated, genetically modified or transfected eukaryotic cell comprising a RAD51 gene or a homolog thereof, and a selectable marker adjacent to a eukaryotic origin of replication, wherein the cell is treated or altered to reduce the expression of the RAD51 gene or the homolog thereof or to reduce or inhibit the RAD51 gene product or the homolog thereof, compared to an untreated or unaltered cell.

2. The cell of claim 1, wherein there are no intact genes between the origin of replication and the selectable marker.

3. The cell of claim 1, wherein the cell comprises a genetic modification that reduces the effectiveness of intrinsic DNA damage prevention, DNA damage repair, or a combination thereof.

4. The cell of claim 1, wherein the cell comprises a genetic modification that reduces the effectiveness of a post-replicative DNA mismatch repair system (MMR).

5. The cell of claim 1, wherein the cell comprises a mutation or deletion at rad51 or a homolog thereof, rad52 or a homolog thereof, or a combination thereof.

6. The cell of claim 1, wherein the cell comprises a mutation or deletion at msh or a homolog thereof, mlh or a homolog thereof, pms or a homolog thereof, or a combination thereof.

7. The cell of claim 1, wherein the cell expresses or overexpresses rad59 or a homolog thereof.

8. The cell of claim 1, wherein the cell expresses a heterologous ssDNA annealing or binding protein or a homolog thereof, or recombinase or a homolog thereof or a combination thereof.

9. The cell of claim 1, wherein the cell is a yeast, fungal, mammalian, insect, or plant cell.

10. The cell of claim 1, wherein the origin of replication is an endogenous origin of replication on a chromosome of the cell.

11. The cell of claim 1, wherein the cell was genetically modified to place the selectable marker adjacent to the origin of replication.

12. The cell of claim 1, further comprising (a) an oligonucleotide that can introduce one or more mutations into the selectable marker when incorporated into the cell's genome by replication fork annealing and (b) one or more oligonucleotides that can introduce one or more mutations into a target region when incorporated into the cell's genome by replication fork annealing.

13. The cell of claim 12, wherein the oligonucleotides of (a) and (b) target the lagging strand of the chromosome during replication.

14. A method for preparing a library of mutant eukaryotic cells comprising
  (i) transfecting or transforming a population of eukaryotic host cells of claim 1 with (a) an oligonucleotide that can introduce one or more mutations into the selectable marker when incorporated into a cell's genome by replication fork annealing and (b) one or more oligonucleotides that can introduce one or more mutations into a target region when incorporated into the cell's genome by replication fork annealing; and
  (ii) selecting mutant cells that have a mutation in the selectable marker.

15. The method of claim 14, wherein the target region and the selectable marker are separated by 2, 1, or 0 origins of replication.

16. The method of claim 14, wherein the target region has a length from between 1 base pair and 100 million base pairs from the origin of replication closest to the selectable marker.

17. The method of claim 14, wherein the selectable marker is a counter-selectable marker and mutant cells are selected by culturing the transfected cells in presences of a compound that kills cells expressing an un-mutated selectable marker.

18. The method of claim 14, wherein the one or more oligonucleotides of step (b) introduce mutations into a gene regulatory region, an open reading frame, an intron, or a combination thereof.

19. The method of claim 18, wherein the mutations are insertions, deletions, substitutions, or a combination thereof.

20. The method of claim 14, wherein the oligonucleotides of (a) and (b) are each about 30 and 120 nucleotides in length.

21. The method of claim 14, wherein the oligonucleotides of (b) are a pool of oligonucleotides each comprising 1 or more mutations.

22. The method of claim 14, further comprising (iii) selecting mutant cells that have a mutation in the target region.

23. The method of claim 22, wherein the selection of mutant cells with a mutation in the target region comprises phenotypic or genotypic screening.

24. The method of claim 14, wherein the host cells are selected from the group consisting of animal cells, ciliate cells, plant cells, fungi, yeasts, flagellates, microsporidia, and protozoa.

25. The method of claim 14, wherein the host cells have reduced expression of one or more DNA mismatch repair enzymes.

26. The method of claim 25, wherein the DNA mismatch repair enzyme is selected from the group consisting of MSH2, MSH6, MLH1, PMS1, homologs thereof, and combinations thereof.

27. The method of claim 14, wherein the host cells have increased expression of RAD59, an ssDNA annealing or binding protein, or recombinase.

28. The method of claim 14, comprising treating the host cells with a compound that transiently slows the DNA replication fork in an effective amount to increase efficiency of oligonucleotide incorporation prior to and/or during step (i).

29. The method of claim 28, wherein the compound is hydroxyurea.

30. The method of claim 14, wherein steps (i) and (ii) are repeated for two or more cycles using the same or different oligonucleotides for steps (a) and (b).

31. The method of claim 14, wherein the target region comprises a native or heterologous biological pathway comprising two or more genes, and wherein oligonucleotides of step (b) target two or more of the genes in the pathway.

32. A library of mutant cells prepared according to the method of claim 14.

33. A single cell or clonal colony thereof isolated from the library of claim 32.

* * * * *